(12) United States Patent
Dhanoa et al.

(10) Patent No.: US 7,491,727 B2
(45) Date of Patent: Feb. 17, 2009

(54) ARYLPIPERAZINYL COMPOUNDS

(75) Inventors: Dale S. Dhanoa, Delmar, CA (US);
Dongli Chen, Brighton, MA (US); Oren Becker, Mevaseret Zion (IL); Silvia Noiman, Herzliyya (IL); Srinivasa R. Cheruku, Lexington, MA (US); Yael Marantz, Kfar Shmuel (IL); Anurag Sharadendu, Washington, DC (US); Sharon Shacham, Alfey Menashe (IL); Alexander Heifetz, Bnei-Brak (IL); Pradyumna Mohanty, Woburn, MA (US); Boaz Inbal, Kfar Shmuel (IL); Merav Fichman, Modi'in (IL); Raphael Nudelman, Rehovot (IL); Shay Bar-Haim, Netanya (IL)

(73) Assignee: Epix Delaware, Inc., Lexington, MA (US)

( * ) Notice: Subject to any disclaimer, the term of this patent is extended or adjusted under 35 U.S.C. 154(b) by 11 days.

(21) Appl. No.: 11/516,345

(22) Filed: Sep. 5, 2006

(65) Prior Publication Data
US 2007/0004742 A1 Jan. 4, 2007

Related U.S. Application Data

(63) Continuation of application No. 10/768,579, filed on Jan. 30, 2004, now Pat. No. 7,153,858.

(60) Provisional application No. 60/503,520, filed on Sep. 16, 2003, provisional application No. 60/458,297, filed on Mar. 28, 2003, provisional application No. 60/443,988, filed on Jan. 31, 2003.

(51) Int. Cl.
*A61K 31/495* (2006.01)
*A61K 31/496* (2006.01)

(52) U.S. Cl. ............................ 514/253.01; 514/255.03

(58) Field of Classification Search ........................ None
See application file for complete search history.

(56) References Cited

U.S. PATENT DOCUMENTS

| | | | |
|---|---|---|---|
| 2,722,529 | A | 11/1955 | Fleming et al. |
| 4,948,892 | A | 8/1990 | Tanabe et al. |
| 5,137,901 | A | 8/1992 | Junge et al. |
| 5,300,523 | A | 4/1994 | Junge et al. |
| 5,478,828 | A | 12/1995 | Mattson et al. |
| 5,506,246 | A | 4/1996 | Junge et al. |
| 5,585,392 | A | 12/1996 | Junge et al. |
| 5,602,124 | A | 2/1997 | Tehim et al. |
| 5,789,412 | A | 8/1998 | Halazy et al. |
| 6,391,882 | B1 | 5/2002 | Moltzen et al. |
| 6,423,717 | B1 | 7/2002 | Bromidge et al. |
| 6,476,050 | B2 | 11/2002 | Aquila et al. |
| 6,599,904 | B2 | 7/2003 | Bromidge et al. |
| 6,635,661 | B2 | 10/2003 | Cuny et al. |
| 6,645,980 | B1 | 11/2003 | Cuny et al. |
| 7,153,858 | B2 | 12/2006 | Dhanoa et al. |
| 2001/0056090 | A1 | 12/2001 | Aquila et al. |
| 2002/0016337 | A1 | 2/2002 | Cuny et al. |
| 2002/0035113 | A1 | 3/2002 | Moltzen et al. |
| 2002/0065265 | A1 | 5/2002 | Wu et al. |
| 2002/0123499 | A1 | 9/2002 | Persons et al. |
| 2002/0177721 | A1 | 11/2002 | Aquila et al. |
| 2003/0050309 | A1 | 3/2003 | Aquila et al. |
| 2003/0069233 | A1 | 4/2003 | Bromidge et al. |
| 2003/0069418 | A1 | 4/2003 | Aquila et al. |
| 2003/0073681 | A1 | 4/2003 | Hauske et al. |
| 2003/0092694 | A1 | 5/2003 | Nilsson et al. |
| 2003/0114436 | A1 | 6/2003 | Aquila et al. |
| 2005/0171347 | A1 | 8/2005 | Emelen et al. |
| 2006/0205737 | A1 | 9/2006 | Becker et al. |

FOREIGN PATENT DOCUMENTS

| | | |
|---|---|---|
| EP | 089089 | 9/1983 |
| EP | 0434561 | 6/1991 |
| EP | 661266 | 7/1995 |
| EP | 0946539 | 10/1999 |
| JP | 59029665 | 2/1984 |
| JP | 9202764 | 5/1997 |
| WO | WO-95/04049 | 2/1995 |
| WO | WO-0056712 | 9/2000 |
| WO | WO-03009850 | 2/2003 |

OTHER PUBLICATIONS

Jones et al. Pharmacology, Biochemistry and Behavior, vol. 71, p. 555-568 (2002).*
Weisler, Expert Opin.Emerging Drugs, vol. 12, pp. 423-434 (2007).*
Jankovic, Mount Sinai Journal of Medicine, vol. 73, p. 682-689 (2006).*

(Continued)

*Primary Examiner*—Emily Bernhardt
(74) *Attorney, Agent, or Firm*—Goodwin Procter LLP

(57) ABSTRACT

The invention relates to 5-HT receptor agonists or antagonists. Novel arylpiperazinyl sulfonamide compounds represented by Formula I, and synthesis and uses thereof for treating diseases including those mediated directly or indirectly by 5-HT receptors, are disclosed. Such conditions include central nervous system disorders such as generalized anxiety disorder, ADD/ADHD, neural injury, stroke, and migraine. Methods of preparation and novel intermediates and pharmaceutical salts thereof are also included.

8 Claims, 12 Drawing Sheets

OTHER PUBLICATIONS

Brown et al. Drug Discovery Today, vol. 12, pp. 757-766 (2007).*
Uchida et al. Chemical Abstracts vol. 127, No. 220471 (1997) (Abstract for JP 09202764, Aug. 5, 1997).
Bojarski, et al., Bioorganic Med. Chem., 10:3817-3827 (2002).
Oh, et al., Curr. Med. Chem., 8:999-1034 (2001).
Rasmussen, et al., J. Pharmacol. Experimental Therapeutics, 294(2):688-700 (2000).
Lopez-Rodriguez et al. J. Med. Chem. vol. 44, pp. 198-207 (2001).
Becker et al. J. Med. Chem. vol. 49, pp. 3116-3135 (2006).
International Search Report for Application No. PCT/US04/02858 dated Sep. 2, 2004 (1 page).
Supplementary European Search Report for Application No. EP 04 70 74 09 dated Dec. 18, 2006 (3 pages).
Art cited by Examiner in First Notification of Office Action from The State Intellectual Property Office of the People's Republic of China for Application No. 2004800055827 dated Sep. 29, 2006 (7 pages).

* cited by examiner

Figure 1: Effect of Compound A on Proportion of Open Arm Entries in the Elevated Plus Maze test.
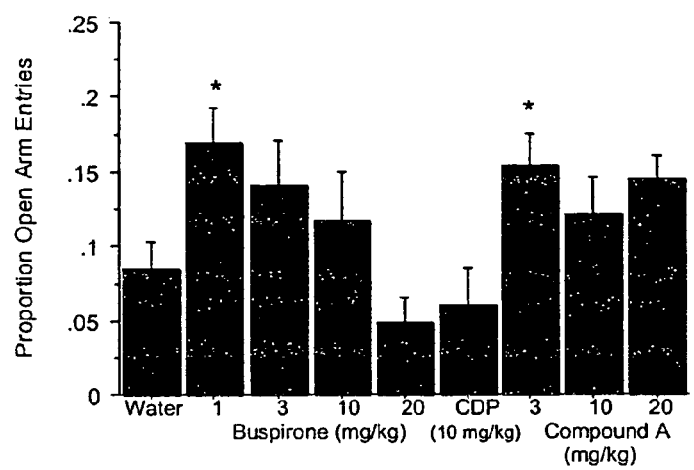

Figure 2: Effect of Compound A on Open Arm Time in the Elevated Plus Maze test.
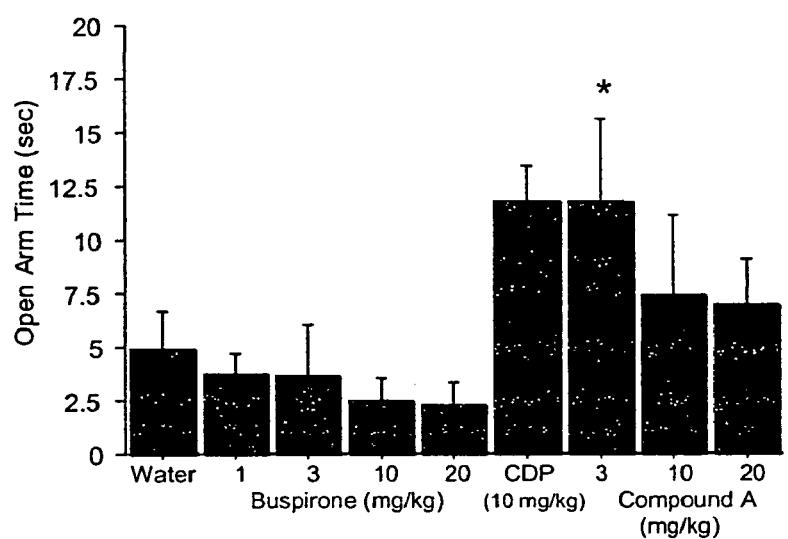

Figure 3: Effect of Compound A on Closed Arm Entries in the Elevated Plus Maze test.
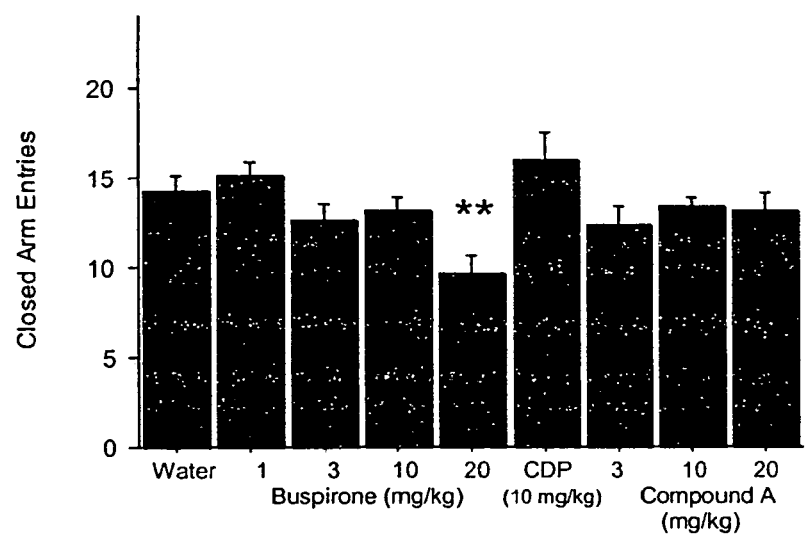

Figure 4: Effect of Compound A on Total Number of Entries in the Elevated Plus Maze test.
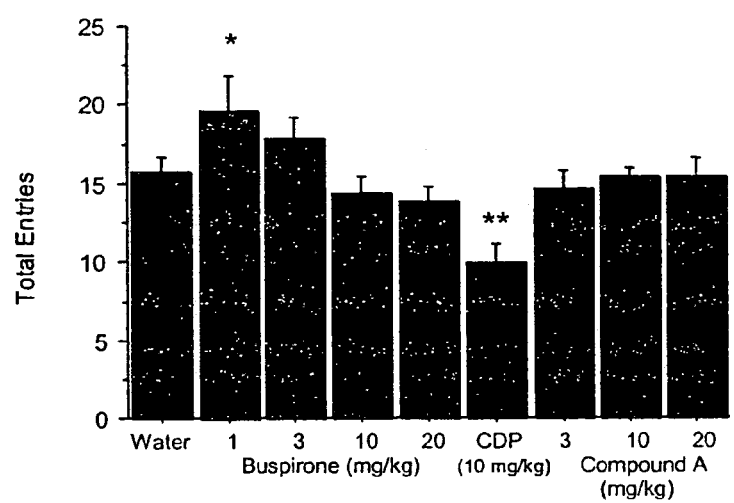

Figure 5: Effect of Compound A on Basal Rectal Temperature (°C) in the Stress-Induced Hyperthermia test.
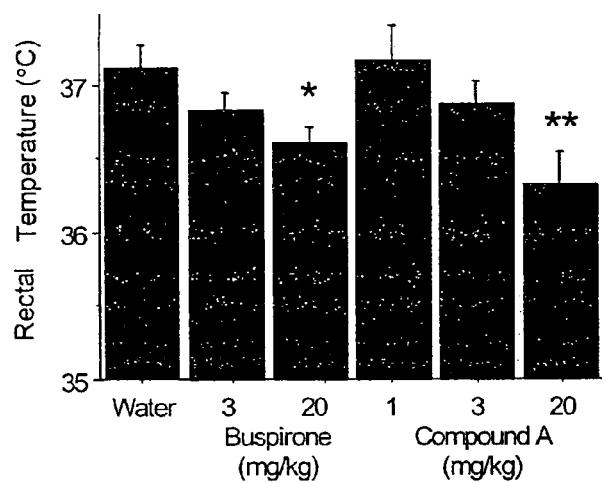

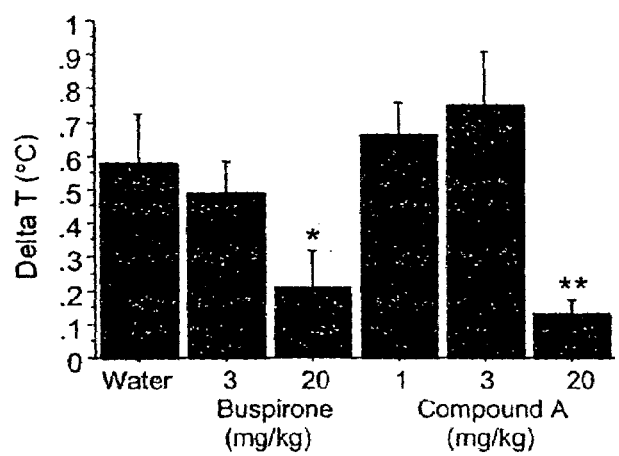
Figure 6: Effect of Compound A on Delta T (°C) in the Stress-Induced Hyperthermia test.

Figure 7: Effect of Compound A on Total Distance Traveled (Horizontal Activity) in the Open Field.
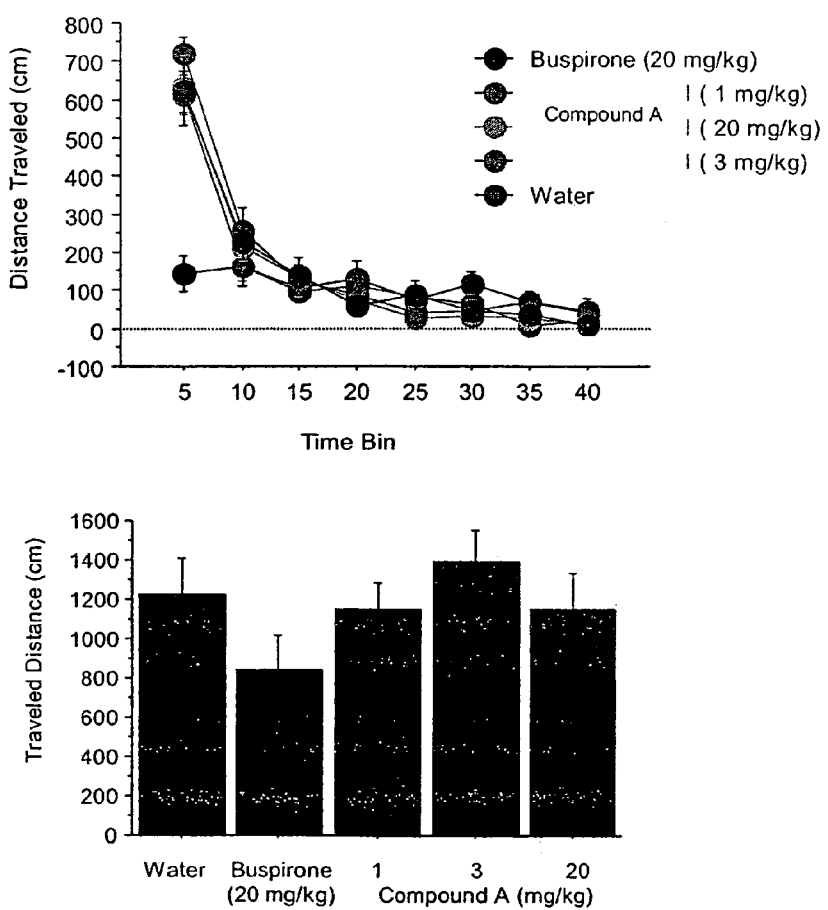

Figure 8: Effect of Compound A on rearing activity (Vertical Activity) in the Open Field.
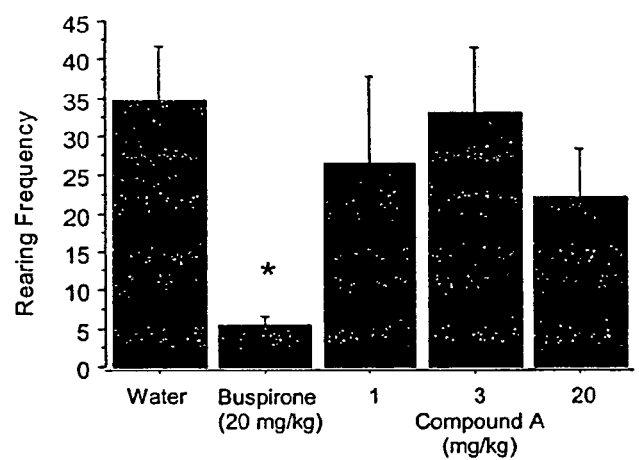

Figure 9: Effect of Compound A on Percent Distance Traveled in the Center in the Open Field during the period of 40 min.
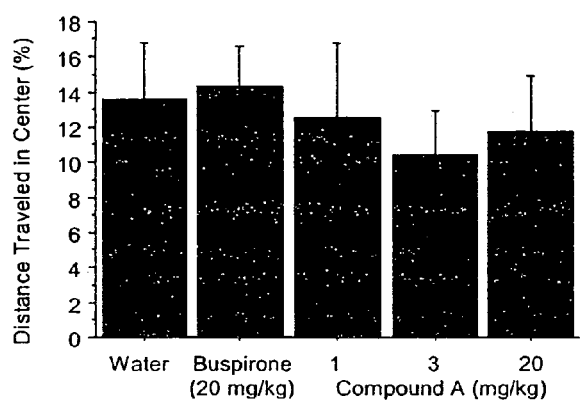

Figure 10: Effect of Compound A on Percent Time Traveled in the Center in the Open Field during the period of 40 min.
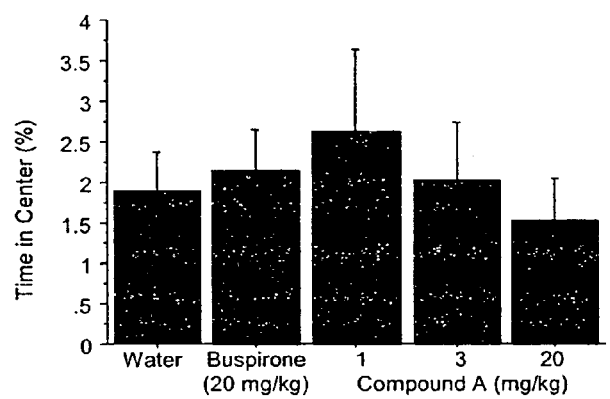

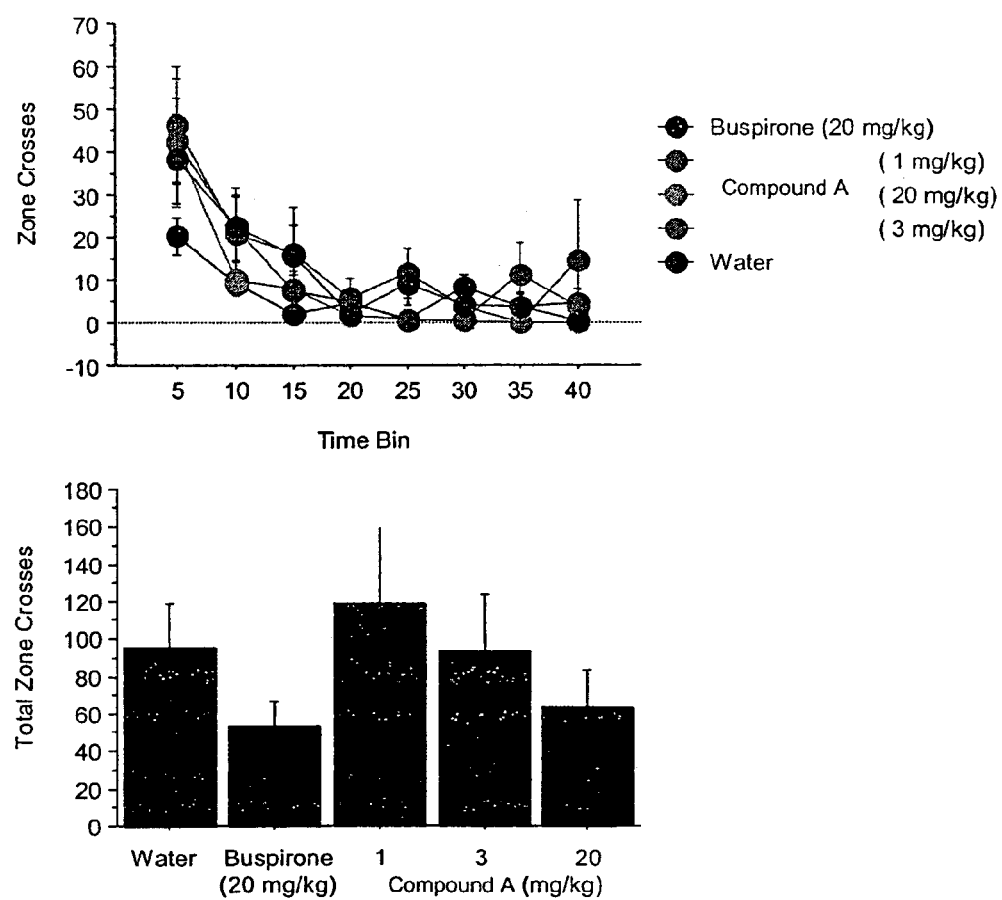
Figure 11: Effect of Compound A on Frequency of Zone Crosses in the Open Field.

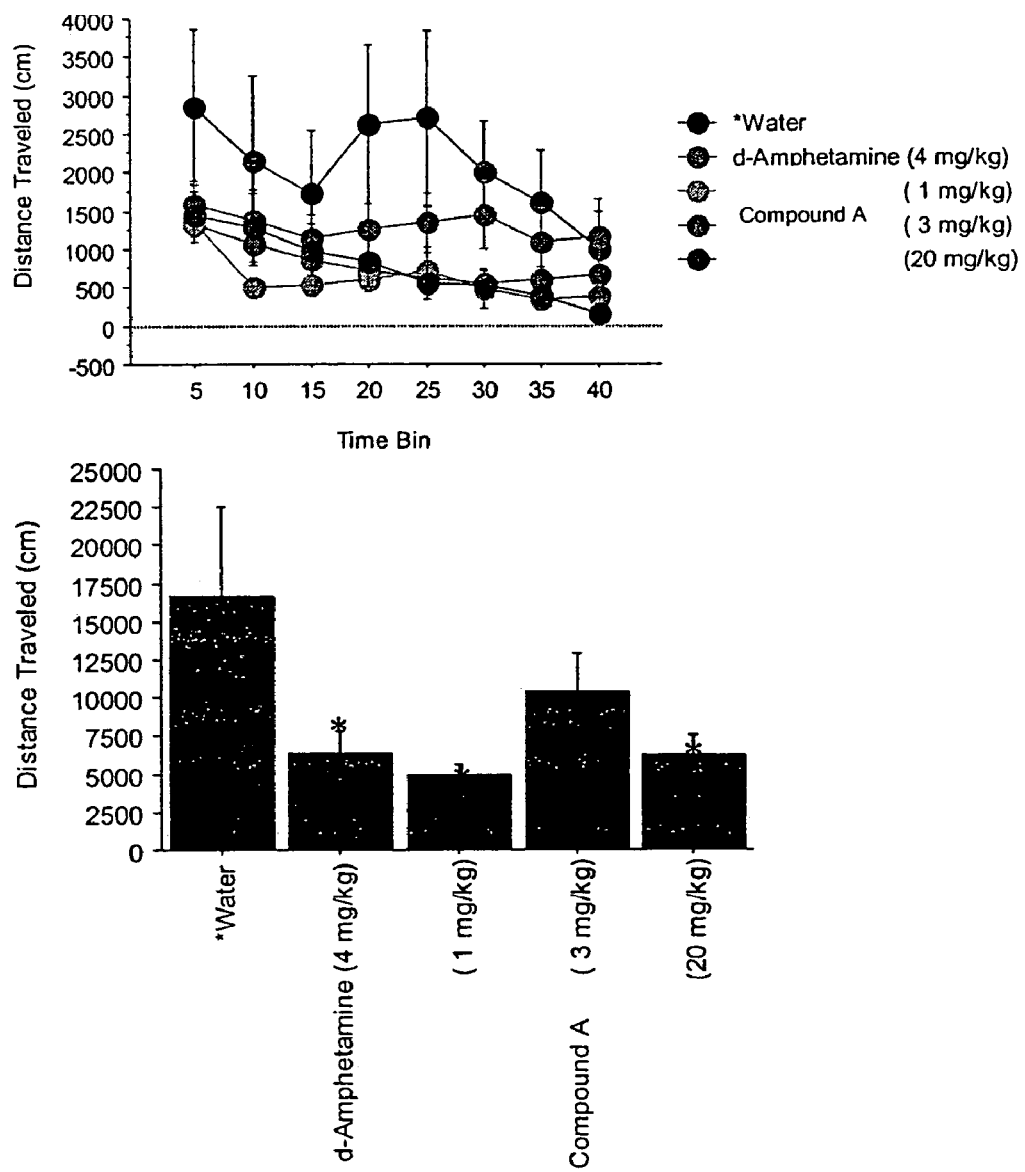
Figure 12: Effect of Compound A on Distance Traveled in the Open Field.

ARYLPIPERAZINYL COMPOUNDS

RELATED APPLICATIONS

This application is a continuation of U.S. Ser. No. 10/768,579, now U.S. Pat. No. 7,153,858, which claims the benefit of priority under 35 U.S.C. 119(e) to copending U.S. Provisional Application Nos. 60/443,988 filed on Jan. 31, 2003; 60/458,297, filed on Mar. 28, 2003, and 60/503,520, file on Sep. 16, 2003, the entire contents of which are incorporated herein by reference.

FIELD OF THE INVENTION

The invention generally relates to the field of serotonin (5-hydroxytryptamine, or 5-HT) receptor modulators, e.g., agonists or antagonists, and more particularly to new arylpiperazinyl compounds which are also 5-HT modulators, and use of these compounds, e.g. in the treatment, modulation and/or prevention of physiological conditions associated with serotonin action.

BACKGROUND OF THE INVENTION

The serotonergic neural system of the brain has been shown to influence a variety of physiologic functions which manifest themselves in a variety of disorders such as eating disorders, schizophrenia, neuralgia, and addiction disorders; depression, obsessive compulsive disorders, panic disorders, anxiety, sexual dysfunctions caused by the central nervous system and disturbances in sleep and the absorption of food, alcoholism, pain, memory deficits, unipolar depression, dysthymia, bipolar depression, treatment-resistant depression, depression in the medically ill, panic disorder, obsessive-compulsive disorder, eating disorders, social phobia, and premenstrual dysphoric disorder.

5-HT receptor modulators e.g., agonists or antagonists, and/or selective serotonin reuptake inhibitors (SSRIs) such as fluoxetine, paroxetine, fluvoxamine, sertraline, lorazepam, imipramine, citalopram, and nortriptyline, may be used for the treatment of the above conditions, as well as for vasodilation, smooth muscle contraction, bronchoconstriction, brain disorders such as vascular disorders such as angina and migraine; and neuropathological disorders including Parkinson's disease and Alzheimer's disease. These compounds are also suitable for the modulation of the cardiovascular system. They also intervene in the regulation of the cerebral circulation and thus represent effective agents for controlling migraine. They are also suitable for the prophylaxis and control of the effects of occurrences of cerebral infarct (*Apoplexia cerebri*) such as stroke or cerebral ischemia. They are also suitable for the control of disorders of the intestinal tract which are characterized by disturbances of the serotoninergic system and also by disturbances of the carbohydrate metabolism.

Trazodone controls 5-HT actions, and fluoxetine and fluvoxamine facilitate serotoninergic neurotransmission via potent and selective inhibition of serotonin reuptake into presynaptic neurons. 3-chloroimipramine inhibits both 5-HT and norepinephrine reuptake. Other compounds of current interest as antidepressants include zimeldine, bupropion and nomifensine.

SUMMARY OF THE INVENTION

It is desired to have selective, high affinity, metabolically stable 5-HT receptor modulators that possess good bioavailability, CNS penetration, and good pharmacokinetic properties, e.g., in vivo. The present invention relates to the discovery of new compounds for treating subjects method of treating a subject afflicted with a condition requiring treatment, by administering an effective amount of a compound of the invention to treat the condition(s). Various conditions will be responsive to the introduction of these compounds, alone and/or in combination with other drugs; or the compounds may be used to alter physiological phenomena associated with certain conditions to achieve a desired treatment of said condition(s), alone and/or in combination with other drugs.

For example, the compounds of the invention may be used for vasodilation, smooth muscle contraction, bronchoconstriction, brain disorders such as vascular disorders, e.g., blood flow disorders caused by vasodilation and vasospastic diseases such as angina, vascular headache, migraine and Reynaud's disease; and neuropathological disorders including Parkinson's disease and Alzheimer's disease; modulation of the cardiovascular system; prophylaxis and control of the effects of occurrences of cerebral infarct (*Apoplexia cerebri*) such as stroke or cerebral ischemia; and for the control of disorders of the intestinal tract which are characterized by disturbances of the serotoninergic system and also by disturbances of the carbohydrate metabolism. The compounds may also be useful in treating stress-related somatic disorders; reflex sympathetic dystrophy such as shoulder/hand syndrome; disorders of bladder function such as cystitis, bladder detrusor hyper-reflexia and incontinence; and pain or nociception attributable to or associated with any of the foregoing conditions, especially pain transmission in migraine.

In one advantageous aspect, the compounds of the invention have been found to be 5-HT modulators, e.g., agonists or antagonists, and/or SSRIs, that can be used for treating, preventing or curing 5-HT-related conditions. In particular, it has been found that certain arylpiperazinyl sulfonamide compounds are effective 5-HT receptor modulators and/or SSRIs.

In an embodiment, compounds of the invention include those having the formula

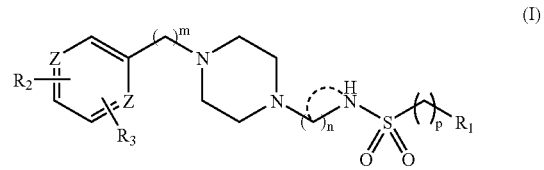

(I)

wherein $R_1$ is a functional group that imparts substantially no $5\text{-HT}_{1A}/5\text{-HT}_{2A}$ adrenergic receptor cross-reactivity to the compound; $R_2$ and $R_3$ independently are hydrogen or a functional group that imparts substantially no HERG channel inhibition to the compound; Z is N or C; m may be 0, 1, 2, 3, 4, 5, or 6; n may be 1, 2, 3, 4, 5, or 6; and p may be 0, 1, 2, 3, or 4, more preferably greater than 0; and pharmaceutically acceptable salts and/or esters thereof. m is advantageously 0, n is advantageously 3 or 4, and p is advantageously 0 or 1.

$R_1$ may be substituted or unsubstituted aryl, alkyl, cycloalkyl or alkylaryl; and $R_2$ and $R_3$ independently may be hydrogen or lower alkyl; cycloalkyl; trihalomethyl; halo; —$NR_4R_5$, where $R_4$ and $R_5$ are independently H, O, $R_6$, or $COR_6$, where $R_6$ may be lower alkyl (e.g., nitro, NHCO-alkyl, e.g., NHCO-lower alkyl such as NHCO—$(C_2-C_4)$alkyl, including NHCO—$(CH_3)$, NHCO—$(CH_2CH_3)$, NHCO—$(CH_2CH_2—CH_3)$, NHCO—$(CH(CH_2)_2)$ (i.e., cyclopropyl) and NCO-dialkyl, aminoalkyl, e.g., amino(lower)alkyl such as aminomethyl, aminoethyl, aminopropyl, aminocyclopropyl, aminobutyl or dialkylamino); sulfonamidoalkyl, e.g., sulfonamido$(C_2-C_4)$alkyl; hydroxyl; cyano; or a conjugated five- or six-membered cyclic or heterocyclic ring, provided that $R_2$ and $R_3$ are not both hydrogen. When p=0, $R_1$ is desirably a group other than substituted or unsubstituted aryl, and $R_2$ and $R_3$ independently are desirably other than phenyl or alkoxyphenyl.

The aryl, pyridinyl, pyrimidinyl or pyrazinyl (i.e., where Z=N) group may be substituted with a substituent such as lower alkyl, e.g., $C_1-C_4$; cycloalkyl, e.g., $C_1-C_6$; trihalomethyl, e.g., $CF_3$ or $OCF_3$; halo, e.g. F, Br or Cl; a conjugated five- or six-membered cyclic or heterocyclic ring, e.g., 3,4-methylenedioxy; nitro; NHCO-alkyl, e.g., NHCO-lower alkyl such as NHCO—$(C_2-C_4)$alkyl, including NHCO—$(CH_3)$, NHCO—$(CH_2CH_3)$, NHCO—$(CH_2CH_2—CH_3)$, and NHCO—$(CH(CH_2)_2)$ (i.e., cyclopropyl); NCO-dialkyl; sulfonamidoalkyl, e.g. sulfonamido$(C_2-C_4)$alkyl; hydroxyl; or cyano. The aryl group itself may be, e.g., substituted or unsubstituted phenyl, naphthyl, toluyl, or biphenyl.

Compounds of the invention are also 5-HT receptor agonists or antagonists, e.g., 5-$HT_1$ receptor agonists or antagonists including 5-$HT_{1A, B, C, D, E\ or\ F}$ receptors, and desirably 5-$HT_{1A}$ receptor agonists. Surprisingly, it has been found that compounds of the invention are very good 5-$HT_{1A}$ receptor agonists and have superior activity and selectivity. The compounds of the invention are more selective in their action, displaying little or no cross-reactivity with other receptors such as α-adrenergic receptors. Furthermore, compounds of the invention show little is or no HERG channel inhibition, which would otherwise be a disadvantage for drugs based on compounds of the invention. As such, the utility of the compounds of the invention as, e.g., anti-anxiety agents, is greatly enhanced.

In an embodiment, $R_1$ may be lower alkyl, e.g., n-butyl, s-butyl, i-butyl; p-toluene, p-halophenyl (e.g., p-fluorophenyl, p-chlorophenyl or p-bromophenyl), cycloalkyl, e.g., cyclopropyl, cyclobutyl, cyclopentyl, cyclohexyl, cyclohexylmethyl, and cyclohexylphenyl. In a version of this embodiment, $R_2$ may be aminoalkyl, e.g., amino(lower)alkyl such as aminomethyl, aminoethyl, aminopropyl, aminocyclopropyl, aminobutyl or dialkylamino. In another version, $R_2$ may be NHCO-alkyl, e.g. NHCO—$(C_2-C_4)$alkyl, including NHCO—$(CH_3)$, NHCO—$(CH_2CH_3)$, NHCO—$(CH_2CH_2—CH_3)$, and NHCO—$(CH(CH_2)_2$ (i.e., NHCO-cyclopropyl.)

In an embodiment, $R_3$ is H and $R_2$ is other than H and in the meta-position. In a version of this embodiment, $R_2$ may be aminoalkyl, e.g., amino(lower)alkyl such as aminomethyl, aminoethyl, aminopropyl, aminocyclopropyl, aminobutyl or dialkylamino. In another version, $R_2$ may be NHCO-alkyl, e.g., NHCO—$(C_2-C_4)$alkyl, including NHCO—$(CH_3)$, NHCO—$(CH_2CH_3)$, NHCO—$(CH_2CH_2—CH_3)$, and NHCO—$(CH(CH_2)_2$ (i.e., NHCO-cyclopropyl.) In a version of this embodiment, $R_1$ may be p-toluene, p-halophenyl (e.g. p-fluorophenyl, p-chlorophenyl or p-bromophenyl), cyclohexylmethyl, cyclohexyl, or cyclohexylphenyl.

In a further embodiment, compounds of the invention include those having the formula

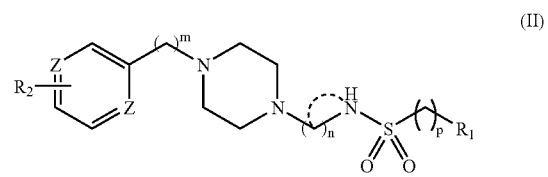

wherein $R_1$ may be substituted or unsubstituted aryl, alkyl, cycloalkyl or alkylaryl, e.g., toluyl or cyclohexyl. $R_1$ is preferably unconjugated when it is a ring-containing group, and may advantageously be substituted or unsubstituted alkyl or cycloalkyl, e.g., cyclohexyl. $R_2$ may be lower alkyl, e.g., $C_1-C_4$; trihalomethyl, e.g., $CF_3$; halo, e.g., F, Br or Cl; a conjugated five- or six-membered cyclic or heterocyclic ring, e.g., 3,4-methylenedioxy; —$NR_4R_5$, where $R_4$ and $R_5$ are independently H, O or $COR_6$, where $R_6$ may be lower alkyl, e.g., nitro; NHCO-alkyl, e.g., NHCO-lower alkyl such as NHCO—$(C_2-C_4)$alkyl, including NHCO—$(CH_3)$, NHCO—$(CH_2CH_3)$, NHCO—$(CH_2CH_2—CH_3)$, and NHCO—$(CH(CH_2)_2)$ (i.e., cyclopropyl); NCO-dialkyl; sulfonamidoalkyl, e.g., sulfonamido$(C_2-C_4)$alkyl; the atoms denoted by the dotted line bond may, taken together, form a four, five, six or seven membered cyclic or heterocyclic ring; Z is N or C; m may be 0, 1 or 2; n may be 1, 2, 3, or 4; and p may be 0 or 1; and pharmaceutically acceptable salts and/or esters thereof. m is advantageously 0, n is advantageously 3 or 4, and p is advantageously 0 or 1.

In an embodiment, $R_1$ may be lower alkyl, e.g., n-butyl, s-butyl, i-butyl; p-toluene, p-halophenyl (e.g., p-fluorophenyl, p-chlorophenyl or p-bromophenyl), cycloalkyl, e.g., cyclopropyl, cyclobutyl, cyclopentyl, cyclohexyl, cyclohexylmethyl, and cyclohexylphenyl. Advantageously, $R_1$ may be cycloalkyl, e.g., cyclopropyl, cyclobutyl, cyclopentyl, cyclohexyl, cyclohexylmethyl, and cyclohexylphenyl. In this embodiment, $R_2$ may be aminoalkyl, e.g., amino(lower)alkyl such as aminomethyl, aminoethyl, aminopropyl, aminocyclopropyl, aminobutyl or dialkylamino. Advantageously, $R_2$ may be NHCO-alkyl, e.g., NHCO—$(C_2-C_4)$alkyl, including NHCO—$(CH_3)$, NHCO—$(CH_2CH_3)$, NHCO—$(CH_2CH_2—CH_3)$, and NHCO—$(CH(CH_2)_2$ (i.e., NHCO-cyclopropyl.)

In an embodiment, $R_2$ is in the meta-position. In a version of this embodiment, $R_2$ may be aminoalkyl, e.g., amino(lower)alkyl such as aminomethyl, aminoethyl, aminopropyl, aminocyclopropyl, aminobutyl or dialkylamino. In another version, $R_2$ may be NHCO-alkyl, e.g., NHCO—$(C_2-C_4)$alkyl, including NHCO—$(CH_3)$, NHCO—$(CH_2CH_3)$, NHCO—$(CH_2CH_2—CH_3)$, and NHCO—$(CH(CH_2)_2$ (i.e., NHCO-cyclopropyl.) In a version of this embodiment, $R_1$ may be n-butyl, s-butyl, i-butyl, p-toluene, p-halophenyl (e.g., p-fluorophenyl, p-chlorophenyl or p-bromophenyl), cyclohexylmethyl, cyclohexyl, or cyclohexylphenyl. The compounds of the invention are advantageously pharmaceutically acceptable salts, e.g., HCl.

In particular embodiments, compounds of the invention include 4-Methyl-N-{4-[4-(3-nitro-phenyl)-piperazin-1-yl]-butyl}-benzenesulfonamide; 4-Methyl-N-{4-[4-(3-nitro-phenyl)-piperazin-1-yl]-butyl}-benzenesulfonamide HCl salt; Cyclopropanecarboxylic acid (3-{4-[4-(toluene-4-sulfonylamino)-butyl]-piperazin-1-yl}-phenyl)-amide; N-(3-{4-[4-(Toluene-4-sulfonylamino)-butyl]-piperazin-1-yl}-phenyl)-butyramide; 2,2-Dimethyl-N-(3-{4-[4-(toluene-4-sulfonylamino)-butyl]-piperazin-1-yl}-phenyl)- propionamide; N-(3-{4-[4-(Toluene-4-sulfonylamino)-butyl]-piperazin-1-yl}-phenyl)-isobutyramide; N-{4-[4-(3-Ethanesulfonylamino-phenyl)-piperazin-1-yl]-butyl}-4-methyl-benzenesulfonamide; 4-Methyl-N-(4-{4-[3-(propane-2-sulfonylamino)-phenyl]-piperazin-1-yl}-butyl)-benzenesulfonamide; 4-Methyl-N-{4-[4-(3-nitro-phenyl)-piperazin-1-yl]-butyl}-benzenesulfonamide; 4-Methyl-N-[4-(4-pyridin-2-yl-piperazin-1-yl)-butyl]-benzenesulfonamide; N-{4-[4-(2-Methoxy-5-nitro-phenyl)-piperazin-1-yl]-butyl}-4-methyl-benzenesulfonamide; 4-Methyl-N-[4-(4-pyrimidin-2-yl-piperazin-1-yl)-butyl]-benzenesulfonamide; N-{4-[4-(3-Methoxy-phenyl)-piperazin-1-yl]-butyl}-4-methyl-benzenesulfonamide; N-{4-[4-(3-Ethanesulfonylamino-phenyl)-piperazin-1-yl]-butyl}-4-methyl-benzenesulfonamide; N-{4-[4-(3-Methanesulfonylamino-phenyl)-piperazin-1-yl]-butyl}-4-methyl-benzenesulfonamide; 4-Methyl-N-{4-[4-(3-pyrazin-2-yl-phenyl)-piperazin-1-yl]-butyl}-benzenesulfonamide; N-[4-(4-Biphenyl-3-yl-piperazin-1-yl)-butyl]-4-methyl-benzenesulfonamide, 4-Methyl-N-[4-(4-phenyl-piperazin-1-yl)-butyl]-benzenesulfonamide, C-Cyclohexyl-N-{4-[4-(2-methoxy-phenyl)-piperazin-1-yl]-butyl}-methanesulfonamide, N-(3-{4-[4-(Toluene-4-sulfonylamino)-butyl]-piperazin-1-yl}-phenyl)-acetamide, N-(3-{4-[4-(Toluene-4-sulfonylamino)-butyl]-piperazin-1-yl}-phenyl)-propionamide, (3-{4-[1-(4-Fluoro-benzenesulfonyl)-piperidin-4-ylmethyl]-piperazin-1-yl}-phenyl)-dimethyl-amine, 1-[1-(4-Fluoro-benzenesulfonyl)-piperidin-4-ylmethyl]-4-pyridin-2-yl-piperazine, C-Cyclohexyl-N-{4-[4-(3-dimethylamino-phenyl)-piperazin-1-yl]-butyl}-methanesulfonamide, C-Cyclohexyl-N-[4-(4-pyridin-2-yl-piperazin-1-yl)-butyl]-methanesulfonamide, N-(3-{4-[1-(4-Fluoro-benzenesulfonyl)-piperidin-4-ylmethyl]-piperazin-1-yl}-phenyl)-acetamide, N-(3-{4-[4-(4-Fluoro-benzenesulfonylamino)-butyl]-piperazin-1-yl}-phenyl)-acetamide, N-{3-[4-(4-Cyclohexylmethanesulfonylamino-butyl)-piperazin-1-yl]-phenyl}-acetamide, N-{3-[4-(1-Cyclohexylmethanesulfonyl-piperidin-4-ylmethyl)-piperazin-1-yl]-phenyl}-acetamide, Cyclopropanecarboxylic acid {3-[4-(4-cyclohexylmethane-sulfonylamino-butyl)-piperazin-1-yl]-phenyl}-amide, N-(3-{4-[1-(Propane-2-sulfonyl)-piperidin-4-ylmethyl]-piperazin-1-yl}-phenyl)-acetamide, N-(3-{4-[4-(Propane-2-sulfonylamino)-butyl]-piperazin-1-yl}-phenyl)-acetamide, N-{3-[4-(4-Cyclohexanesulfonylamino-butyl)-piperazin-1-yl]-phenyl}-acetamide, N-(3-{4-[4-(Cyclohexylmethane-sulfonyl-methyl-amino)-butyl]-piperazin-1-yl}-phenyl)-acetamide, N-(3-{4-[4-(2-Methyl-propane-1-sulfonylamino)-butyl]-piperazin-1-yl}-phenyl)-acetamide, N-[3-(4-{4-[Methyl-(2-methyl-propane-1-sulfonyl)-amino]-butyl}-piperazin-1-yl)-phenyl]-acetamide, N-(3-Piperazin-1-yl-phenyl)-acetamide, Cyclopropanecarboxylic acid (3-piperazin-1-yl-phenyl)-amide, and 1-(2-Methoxy-phenyl)-4-[1-(toluene-4-sulfonyl)-piperidin-3-ylmethyl]-piperazine.

Another aspect of the invention, as noted above, includes methods for treating subjects afflicted with a condition requiring treatment, by administering an effective amount of a compound of the invention to treat the condition(s). Subjects suffering from various conditions that will be responsive to the introduction of these compounds may be treated; or the compounds may be used to alter physiological phenomena associated with certain conditions to achieve a desired treatment of said condition(s), alone and/or in combination with other drugs. Such conditions or physiological phenomena include vasodilation, smooth muscle contraction, bronchoconstriction, brain disorders such as vascular disorders, e.g., blood flow disorders caused by vasodilation and vasospastic diseases such as angina, vascular headache, migraine and Reynaud's disease; and neuropathological disorders including Parkinson's disease and Alzheimer's disease; modulation of the cardiovascular system; prophylaxis and control of the effects of occurrences of cerebral infarct (*Apoplexia cerebri*) such as stroke or cerebral ischemia; and for the control of disorders of the intestinal tract which are characterized by disturbances of the serotoninergic system and also by disturbances of the carbohydrate metabolism; stress-related somatic disorders; reflex sympathetic dystrophy such as shoulder/hand syndrome; disorders of bladder function such as cystitis, bladder detrusor hyper-reflexia and incontinence; and pain or nociception attributable to or associated with any of the foregoing conditions, especially pain transmission in migraine.

The invention is also drawn to methods of treating conditions associated with serotonergic hypofunction or hyperfunction, including administering a compound of the invention to a subject to treat the condition. As explained above, compounds of the invention can have antagonistic activity at $5\text{-HT}_{1A}$ receptors, which will counteract the negative feedback mechanism induced by the inhibition of serotonin reuptake; this is thereby expected to improve the effect of the serotonin reuptake inhibiting activity of the compounds of the invention. Other compounds of the invention have agonistic activity at 5-HT receptors like $5\text{-HT}_{1A}$.

Another aspect of the invention is a pharmaceutical composition comprising an amount of a compound according to Formula I or II effective to treat anxiety, particularly generalized anxiety disorder, in a mammal suffering therefrom, and a pharmaceutically acceptable carrier.

Another aspect of the invention is a method for treating anxiety, particularly generalized anxiety disorder, in a mammal such as a human comprising administering a therapeutically effective amount of a compound according to Formula I or II.

Another aspect of the invention is a pharmaceutical composition comprising an amount of a compound according to Formula I or II effective to treat panic disorder in a mammal suffering therefrom, and a pharmaceutically acceptable carrier.

Another aspect of the invention is a method for treating panic disorder in a mammal such as a human comprising administering a therapeutically effective amount of a compound according to Formula I or II.

Another aspect of the invention is a pharmaceutical composition comprising an amount of a compound according to Formula I or II effective to treat attention deficit disorder (ADD), with or without hyperactivity, i.e., ADHD, in a mammal suffering therefrom, and a pharmaceutically acceptable carrier.

Another aspect of the invention is a method for treating attention deficit disorder, with or without hyperactivity, in a mammal such as a human comprising administering a therapeutically effective amount of a compound according to Formula I or II.

Another aspect of the invention is a pharmaceutical composition comprising an amount of a compound according to Formula I or II effective to treat substance-related disorders in a mammal suffering therefrom, and a pharmaceutically acceptable carrier.

Another aspect of the invention is a method for treating substance-related disorders in a mammal such as a human comprising administering a therapeutically effective amount of a compound according to Formula I or II.

Another aspect of the invention is a pharmaceutical composition comprising an amount of a compound according to Formula I or II effective in treating conditions associated with vascular disorders, e.g., angina and migraine.

Another aspect of the invention is a method of treating conditions associated with vascular disorders, e.g., angina and migraine.

Processes for preparing the compounds and novel intermediates are also included in the invention.

BRIEF DESCRIPTION OF THE DRAWING

FIGS. 1-12 illustrate the effects on animals of a compound of the invention in various tests, as detailed further in Examples 40 and 41.

DETAILED DESCRIPTION OF THE INVENTION

The features and other details of the invention will now be more particularly described with reference to the accompanying drawings and pointed out in the claims. It will be understood that particular embodiments described herein are shown by way of illustration and not as limitations of the invention. The principal features of this invention can be employed in various embodiments without departing from the scope of the invention. All parts and percentages are by weight unless otherwise specified.

Definitions

For convenience, certain terms used in the specification, examples, and appended claims are collected here.

"5-HT receptor modulator" or "5-HT modulator" includes compounds having effect at the $5\text{-HT}_1$, $5\text{-HT}_2$, $5\text{-HT}_3$, $5\text{-HT}_4$, $5\text{-HT}_5$, $5\text{-HT}_6$ or $5\text{-HT}_7$ receptors, including the subtypes of each receptor type, such as $5\text{-HT}_{1A, B, C, D, E \text{ or } F}$; $5\text{-HT}_{2A, B \text{ or } C}$; and $5\text{-HT}_{5A \text{ or } B}$. 5-HT modulators may be agonists, partial agonists or antagonists.

"Treating", includes any effect, e.g., lessening, reducing, modulating, or eliminating, that results in the improvement of the condition, disease, disorder, etc.

"Alkyl" includes saturated aliphatic groups, including straight-chain alkyl groups (e.g., methyl, ethyl, propyl, butyl (e.g., n-butyl, s-butyl, i-butyl), pentyl, hexyl, heptyl, octyl, nonyl, decyl), branched-chain alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. "Alkyl" further includes alkyl groups which have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), and more preferably four or fewer. Likewise, preferred cycloalkyls have from three to eight carbon atoms in their ring structure, and more preferably have five or six carbons in the ring structure. "$C_1$-$C_6$" includes alkyl groups containing one to six carbon atoms.

The term "alkyl" also includes both "unsubstituted alkyls" and "substituted alkyls", the latter of which refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). "Alkyl" also includes the side chains of natural and unnatural amino acids.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain.) Likewise, cycloalkenyl groups may have from three to eight carbon atoms in their ring structure, and more preferably have five or six carbons in the ring structure. The term "$C_2$-$C_6$" includes alkenyl groups containing two to six carbon atoms.

The term "alkenyl" also includes both "unsubstituted alkenyls" and "substituted alkenyls", the latter of which refers to alkenyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms.

The term "alkynyl" also includes both "unsubstituted alkynyls" and "substituted alkynyls", the latter of which refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2-5 carbon atoms.

"Acyl" includes compounds and moieties which contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

"Aroyl" includes compounds and moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The terms "heterocyclyl" or "heterocyclic group" include closed ring structures, e.g., 3- to 10-, or 4- to 7-membered rings, which include one or more heteroatoms. Heterocyclyl groups can be saturated or unsaturated and include pyrrolidine, oxolane, thiolane, piperidine, piperazine, morpholine, lactones, lactams such as azetidinones and pyrrolidinones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl"

which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

"Polycyclyl" or "polycyclic radical" refers to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkyithiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

"Heteroatom" includes atoms of any element other than carbon or hydrogen. Examples of heteroatoms include nitrogen, oxygen, sulfur and phosphorus.

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

Combination therapy" (or "co-therapy") includes the administration of a 5-HT modulator of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g. Silverman, R. B. *The Organic Chemistry of Drug Design and Drug Action*, Academic Press, Inc. San Diego, Calif., 1992, pp. 19-23). A particularly preferred anionic group is a carboxylate.

The term "heterocyclic group" is intended to include closed ring structures in which one or more of the atoms in the ring is an element other than carbon, for example, nitrogen, or oxygen or sulfur. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like.

The present invention relates to the discovery of new compounds for treating subjects suffering from various conditions that will be responsive to the introduction of these compounds, alone and/or in combination with other drugs. For example, the compounds of the invention may be used for vasodilation, smooth muscle contraction, bronchoconstriction, brain disorders such as vascular disorders, e.g., blood flow disorders caused by vasodilation and vasospastic diseases such as angina, vascular headache, migraine and Reynaud's disease; and neuropathological disorders including Parkinson's disease and Alzheimer's disease; modulation of the cardiovascular system; prophylaxis and control of the effects of occurrences of cerebral infarct (*Apoplexia cerebri*) such as stroke or cerebral ischemia; and for the control of disorders of the intestinal tract which are characterized by disturbances of the serotoninergic system and also by disturbances of the carbohydrate metabolism. The compounds may also be useful in treating stress-related somatic disorders; reflex sympathetic dystrophy such as shoulder/hand syndrome; disorders of bladder function such as cystitis, bladder detrusor hyper-reflexia and incontinence; and pain or nociception attributable to or associated with any of the foregoing conditions, especially pain transmission in migraine.

In one advantageous aspect, the compounds of the invention have been found to be 5-HT modulators, e.g., agonists or antagonists, and/or SSRIs, that can be used for treating, preventing or curing 5-HT-related conditions. In particular, it has been found that certain arylpiperazinyl sulfonamide compounds are effective 5-HT receptor modulators and/or SSRIs.

In an embodiment, compounds of the invention include those having the formula

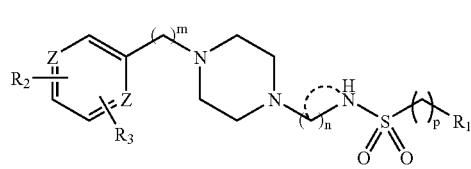

(I)

wherein $R_1$ is a functional group that imparts substantially no 5-HT$_{1A}$/5-HT$_{2A}$ adrenergic receptor cross-reactivity to the compound; $R_2$ and $R_3$ independently are hydrogen or a functional group that imparts substantially no HERG channel inhibition to the compound; Z is N or C; m maybe 0, 1, 2, 3, 4, 5, or 6; n may be 1, 2, 3, 4, 5, or 6; and p may be 0, 1, 2, 3, or 4, more preferably greater than 0; and pharmaceutically acceptable salts and/or esters thereof. m is advantageously 0, n is advantageously 3 or 4, and p is advantageously 0 or 1.

$R_1$ may be substituted or unsubstituted aryl, alkyl, cycloalkyl or alkylaryl; and $R_2$ and $R_3$ independently may be hydrogen or lower alkyl; cycloalkyl; trihalomethyl; halo; —NR$_4$R$_5$, where R$_4$ and R$_5$ are independently H, O, R$_6$, or COR$_6$, where R$_6$ may be lower alkyl (e.g., nitro, NHCO-alkyl, e.g., NHCO-lower alkyl such as NHCO—(C$_2$-C$_4$)alkyl, including NHCO—(CH$_3$), NHCO—(CH$_2$CH$_3$), NHCO—(CH$_2$CH$_2$—CH$_3$), NHCO—(CH(CH$_2$)$_2$) (i.e., cyclopropyl) and NCO-dialkyl, aminoalkyl, e.g., amino(lower)alkyl such as aminomethyl, aminoethyl, aminopropyl, aminocyclopropyl, aminobutyl or dialkylamino); sulfonamidoalkyl, e.g., sulfonamido(C$_2$-C$_4$)alkyl; hydroxyl; cyano; or a conjugated five- or six-membered cyclic or heterocyclic ring, provided that $R_2$ and $R_3$ are not both hydrogen.

The aryl, pyridinyl, pyrimidinyl or pyrazinyl (i.e., where Z=N) group may be substituted with a substituent such as lower alkyl, e.g., C$_1$-C$_4$; cycloalkyl, e.g., C$_1$-C$_6$; trihalomethyl, e.g., CF$_3$ or OCF$_3$; halo, e.g., F, Br or Cl; a conjugated five- or six-membered cyclic or heterocyclic ring, e.g., 3,4-methylenedioxy; nitro; NHCO-alkyl, e.g., NHCO-lower alkyl such as NHCO—(C$_2$-C$_4$)alkyl, including NHCO—(CH$_3$), NHCO—(CH$_2$CH$_3$), NHCO—(CH$_2$CH$_2$—CH$_3$), and NHCO—(CH(CH$_2$)$_2$) (i.e., cyclopropyl); NCO-dialkyl; sulfonamidoalkyl, e.g., sulfonamido(C$_2$-C$_4$)alkyl; hydroxyl; or cyano. The aryl group itself may be, e.g., substituted or unsubstituted phenyl, naphthyl, toluyl, or biphenyl.

In an embodiment, $R_1$ may be lower alkyl, e.g., n-butyl, s-butyl, i-butyl; p-toluene, p-halophenyl (e.g., p-fluorophenyl, p-chlorophenyl or p-bromophenyl), cycloalkyl, e.g., cyclopropyl, cyclobutyl, cyclopentyl, cyclohexyl, cyclohexylmethyl, and cyclohexylphenyl. In a version of this embodiment, $R_2$ may be aminoalkyl, e.g., amino(lower)alkyl such as aminomethyl, aminoethyl, aminopropyl, aminocyclopropyl, aminobutyl or dialkylamino. In another version, $R_2$ may be NHCO-alkyl, e.g., NHCO—(C$_2$-C$_4$)alkyl, including NHCO—(CH$_3$), NHCO—(CH$_2$CH$_3$), NHCO—(CH$_2$CH$_2$—CH$_3$), and NHCO—(CH(CH$_2$)$_2$ (i.e., NHCO-cyclopropyl.)

In an embodiment, $R_3$ is H and $R_2$ is other than H and in the meta-position. In a version of this embodiment, $R_2$ may be aminoalkyl, e.g., amino(lower)alkyl such as aminomethyl, aminoethyl, aminopropyl, aminocyclopropyl, aminobutyl or dialkylamino. In another version, $R_2$ may be NHCO-alkyl, e.g., NHCO—(C$_2$-C$_4$)alkyl, including NHCO—(CH$_3$), NHCO—(CH$_2$CH$_3$), NHCO—(CH$_2$CH$_2$—CH$_3$), and NHCO—(CH(CH$_2$)$_2$ (i.e., NHCO-cyclopropyl.) In a version of this embodiment, $R_1$ may be p-toluene, p-halophenyl (e.g., p-fluorophenyl, p-chlorophenyl or p-bromophenyl), cyclohexylmethyl, cyclohexyl, or cyclohexylphenyl.

In a further embodiment, compounds of the invention include those having the formula

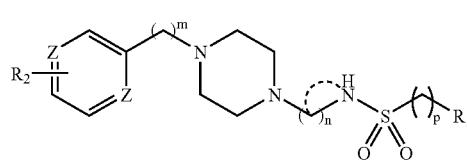

(II)

wherein $R_1$ may be substituted or unsubstituted aryl, alkyl, cycloalkyl or alkylaryl, e.g., toluyl or cyclohexyl. $R_1$ is preferably unconjugated when it is a ring-containing group, and may advantageously be substituted or unsubstituted alkyl or cycloalkyl, e.g. cyclohexyl. $R_2$ may be lower alkyl, e.g., C$_1$-C$_4$; trihalomethyl, e.g, CF$_3$; halo, e.g., F, Br or Cl; a conjugated five- or six-membered cyclic or heterocyclic ring, e.g., 3,4-methylenedioxy; —NR$_4$R$_5$, where R$_4$ and R$_5$ are independently H, O or COR$_6$, where R$_6$ may be lower alkyl, e.g., nitro; NHCO-alkyl, e.g., NHCO-lower alkyl such as NHCO—(C$_2$-C$_4$)alkyl, including NHCO—(CH$_3$), NHCO—(CH$_2$CH$_3$), NHCO—(CH$_2$CH$_2$—CH$_3$), and NHCO—(CH(CH$_2$)$_2$) (i.e., cyclopropyl); NCO-dialkyl; sulfonamidoalkyl, e.g., sulfonamido(C$_2$-C$_4$)alkyl; the atoms denoted by the dotted line bond may, taken together, form a four, five, six or seven membered cyclic or heterocyclic ring; Z is N or C; m may be 0, 1 or 2; n may be 1, 2, 3, or 4; and p may be 0 or 1; and pharmaceutically acceptable salts and/or esters thereof.

m is advantageously 0, n is advantageously 3 or 4, and p is advantageously 0 or 1.

In an embodiment, $R_1$ may be lower alkyl, e.g., n-butyl, s-butyl, i-butyl; p-toluene, p-halophenyl (e.g., p-fluorophenyl,p-chlorophenyl or p-bromophenyl), cycloalkyl, e.g., cyclopropyl, cyclobutyl, cyclopentyl, cyclohexyl, cyclohexylmethyl, and cyclohexylphenyl. Advantageously, $R_1$ may be cycloalkyl, e.g., cyclopropyl, cyclobutyl, cyclopentyl, cyclohexyl, cyclohexylmethyl, and cyclohexylphenyl. In this embodiment, $R_2$ may be aminoalkyl, e.g., amino(lower)alkyl such as aminomethyl, aminoethyl, aminopropyl, aminocyclopropyl, aminobutyl or dialkylamino. Advantageously, $R_2$ may be NHCO-alkyl, e.g., NHCO—$(C_2$-$C_4)$alkyl, including NHCO—$(CH_3)$, NHCO—$(CH_2CH_3)$, NHCO—$(CH_2CH_2$—$CH_3)$, and NHCO—$(CH(CH_2)_2$ (i.e., NHCO-cyclopropyl.)

In an embodiment, $R_2$ is in the meta-position. In a version of this embodiment, $R_2$ may be aminoalkyl, e.g., amino(lower)alkyl such as aminomethyl, aminoethyl, aminopropyl, aminocyclopropyl, aminobutyl or dialkylamino. In another version, $R_2$ may be NHCO-alkyl, e.g., NHCO—$(C_2$-$C_4)$ alkyl, including NHCO—$(CH_3)$, NHCO—$(CH_2CH_3)$, NHCO—$(CH_2CH_2$—$CH_3)$, and NHCO—$(CH(CH_2)_2$ (i.e., NHCO-cyclopropyl.) In a version of this embodiment, $R_1$ may be n-butyl, s-butyl, i-butyl, p-toluene, p-halophenyl (e.g., p-fluorophenyl, p-chlorophenyl or p-bromophenyl), cyclohexylmethyl, cyclohexyl, or cyclohexylphenyl. The compounds of the invention are advantageously pharmaceutically acceptable salts, e.g., HCl.

In particular embodiments, compounds of the invention include 4-Methyl-N-{4-[4-(3-nitro-phenyl)-piperazin-1-yl]-butyl}-benzenesulfonamide; 4-Methyl-N-{4-[4-(3-nitro-phenyl)-piperazin-1-yl]-butyl}-benzenesulfonamide HCl salt; Cyclopropanecarboxylic acid (3-{4-[4-(toluene-4-sulfonylamino)-butyl]-piperazin-1-yl}-phenyl)-amide; N-(3-{4-[4-(Toluene-4-sulfonylamino)-butyl]-piperazin-1-yl}-phenyl)-butyramide; 2,2-Dimethyl-N-(3-{4-[4-(toluene-4-sulfonylamino)-butyl]-piperazin-1-yl}-phenyl)-propionamide; N-(3-{4-[4-(Toluene-4-sulfonylamino)-butyl]-piperazin-1-yl}-phenyl)-isobutyramide; N-{4-[4-(3-Ethanesulfonylamino-phenyl)-piperazin-1-yl]-butyl}-4-methyl-benzenesulfonamide; 4-Methyl-N-(4-{4-[3-(propane-2-sulfonylamino)-phenyl]-piperazin-1-yl}-butyl)-benzenesulfonamide; 4-Methyl-N-{4-[4-(3-nitro-phenyl)-piperazin-1-yl]-butyl}-benzenesulfonamide; 4-Methyl-N-[4-(4-pyridin-2-yl-piperazin-1-yl)-butyl]-benzenesulfonamide; N-{4-[4-(2-Methoxy-5-nitro-phenyl)-piperazin-1-yl]-butyl}-4-methyl-benzenesulfonamide; 4-Methyl-N-[4-(4-pyrimidin-2-yl-piperazin-1-yl)-butyl]-benzenesulfonamide; N-{4-[4-(3-Methoxy-phenyl)-piperazin-1-yl]-butyl}-4-methyl-benzenesulfonamide; N-{4-[4-(3-Ethanesulfonylamino-phenyl)-piperazin-1-yl]-butyl}-4-methyl-benzenesulfonamide; N-{4-[4-(3-Methanesulfonylamino-phenyl)-piperazin-1-yl]-butyl}-4-methyl-benzenesulfonamide; 4-Methyl-N-{4-[4-(3-pyrazin-2-yl-phenyl)-piperazin-1-yl]-butyl}-benzenesulfonamide; N-[4-(4-Biphenyl-3-yl-piperazin-1-yl)-butyl]-4-methyl-benzenesulfonamide, 4-Methyl-N-[4-(4-phenyl-piperazin-1-yl)-butyl]-benzenesulfonamide, C-Cyclohexyl-N-{4-[4-(2-methoxy-phenyl)-piperazin-1-yl]-butyl}-methanesulfonamide, N-(3-{4-[4-(Toluene-4-sulfonylamino)-butyl]-piperazin-1-yl}-phenyl)-acetamide, N-(3-{4-[4-(Toluene-4-sulfonylamino)-butyl]-piperazin-1-yl}-phenyl)-propionamide, (3-{4-[1-(4-Fluoro-benzenesulfonyl)-piperidin-4-ylmethyl]-piperazin-1-yl}-phenyl)-dimethyl-amine, 1-[1-(4-Fluoro-benzenesulfonyl)-piperidin-4-ylmethyl]-4-pyridin-2-yl-piperazine, C-Cyclohexyl-N-{4-[4-(3-dimethylamino-phenyl)-piperazin-1-yl]-butyl}-methanesulfonamide, C-Cyclohexyl-N-[4-(4-pyridin-2-yl-piperazin-1-yl)-butyl]-methanesulfonamide, N-(3-{4-[1-(4-Fluoro-benzenesulfonyl)-piperidin-4-ylmethyl]-piperazin-1-yl}-phenyl)-acetamide, N-(3-{4-[4-(4-Fluoro-benzenesulfonylamino)-butyl]-piperazin-1-yl}-phenyl)-acetamide, N-{3-[4-(4-Cyclohexylmethanesulfonylamino-butyl)-piperazin-1-yl]-phenyl}-acetamide, N-{3-[4-(1-Cyclohexylmethanesulfonyl-piperidin-4-ylmethyl)-piperazin-1-yl]-phenyl}-acetamide, Cyclopropanecarboxylic acid {3-[4-(4-cyclohexylmethane-sulfonylamino-butyl)-piperazin-1-yl]-phenyl}-amide, N-(3-{4-[1-(Propane-2-sulfonyl)-piperidin-4-ylmethyl]-piperazin-1-yl}-phenyl)-acetamide, N-(3-{4-[4-(Propane-2-sulfonylamino)-butyl]-piperazin-1-yl}-phenyl)-acetamide, N-{3-[4-(4-Cyclohexanesulfonylamino-butyl)-piperazin-1-yl]-phenyl}-acetamide, N-(3-{4-[4-(Cyclohexylmethane-sulfonyl-methyl-amino)-butyl]-piperazin-1-yl}-phenyl)-acetamide, N-(3-{4-[4-(2-Methyl-propane-1-sulfonylamino)-butyl]-piperazin-1-yl}-phenyl)-acetamide, N-[3-(4-{4-[Methyl-(2-methyl-propane-1-sulfonyl)-amino]-butyl}-piperazin-1-yl)-phenyl]-acetamide, N-(3-Piperazin-1-yl-phenyl)-acetamide, Cyclopropanecarboxylic acid (3-piperazin-1-yl-phenyl)-amide, and 1-(2-Methoxy-phenyl) 4-[1-(toluene4-sulfonyl)-piperidin-3-ylmethyl]-piperazine.

Compounds of the invention are also 5-HT receptor agonists or antagonists, e.g. 5-$HT_1$ receptor agonists or antagonists including 5-$HT_{1A, B, C, D, E or F}$ receptors, and desirably 5-$HT_{1A}$ receptor agonists. Surprisingly, it has been found that compounds of the invention are very good 5-$HT_{1A}$ receptor agonists and have superior activity and selectivity compared to certain agonists on the market, e.g., BuSpar® (buspirone, Bristol-Myers Squibb.)

The compounds of the invention are more selective in their action, displaying no cross-reactivity with other receptors such as α-adrenergic receptors. Furthermore, these compounds are not only selective, but bind well to 5-HT1 receptors, e.g., 5-$HT_{1A}$ receptors, and are not rapidly metabolized to what are usually toxic metabolites. The compounds of the invention thus will have a longer half-life in vivo, e.g. wherein the compound is not metabolized or is only partially metabolized (HLM $T^{1/2}$>20-90 min., up to 100% of the compound remaining unchanged.) Applicants do not wish or intend to be limited to a particular theory of operation; however, compounds of Formula I where $R_1$ is cycloalkyl, e.g., cyclopropyl, cyclobutyl, cyclopentyl, cyclohexyl, cyclohexylmethyl, and cyclohexylphenyl; and $R_2$ is —$NR_4R_5$, where $R_4$ and $R_5$ are independently H, O or $COR_6$, where $R_6$ may be lower alkyl, e.g., nitro; NHCO-alkyl, e.g., NHCO-lower alkyl such as NHCO—$(C_2$-$C_4)$alkyl, including NHCO—$(CH_3)$, NHCO—$(CH_2CH_3)$, NHCO—$(CH_2CH_2$—$CH_3)$, and NHCO—$(CH(CH_2)_2)$ (i.e., cyclopropyl); NCO-dialkyl, are particularly good in this regard. As such, the utility of the compounds of the invention as, e.g., anti-anxiety agents, is greatly enhanced.

$R_1$ may be substituted or unsubstituted aryl, alkyl, cycloalkyl or alkylaryl, e.g., toluyl or cyclohexyl; $R_2$ may be lower alkyl, e.g., $C_1$-$C_4$; trihalomethyl, e.g., $CF_3$; halo, e.g., F, Br or Cl; a conjugated five- or six-membered cyclic or heterocyclic ring, e.g., 3,4-methylenedioxy; —$NR_4R_5$, where $R_4$ and $R_5$ are independently H, O or $COR_6$, where $R_6$ may be lower alkyl, e.g., nitro; NHCO-alkyl, e.g., NHCO-lower alkyl such as NHCO—$(C_2$-$C_4)$alkyl, including NHCO—$(CH_3)$, NHCO—$(CH_2CH_3)$, NHCO—$(CH_2CH_2$—$CH_3)$, and NHCO—$(CH(CH_2)_2)$ (i.e., cyclopropyl); NCO-dialkyl; sulfonamidoalkyl, e.g., sulfonamido$(C_2$-$C_4)$alkyl; the atoms denoted by the dotted line bond may, taken together, form a four, five, six or seven membered cyclic or heterocyclic ring; Z is N or C; m may be 0, 1 or 2; n may be 1, 2, 3, or 4; and p may be 0 or 1; and pharmaceutically acceptable salts and/or esters thereof. m is advantageously 0, n is advantageously 3 or 4, and p is advantageously 0 or 1.

In an embodiment, $R_1$ may be lower alkyl, e.g. n-butyl, s-butyl, i-butyl; p-toluene, p-halophenyl (e.g., p-fluorophenyl, p-chlorophenyl or p-bromophenyl), cycloalkyl, e.g., cyclopropyl, cyclobutyl, cyclopentyl, cyclohexyl, cyclohexylmethyl, and cyclohexylphenyl. Advantageously, $R_1$ may be cycloalkyl, e.g., cyclopropyl, cyclobutyl, cyclopentyl, cyclohexyl, cyclohexylmethyl, and cyclohexylphenyl. In this embodiment, $R_2$ may be aminoalkyl, e.g., amino(lower)alkyl such as aminomethyl, aminoethyl, aminopropyl, aminocyclopropyl, aminobutyl or dialkylamino. Advantageously, $R_2$ may be NHCO-alkyl, e.g., NHCO—$(C_2-C_4)$alkyl, including NHCO—$(CH_3)$, NHCO—$(CH_2CH_3)$, NHCO—$(CH_2CH_2$—$CH_3)$, and NHCO—$(CH(CH_2)_2$ (i.e., NHCO-cyclopropyl.)

The present invention relates to the discovery of new compounds for treating subjects method of treating a subject afflicted with a condition requiring treatment, by administering an effective amount of a compound of the invention to treat the condition(s). Various conditions will be responsive to the introduction of these compounds, alone and/or in combination with other drugs.

Another aspect of the invention includes methods for treating subjects suffering from various conditions that will be responsive to the introduction of these compounds; or altering physiological phenomena associated with certain conditions to achieve a desired treatment of said condition(s), alone and/or in combination with other drugs. Such conditions or physiological phenomena include vasodilation, smooth muscle contraction, bronchoconstriction, brain disorders such as vascular disorders, e.g., blood flow disorders caused by vasodilation and vasospastic diseases such as angina, vascular headache, migraine and Reynaud's disease; and neuropathological disorders including Parkinson's disease and Alzheimer's disease; modulation of the cardiovascular system; prophylaxis and control of the effects of occurrences of cerebral infarct (Apoplexia cerebri) such as stroke or cerebral ischemia; and for the control of disorders of the intestinal tract which are characterized by disturbances of the serotoninergic system and also by disturbances of the carbohydrate metabolism; stress-related somatic disorders; reflex sympathetic dystrophy such as shoulder/hand syndrome; disorders of bladder function such as cystitis, bladder detrusor hyper-reflexia and incontinence; and pain or nociception attributable to or associated with any of the foregoing conditions, especially pain transmission in migraine.

The invention is also drawn to methods of treating conditions associated with serotonergic hypofunction or hyperfunction, including administering a compound of the invention to a subject to treat the condition. As explained above, compounds of the invention can have antagonistic activity at 5-$HT_{1A}$ receptors, which will counteract the negative feedback mechanism induced by the inhibition of serotonin reuptake; this is thereby expected to improve the effect of the serotonin reuptake inhibiting activity of the compounds of the invention. Other compounds of the invention have agonistic activity at 5-HT receptors like 5-$HT_{1A}$.

Another aspect of the invention is a pharmaceutical composition comprising an amount of a compound according to Formula I or II effective to treat anxiety, particularly generalized anxiety disorder, in a mammal suffering therefrom, and a pharmaceutically acceptable carrier.

Another aspect of the invention is a method for treating anxiety, particularly generalized anxiety disorder, in a mammal such as a human comprising administering a therapeutically effective amount of a compound according to Formula I or II.

Another aspect of the invention is a pharmaceutical composition comprising an amount of a compound according to Formula I or II effective to treat panic disorder in a mammal suffering therefrom, and a pharmaceutically acceptable carrier.

Another aspect of the invention is a method for treating panic disorder in a mammal such as a human comprising administering a therapeutically effective amount of a compound according to Formula I or II.

Another aspect of the invention is a pharmaceutical composition comprising an amount of a compound according to Formula I or II effective to treat attention deficit disorder (ADD), with or without hyperactivity, i.e., ADHD, in a mammal suffering therefrom, and a pharmaceutically acceptable carrier.

Another aspect of the invention is a method for treating attention deficit disorder, with or without hyperactivity, in a mammal such as a human comprising administering a therapeutically effective amount of a compound according to Formula I or II.

Another aspect of the invention is a pharmaceutical composition comprising an amount of a compound according to Formula I or II effective to treat substance-related disorders in a mammal suffering therefrom, and a pharmaceutically acceptable carrier.

Another aspect of the invention is a method for treating substance-related disorders in a mammal such as a human comprising administering a therapeutically effective amount of a compound according to Formula I or II.

Another aspect of the invention is a pharmaceutical composition comprising an amount of a compound according to Formula I or II effective in treating conditions associated with vascular disorders, e.g., angina and migraine.

Another aspect of the invention is a method of treating conditions associated with vascular disorders, e.g., angina and migraine.

Processes for preparing the compounds and novel intermediates are also included in the invention.

The invention is also drawn to methods of treating conditions associated with serotonergic hypofunction or hyperfunction, including administering a compound of the invention to a subject to treat the condition. As explained above, compounds of the invention can have antagonistic activity at 5-$HT_{1A}$ receptors, which will counteract the negative feedback mechanism induced by the inhibition of serotonin reuptake; this is thereby expected to improve the effect of the serotonin reuptake inhibiting activity of the compounds of the invention. Other compounds of the invention have agonistic activity at 5-HT receptors like 5-$HT_{1A}$.

The compounds of the invention are valuable, alone and/or in combination with other drugs, for treating a wide variety of clinical conditions which are characterized by serotonin excess or absence, e.g., serotonergic hypofunction or hyperfunction. Such conditions include eating disorders, schizophrenia, neuralgia, and addiction disorders; obsessive compulsive disorders, panic disorders, sexual dysfunctions caused by the central nervous system and disturbances in sleep and the absorption of food, alcoholism, pain, memory deficits, unipolar depression, dysthymia, bipolar depression, treatment-resistant depression, depression in the medically ill, panic disorder, obsessive-compulsive disorder, eating disorders, social phobia, premenstrual dysphoric disorder, mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, e.g., specific animal phobias, social phobias, stress disorders including post-traumatic stress disorder and acute stress disorder, and generalized anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delirium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple etiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delirium, withdrawal delirium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and post-therapeutic neuralgia, trigeminal neuralgia, segmental or intercostal neuralgia and other neuralgias; and cerebral vascular disorders due to acute or chronic cerebrovascular damage such as cerebral infarction, subarachnoid hemorrhage or cerebral edema. In an embodiment, conditions characterized by serotonin excess or absence, (serotonergic hypofunction or hyperfunction) do not include depression.

Compounds of the invention may be used for the treatment of the above conditions, as well as for vasodilation, smooth muscle contraction, bronchoconstriction, brain disorders such as vascular disorders, e.g., blood flow disorders caused by vasodilation and vasospastic diseases such as angina, vascular headache, migraine and Reynaud's disease; and neuropathological disorders including Parkinson's disease and Alzheimer's disease; modulation of the cardiovascular system; prophylaxis and control of the effects of occurrences of cerebral infarct (*Apoplexia cerebri*) such as stroke or cerebral ischemia; and for the control of disorders of the intestinal tract which are characterized by disturbances of the serotoninergic system and also by disturbances of the carbohydrate metabolism.

The compounds may also be useful in treating a variety of other conditions including stress-related somatic disorders; reflex sympathetic dystrophy such as shoulder/hand syndrome; disorders of bladder function such as cystitis, bladder detrusor hyper-reflexia and incontinence; and pain or nociception attributable to or associated with any of the foregoing conditions, especially pain transmission in migraine.

For treating certain conditions it may be desirable to employ the compounds of the invention in conjunction with another pharmacologically active agent. The compounds of the invention may be presented together with another therapeutic agent as a combined preparation for simultaneous, separate or sequential use. Such combined preparations may be, for example, in the form of a twin pack.

A further aspect of the invention comprises compounds of the invention in combination with a or another 5-HT antagonist and/or SSRI, e.g., a $5\text{-HT}_3$ antagonist such as ondansetron, granisetron, tropisetron or zatisetron. Additionally, the compounds of the invention may be administered in combination with an anti-inflammatory corticosteroid, such as dexamethasone. Furthermore, the compounds of the invention may be administered in combination with a chemotherapeutic agent such as an alkylating agent, anti-metabolite, mitotic inhibitor or cytotoxic antibiotic, as described above. In general, the currently available dosage forms of the known therapeutic agents for use in such combinations will be suitable.

According to a further or alternative aspect, the invention provides compounds of the invention for use in the manufacture of a medicament for the treatment or prevention of conditions that will be responsive to the introduction of these compounds; or altering physiological phenomena associated with certain conditions to achieve a desired treatment of said condition(s), alone and/or in combination with other drugs. Such conditions or physiological phenomena include vasodilation, smooth muscle contraction, bronchoconstriction, brain disorders such as vascular disorders, e.g., blood flow disorders caused by vasodilation and vasospastic diseases such as angina, vascular headache, migraine and Reynaud's disease; and neuropathological disorders including Parkinson's disease and Alzheimer's disease; modulation of the cardiovascular system; prophylaxis and control of the effects of occurrences of cerebral infarct (*Apoplexia cerebri*) such as stroke or cerebral ischemia; and for the control of disorders of the intestinal tract which are characterized by disturbances of the serotoninergic system and also by disturbances of the carbohydrate metabolism; stress-related somatic disorders; reflex sympathetic dystrophy such as shoulder/hand syndrome; disorders of bladder function such as cystitis, bladder detrusor hyper-reflexia and incontinence; and pain or nociception attributable to or associated with any of the foregoing conditions, especially pain transmission in migraine.

According to a further or alternative aspect, the invention provides compounds of the invention for use in the manufacture of a medicament for the treatment or prevention of physiological disorders associated with serotonin excess or absence, e.g. serotonergic hypofunction or hyperfunction.

The invention also provides methods for treating or preventing physiological disorders associated with serotonin excess or absence, e.g., serotonergic hypofunction or hyperfunction, which method comprises administration to a patient in need thereof of an effective amount of a compound of the invention or a composition comprising a compound of the invention.

For treating or preventing migraine, the compounds of the invention may be used in conjunction with other anti-migraine agents, such as ergotamines or $5\text{-HT}_1$ agonists, especially sumatriptan or rizatriptan. Likewise, for treating behavioral hyperalgesia, the compounds of the invention may be used in conjunction with an antagonist of N-methyl D-aspartate (NMDA), such as dizocilpine.

It will be further appreciated that for treating or preventing anxiety and/or depression, the compounds of the invention may be used in combination with an antidepressant agent or anti-anxiety agent. Suitable classes of antidepressant agents of use in the invention include: norepinephrine reuptake inhibitors, selective serotonin reuptake inhibitors, monoamine oxidase inhibitors, reversible monoamine oxidase inhibitors, serotonin and noradrenaline reuptake inhibitors, corticotropin releasing factor (CRF) antagonists, β-adrenoreceptor antagonists and atypical antidepressants. Another class of antidepressant agent of use in the invention is noradrenergic and specific serotonergic antidepressants, such as mirtazapine. Suitable examples of norepinephrine reuptake inhibitors include amitripdyline, clomipramine, doxepine, imipramine, trimipramine, amoxapine, desipramine, maprotiline, nortriptyline, reboxetine and protriptyline and pharmaceutically acceptable salts thereof. Suitable examples of selective serotonin reuptake inhibitors include fluoxetine, fluvoxamine, paroxetine, and sertraline and pharmaceutically acceptable salts thereof. Suitable examples of monoamine oxidase inhibitors include isocarboxazid, phenelzine, tranylcypromain and selegiline, and pharmaceutically acceptable salts thereof. Suitable examples of reversible monoamine oxidase inhibitors include moclobemide, and pharmaceutically acceptable salts thereof. Suitable examples of serotonin and noradrenaline reuptake inhibitors include venlafaxine, and pharmaceutically acceptable salts thereof. Suitable examples of corticotropin releasing factor (CRF) antagonists include those compounds described in International Patent Specification Nos. WO 94/13643, WO 94/13644, WO 94/13661, WO 94/13676 and WO 94/13677. Suitable examples of atypical antidepressants include bupropion, lithium, nefazoedone, sibutramine, trazodone and viloxazine, and pharmaceutically acceptable salts thereof. Other antidepressants of use in the invention include adinozolam, alaproclate, amineptine, amitryptyline/chlordiazepoxide combination, atipamezole, azamianserin, bazinaprine, fefuraline, bifemelane, binodaline, bipenamol, brofaromine, bupropion, caroxazone, cericlamine, cianopramine, cimoxatone, citalopram, clemeprol, clovoxamine, dasepinil, deanol, demexiptiline, dibenzepin, dothiepin, droxidopa, enefexine, setazolam, etoperidone, femoxetine, fengabine, fezolamine, fluotracen, idazoxan, indalpine, indeloxazine, iprindole, levoprotiline, litoxetine, lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirindole, pizotyline, ritaserin, rolipram, sercloremine, setiptiline, sibutramine, sulbutiamine, sulpride, teniloxazine, thozalinone, thymoliberin, tianeptine, tiflucarbine, tofenacin, tofisopam, toloxatone, tomoxetine, veralipride, viqualine, zimelidine, and zometapine, and pharmaceutically acceptable salts thereof, and St. John's wort herb, or *Hypericum perforatum*, or extracts thereof. Preferred antidepressant agents include selective serotonin reuptake inhibitors, in particular, fluoxetine, fluvoxamine, paroxetine, and sertraline and pharmaceutically acceptable salts thereof.

Suitable classes of anti-anxiety agents of use in the invention include benzodiazepines and 5-$HT_{1A}$ agonists or antagonists, especially 5-$HT_{1A}$ partial agonists, and corticotropin releasing factor (CRF) antagonists. In addition to benzodiazepines, other suitable classes of anti-anxiety agents are non-benzodiazepine sedative-hypnotic drugs such as zolpidem; mood-stabilizing drugs such as clobazam, gabapentin, lamotrigine, loreclezole, oxcarbamazepine, stiripentol and vigabatrin; and barbiturates. Suitable benzodiazepines of use in the invention include alprazolam, chlordizepoxide, clonazepam, chlorazepate, diazepam, halazepam, lorezepam, oxazepam and prazepam, and pharmaceutically acceptable salts thereof. Suitable examples of 5-$HT_{1A}$ agonists or antagonists of use in the invention include, in particular, the 5-$HT_{1A}$ partial agonists buspirone, flesinoxan, gepirone, ipsapirone and pindolol, and pharmaceutically acceptable salts thereof. Another class of anti-anxiety agent of use in the invention are compounds having muscarinic cholinergic activity. Suitable compounds in this class include m1 muscarinic cholinergic receptor antagonists such as those compounds described in European Patent Specification Nos. 0 709 093, 0 709 094 and 0 773 021 and International Patent Specification No. WO 96/12711. Another class of anti-anxiety agent of use in the invention are compounds acting on ion channels. Suitable compounds in this class include carbamazepine, lamotrigine and valproate, and pharmaceutically acceptable salts thereof.

Therefore, in a further aspect of the invention, a pharmaceutical composition is provided comprising a compound of the invention and an antidepressant or an anti-anxiety agent, together with at least one pharmaceutically acceptable carrier or excipient.

Suitable antipsychotic agents of use in combination with the compounds of the invention include phenothiazines, e.g., chlorpromazine, mesoridazine, thioridazine, acetophenazine, fluphenazine, perphenazine and trifluoperazine; thioxanthenes, e.g., chlorprothixene or thiothixene; heterocyclic dibenzazepines, e.g., clozapine or olanzapine; butyrophenones, e.g., haloperidol; diphenylbutylpiperidines, e.g., pimozide; and indolones, e.g., molindolene. Other antipsychotic agents include loxapine, sulpiride and risperidone. It will be appreciated that the antipsychotic agents when used in combination with the compounds of the invention may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with the compounds of the invention include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with the compounds of the invention is the 5-$HT_{2A}$ receptor antagonists, examples of which include MDL100907 and fananserin. Also of use in combination with the compound of the invention are the serotonin dopamine antagonists (SDAs) which are believed to combine 5-$HT_{2A}$ and dopamine receptor antagonist activity, examples of which include olanzapine and ziperasidone.

Therefore, in a further aspect of the invention, a pharmaceutical composition is provided comprising a compound of the invention and an antipsychotic agent, together with at least one pharmaceutically acceptable carrier or excipient.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The invention also relates to the use of such compounds in the treatment of Attention Deficit Hyperactivity Disorder (ADHD). ADHD, with or without hyperactivity (also referred to in the literature as Attention Deficit Disorder/Hyperactivity Syndrome (ADD/HS)), is a condition (or group of conditions) characterized by impulsiveness, distractibility, inappropriate behavior in social situations and hyperactivity. ADD/HS is reported to have a prevalence of 3-5% (using DSM-IV criteria) in children. It is believed that some 30-60% of such cases persist into adulthood. This disorder can impair social function, learning and/or development and is therefore now recognized as a serious problem. It is further recognized that many children with ADHD go on to develop other co-morbid conditions or social problems in adulthood.

In clinical terms, ADHD is diagnosed if any one of the three main clinical features—inattention, over-activity and impulsiveness—persists in two or more situations, e.g., in both a home and school environment (American Psychiatric Association. Diagnostic and Statistical Manual of Mental Disorders, Fourth Edition (DSM-IV) Washington D.C.; American Psychiatric Association, 1994).

A particularly severe form of ADHD is termed Hyperkinetic Disorder. This diagnosis may be made if all three of the main clinical features (inattention, over-activity and impulsiveness) have been present from an early age, persist in more than one situation (e.g., home and school) and impair function (The ICD-10 Classification of Mental and Behavioural Disorders: Diagnostic Criteria for Research. Geneva: World Health Organization, 1993: 155-7). Reports indicate that 1 in 200 children suffer from hyperkinetic disorder.

There are currently only a few therapeutic agents which are recognized as having efficacy in the treatment of childhood ADHD; at present the drugs of choice include dextroamphetamine, pemoline, and in particular methylphenidate (Ritalin®). Antidepressants and antipsychotic medications such as risperidone may also be effective in some cases, but these are not standard treatments. Although methylphenidate is probably the most widely used drug in the treatment of ADHD, it suffers from a number of disadvantages: it is a controlled drug: is extensively metabolized and may cause confusion and hallucinations. Moreover, methylphenidate does not treat one of the three main clinical features of ADHD, namely inattentiveness, and in addition does not normalize ADHD children.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of a condition associated with a serotonin excess or absence, e.g., serotonergic hypofunction or hyperfunction, an appropriate dosage level will generally be about 0.001 to 50 mg/kg patient body weight per day, which may be administered in single or multiple doses. If given orally, the dosage level may be about 0.01 to about 30 mg/kg per day, e.g., 0.01 to about 1, 3, 5, 7, 10, 15, 20, 25 or 30 mg/kg per day.

If given intravenously, the dosage levels may be somewhat lower, e.g., 0.01 to about 0.3, 1, 3, 5, 7 or 10 mg/kg per day. For example, in the treatment or prevention of a disorder of the central nervous system, a suitable oral dosage level may be about 0.01 to about 30 mg/kg per day, e.g., 0.01 to about 1, 3, 5, 7, 10, 15, 20, 25 or 30 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the peptides of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The compositions and combination therapies of the invention will then generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermolysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to. proteolysis by digestive enzymes. Such compounds are contemplated to include chemically designed or modified agents; dextrorotatory peptides; and peptide and liposomal formulations in time release capsules to avoid peptidase and lipase degradation.

Pharmaceutically acceptable salts include acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabensas preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrastemal injection or infusion techniques.

Methods for preparing the compounds of this invention are illustrated in the following Example(s). The following examples are given for the purpose of illustrating the invention, but not for limiting the scope or spirit of the invention.

Synthesis of Arylpiperazinyl Sulfonamide Compounds

Arylpiperazinyl sulfonamide compounds of the invention were synthesized by the following schemes.

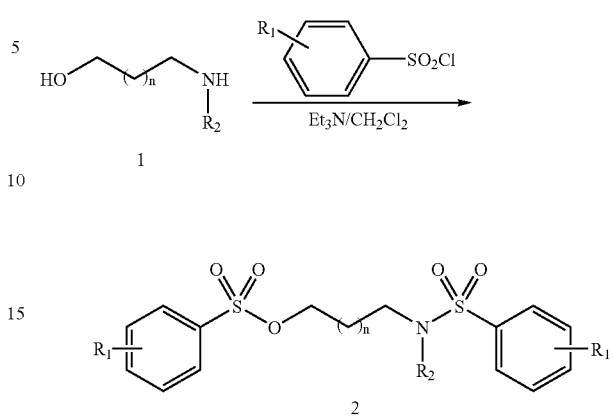

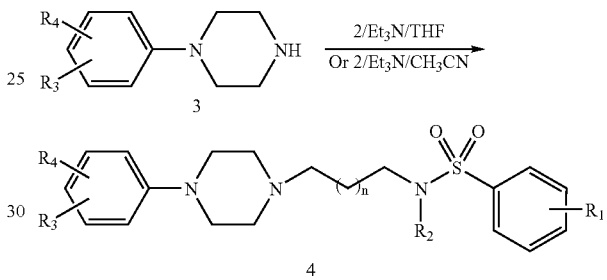

$R_1 = CH_3, CH_3CH_2, F$
$R_2 = H, CH_3, CH_3CH_2, CH_3CH_2CH_2, c\text{-}C_3H_5$
$R_3, R_4 = NO_2, CH_3O, CH_3CH_2O, CH_3, CH_3CH_2, CH_3CH_2CH_2, CH_3CH_2CH_2CH_2, (CH_3)_2CH, H$

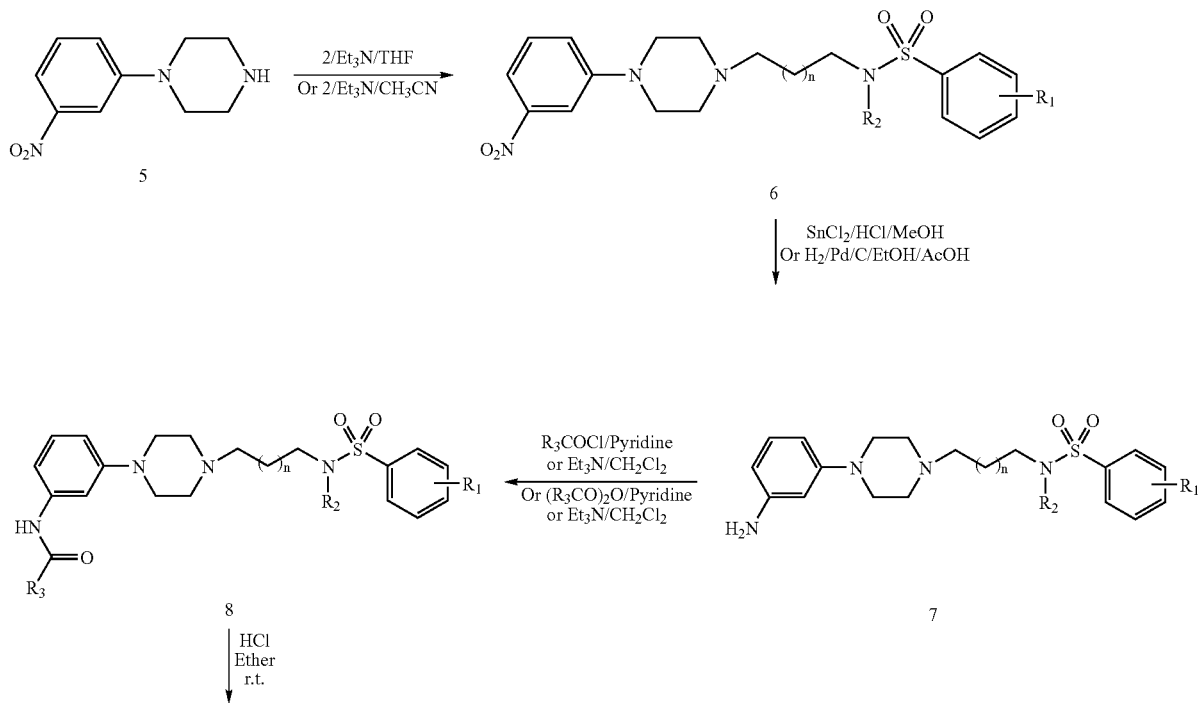

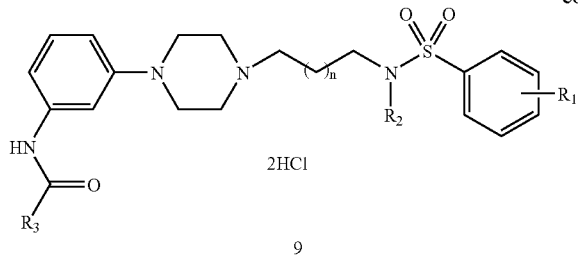
2HCl
9
$R_1$ = $CH_3$, $CH_3CH_2$, F
$R_2$ = H, $CH_3$, $CH_3CH_2$, $CH_3CH_2CH_2$, $CH_3CH_2CH_2CH_2$, $(CH_3)_3C$, $(CH_3)_2CH$, c-$C_3H_5$, c-$C_4H_7$, c-$C_5H_9$, c-$C_6H_{11}$, c-$C_6H_{11}CH_2$
$R_3$ = $CH_3$, $CH_3CH_2$, $CH_3CH_2CH_2$, $CH_3CH_2CH_2CH_2$, $(CH_3)_3C$, $(CH_3)_2CH$, c-$C_3H_5$, c-$C_4H_7$, c-$C_5H_9$, c-$C_6H_{11}$, c-$C_6H_{11}CH_2$
SCHEME 3
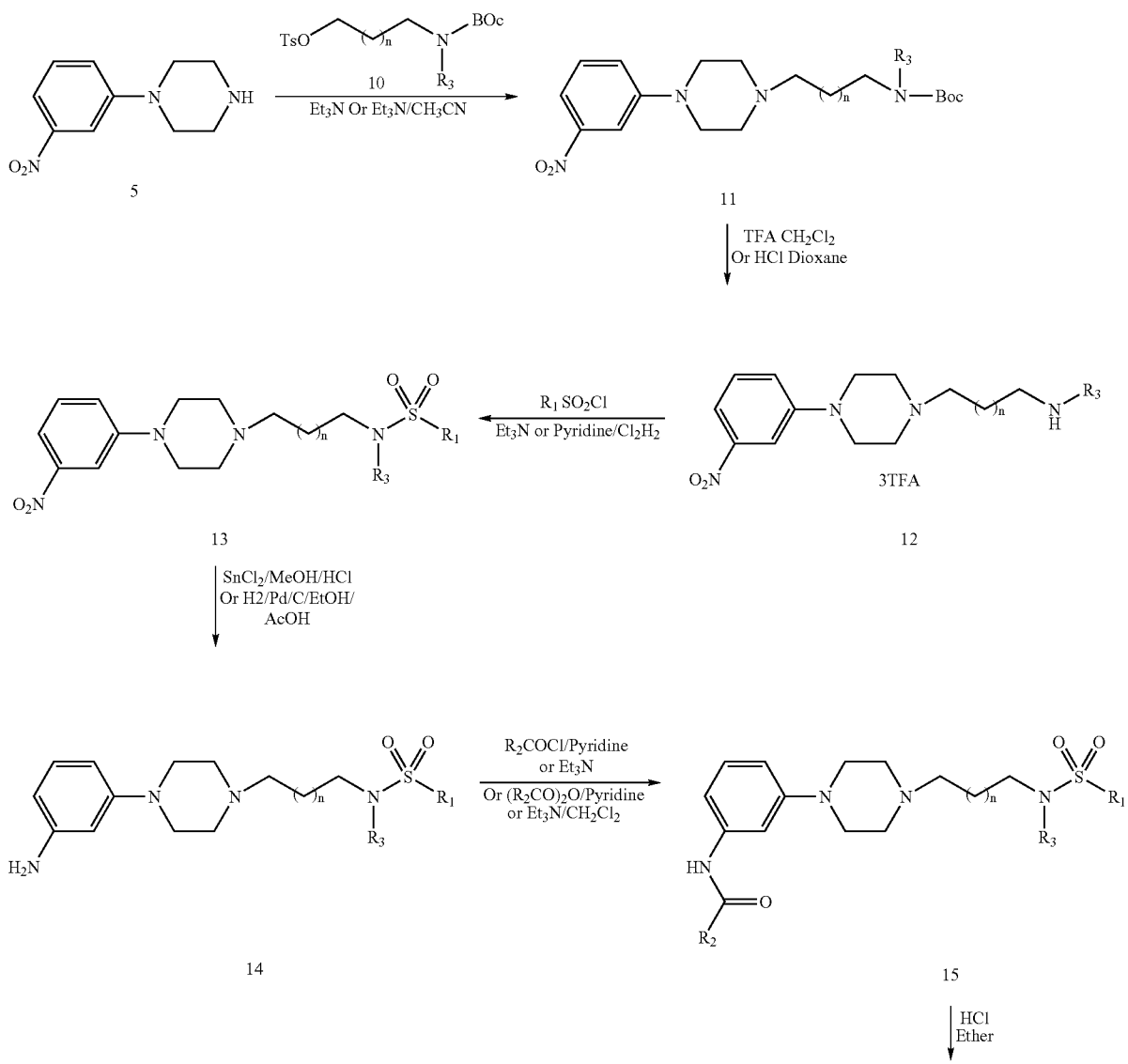

-continued

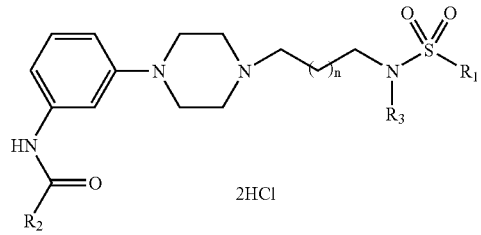

2HCl

16

R$_1$, R$_2$ = CH$_3$, CH$_3$CH$_2$, CH$_3$CH$_2$CH$_2$, CH$_3$CH$_2$CH$_2$CH$_2$, (CH$_3$)$_2$CH, (CH$_3$)$_2$CHCH$_2$, (CH$_3$)$_3$C, c-C$_6$H$_{11}$CH$_2$, c-C$_6$H$_{11}$, c-C$_5$H$_9$, c-C$_4$H$_7$, c-C$_3$H$_5$,
R$_3$ = H, CH$_3$, CH$_3$CH$_2$, CH$_3$CH$_2$CH$_2$, CH$_3$CH$_2$CH$_2$CH$_2$, (CH$_3$)$_2$CH, (CH$_3$)$_2$CHCH$_2$, (CH$_3$)$_3$C, c-C$_6$H$_{11}$CH$_2$, c-C$_6$H$_{11}$, c-C$_5$H$_9$, c-C$_4$H$_7$, c-C$_3$H$_5$

SCHEME 4

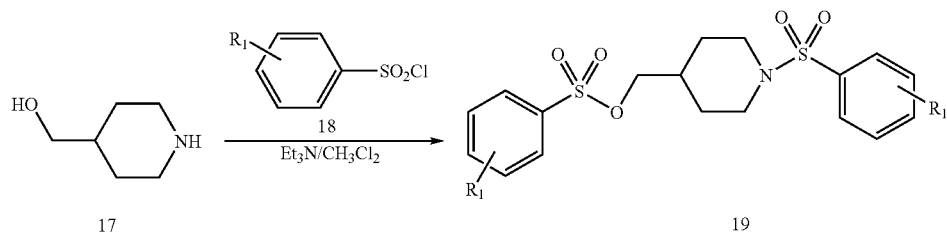

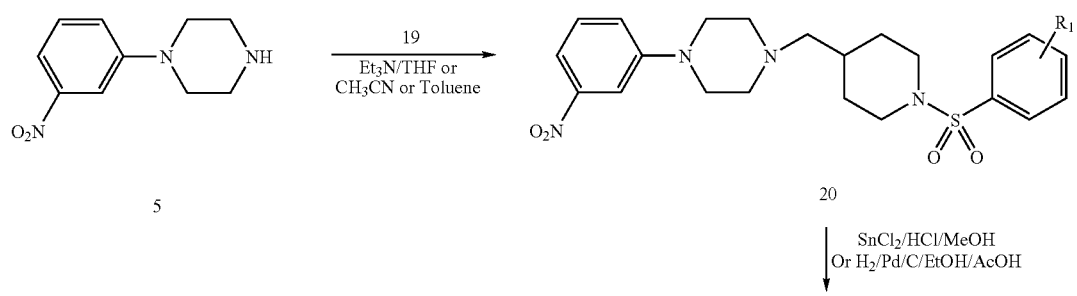

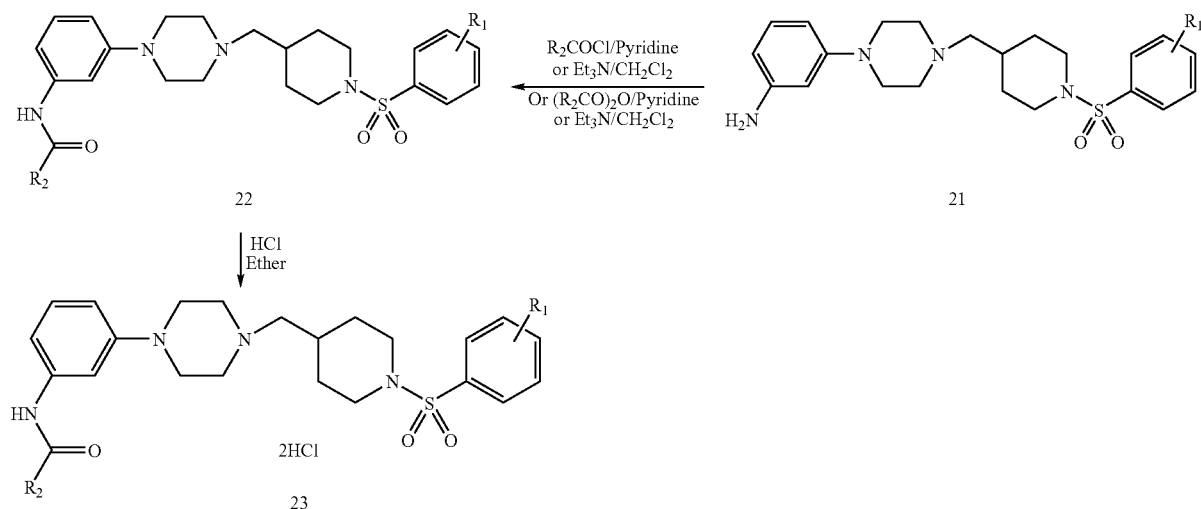

R$_1$ = CH$_3$, CH$_3$CH$_2$, F
R$_2$ = CH$_3$, CH$_2$CH$_3$, CH$_3$CH$_2$CH$_2$, CH$_3$CH$_2$CH$_2$CH$_2$, (CH$_3$)$_2$CH, (CH$_3$)$_3$C, (CH$_3$)$_2$CHCH$_2$, c-C$_3$H$_5$

SCHEME 5
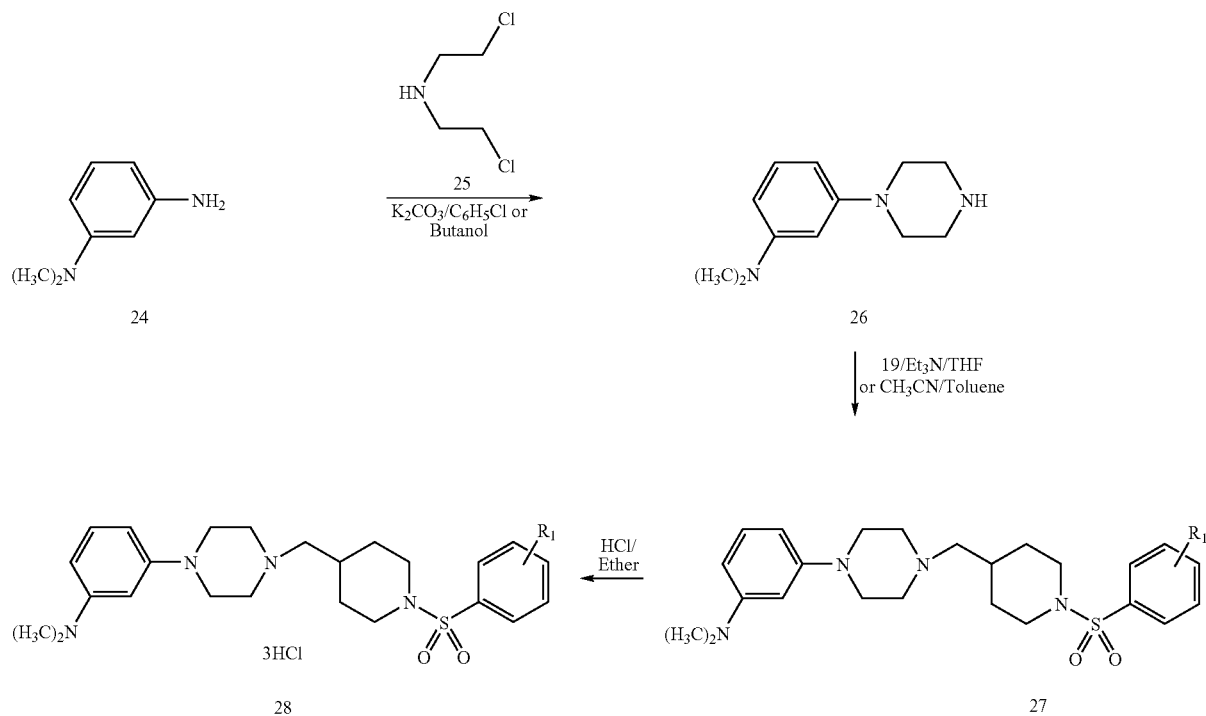
SCHEME 6
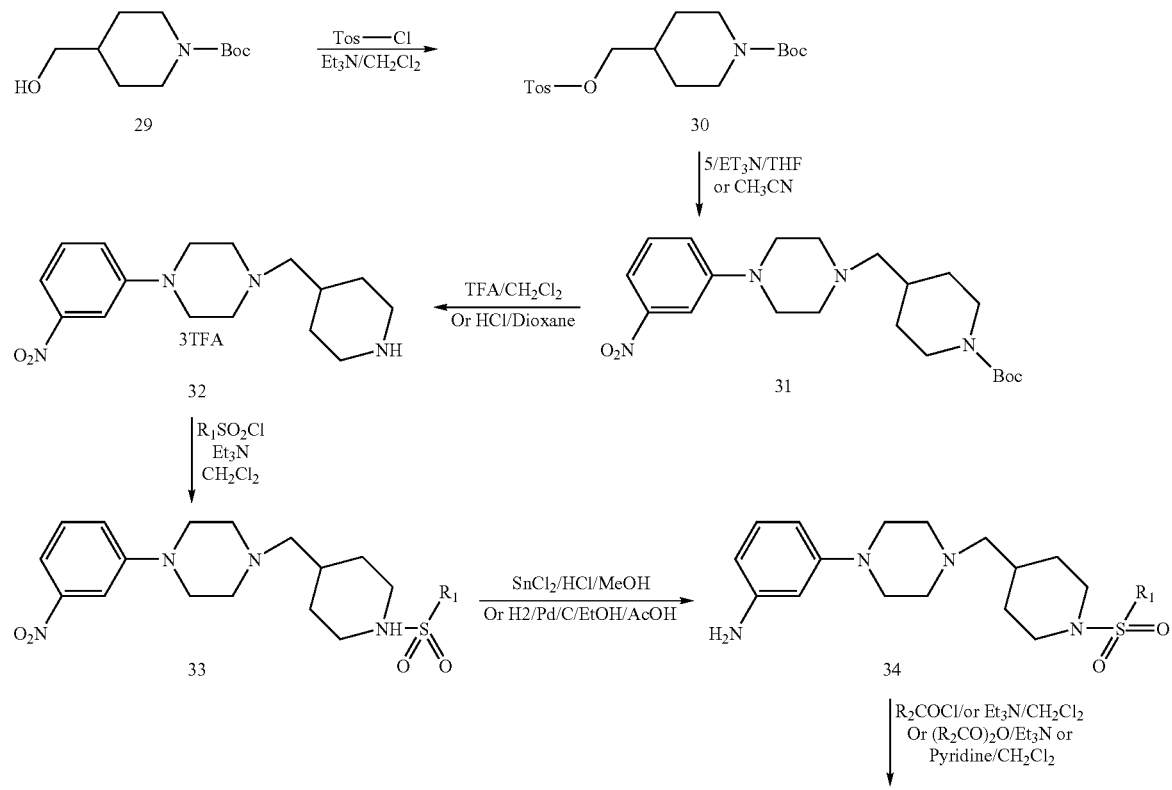

37      38
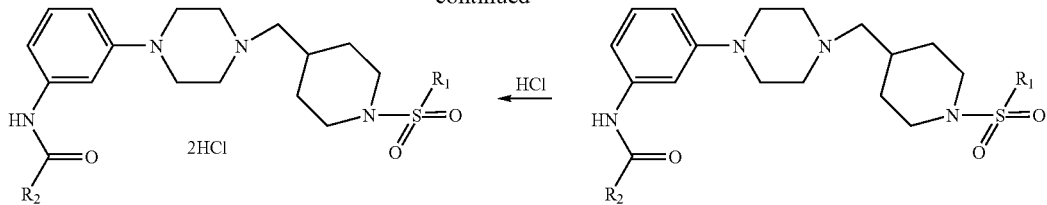
$R_1, R_2 = CH_3, CH_3CH_2, CH_3CH_2CH_2, CH_3CH_2CH_2CH_2, (CH_3)_2CH, (CH_3)_2CHCH_2, (CH_3)_3C, c\text{-}C_6H_{11}CH_2, c\text{-}C_6H_{11}, c\text{-}C_5H_9, c\text{-}C_4H_7, c\text{-}C_3H_5,$
SCHEME 7
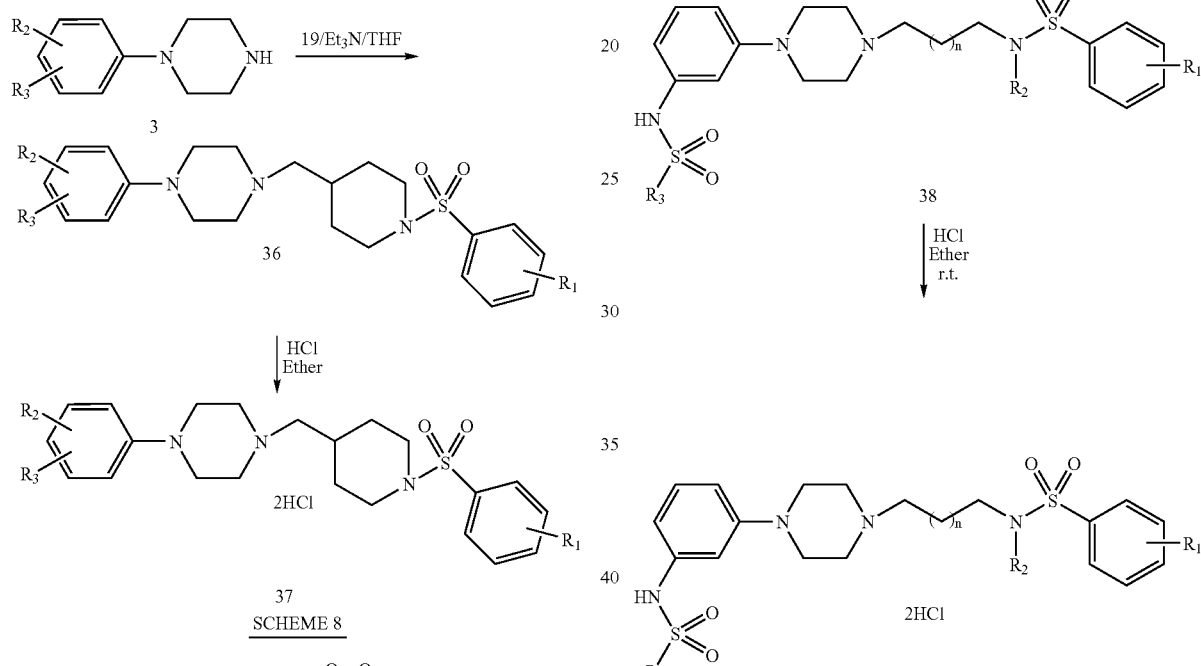
SCHEME 8
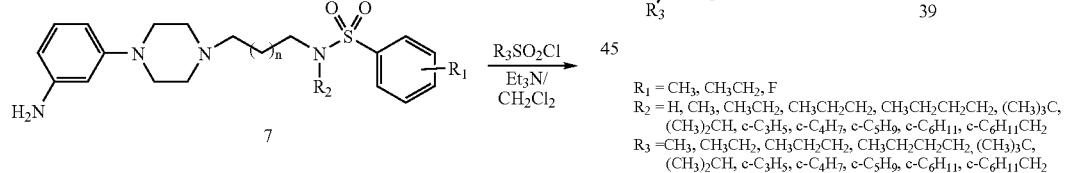
$R_1 = CH_3, CH_3CH_2, F$
$R_2 = H, CH_3, CH_3CH_2, CH_3CH_2CH_2, CH_3CH_2CH_2CH_2, (CH_3)_3C,$
$\quad (CH_3)_2CH, c\text{-}C_3H_5, c\text{-}C_4H_7, c\text{-}C_5H_9, c\text{-}C_6H_{11}, c\text{-}C_6H_{11}CH_2$
$R_3 = CH_3, CH_3CH_2, CH_3CH_2CH_2, CH_3CH_2CH_2CH_2, (CH_3)_3C,$
$\quad (CH_3)_2CH, c\text{-}C_3H_5, c\text{-}C_4H_7, c\text{-}C_5H_9, c\text{-}C_6H_{11}, c\text{-}C_6H_{11}CH_2$
SCHEME 9
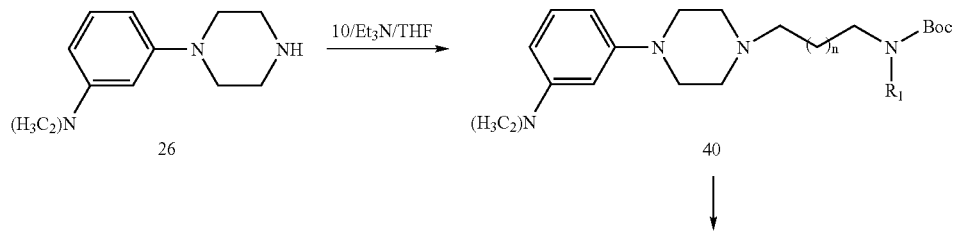

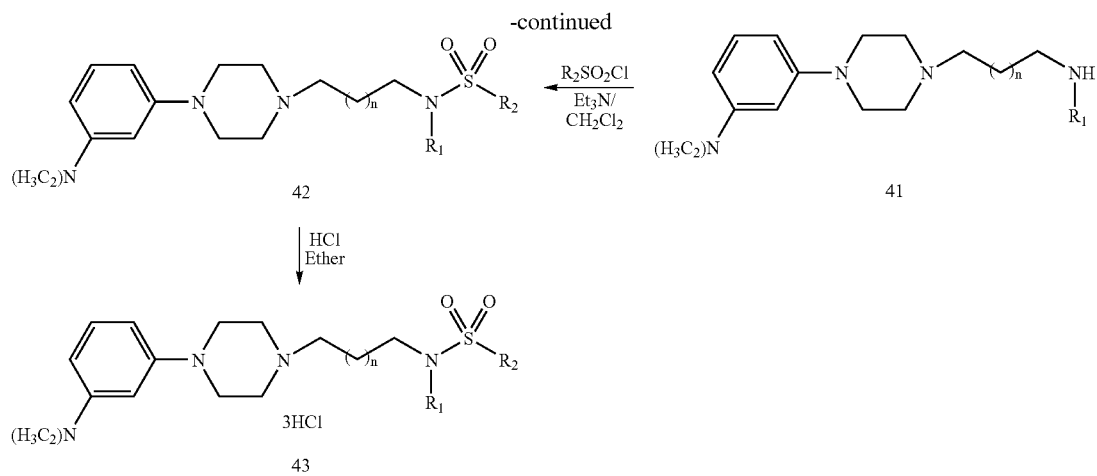

$R_1$ =CH$_3$, CH$_3$CH$_2$, CH$_3$CH$_2$CH$_2$, CH$_3$CH$_2$CH$_2$CH$_2$, (CH$_3$)$_2$CH, (CH$_3$)$_2$CHCH$_2$, (CH$_3$)$_3$C, c-C$_6$H$_{11}$CH$_2$, c-C$_6$H$_{11}$, c-C$_5$H$_9$, c-C$_4$H$_7$, c-C$_3$H$_5$,
$R_2$ = H, CH$_3$, CH$_3$CH$_2$, CH$_3$CH$_2$CH$_2$, CH$_3$CH$_2$CH$_2$CH$_2$, (CH$_3$)$_2$CH (CH$_3$)$_2$CHCH$_2$, (CH$_3$)$_3$C, c-C$_6$H$_{11}$CH$_2$, c-C$_6$H$_{11}$, c-C$_5$H$_9$, c-C$_4$H$_7$, c-C$_3$H$_5$,

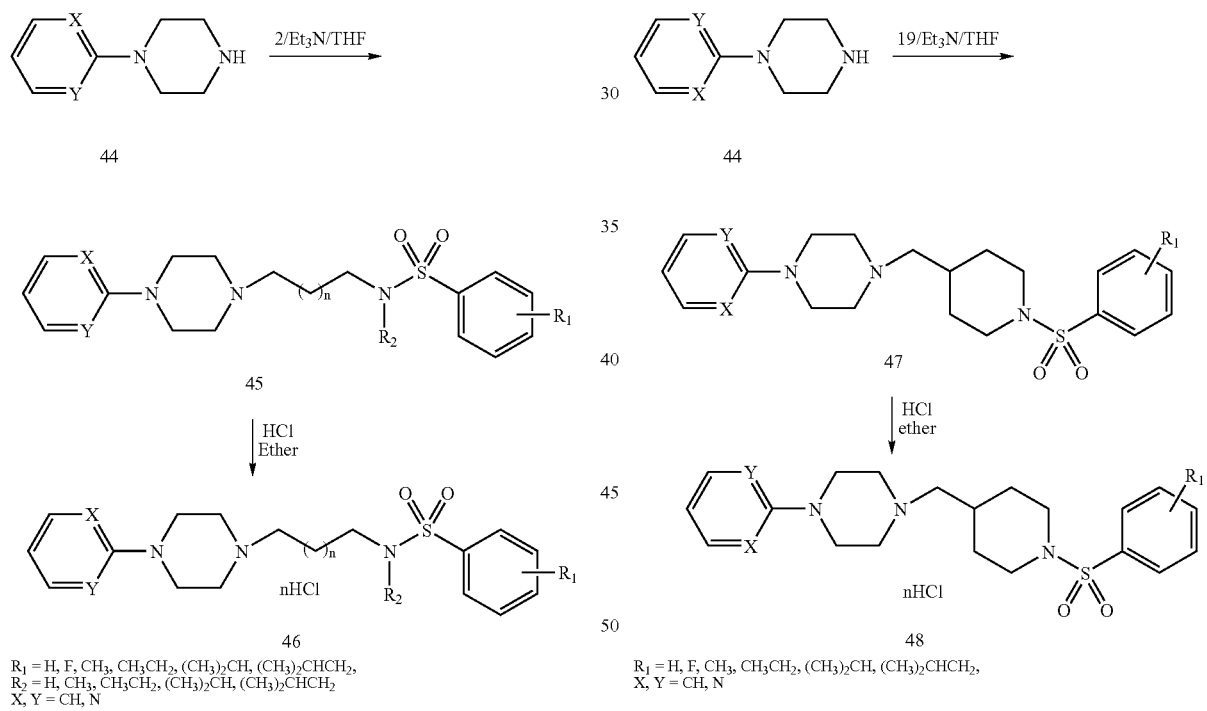

$R_1$ = H, F, CH$_3$, CH$_3$CH$_2$, (CH$_3$)$_2$CH, (CH$_3$)$_2$CHCH$_2$,
$R_2$ = H, CH$_3$, CH$_3$CH$_2$, (CH$_3$)$_2$CH, (CH$_3$)$_2$CHCH$_2$
X, Y = CH, N $R_1$ = H, F, CH$_3$, CH$_3$CH$_2$, (CH$_3$)$_2$CH, (CH$_3$)$_2$CHCH$_2$,
X, Y = CH, N

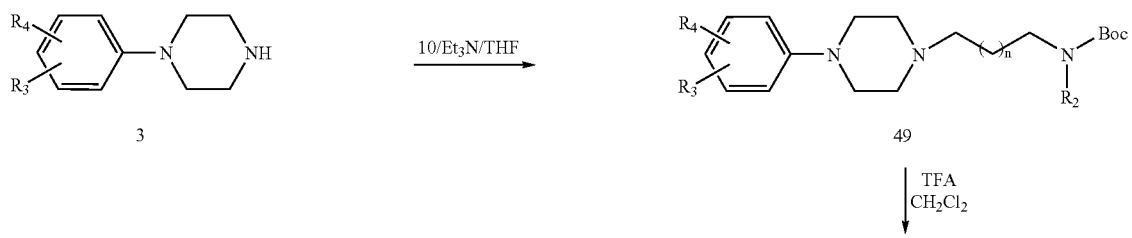

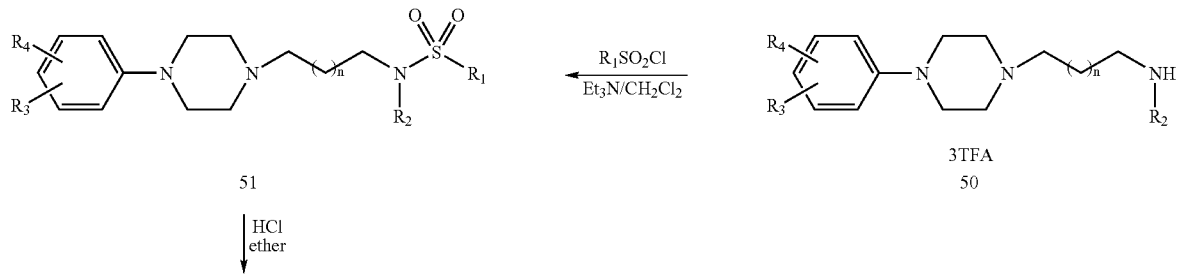

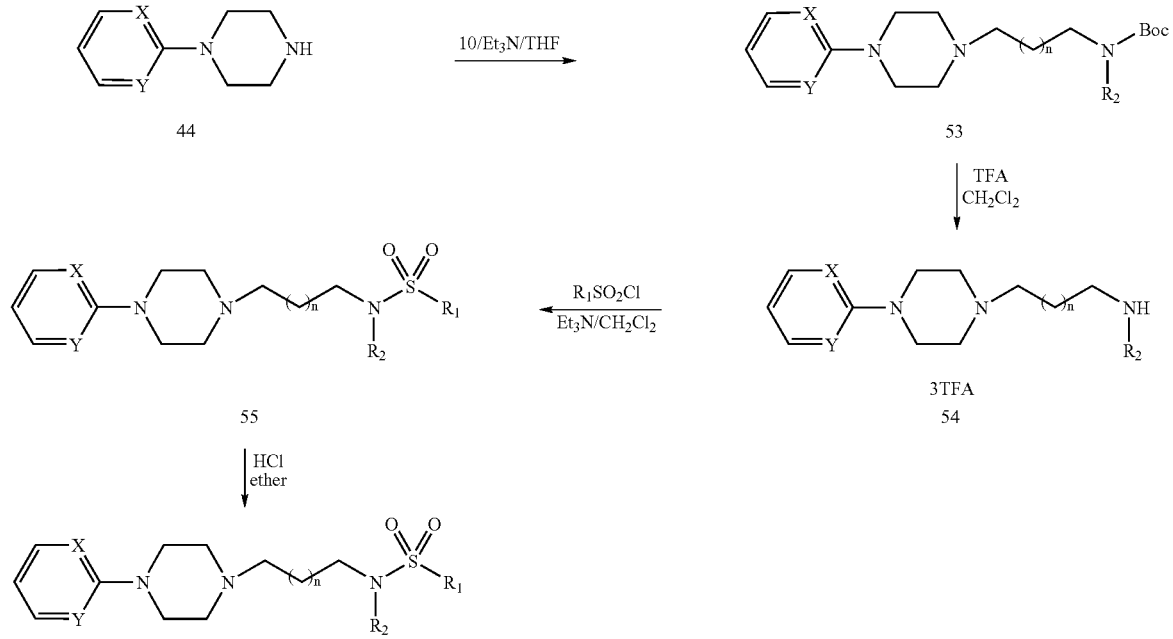

SCHEME 13

$R_1$ = CH$_3$, CH$_3$CH$_2$, CH$_3$CH$_2$CH$_2$, CH$_3$CH$_2$CH$_2$CH$_2$, (CH$_3$)$_2$CH, (CH$_3$)$_2$CHCH$_2$, (CH$_3$)$_3$C, c-C$_6$H$_{11}$CH$_2$, c-C$_6$H$_{11}$, c-C$_5$H$_9$, c-C$_4$H$_7$, c-C$_3$H$_5$, $R_2$ = H, CH$_3$, CH$_3$CH$_2$, CH$_3$CH$_2$CH$_2$, CH$_3$CH$_2$CH$_2$CH$_2$, (CH$_3$)$_2$CH, (CH$_3$)$_2$CHCH$_2$, (CH$_3$)$_3$C, c-C$_6$H$_{11}$CH$_2$, c-C$_6$H$_{11}$, c-C$_5$H$_9$, c-C$_4$H$_7$, c-C$_3$H$_5$, $R_3$, $R_4$ = NO$_2$, CH$_3$O, CH$_3$CH$_2$O, CH$_3$, CH$_3$CH$_2$, CH$_3$CH$_2$CH$_2$, CH$_3$CH$_2$CH$_2$CH$_2$, (CH$_3$)$_3$C, (CH$_3$)$_2$CH, H, $R_1$ = CH$_3$, CH$_3$CH$_2$, CH$_3$CH$_2$CH$_2$, CH$_3$CH$_2$CH$_2$CH$_2$, (CH$_3$)$_2$CH, (CH$_3$)$_2$CHCH$_2$, (CH$_3$)$_3$C, c-C$_6$H$_{11}$CH$_2$, c-C$_6$H$_{11}$, c-C$_5$H$_9$, c-C$_4$H$_7$, c-C$_3$H$_5$, $R_2$ = H, CH$_3$, CH$_3$CH$_2$, CH$_3$CH$_2$CH$_2$, CH$_3$CH$_2$CH$_2$CH$_2$, (CH$_3$)$_2$CH, (CH$_3$)$_2$CHCH$_2$, (CH$_3$)$_3$C, c-C$_6$H$_{11}$CH$_2$, c-C$_6$H$_{11}$, c-C$_5$H$_9$, c-C$_4$H$_7$, c-C$_3$H$_5$,

X, Y = CH, N

Preparation 1

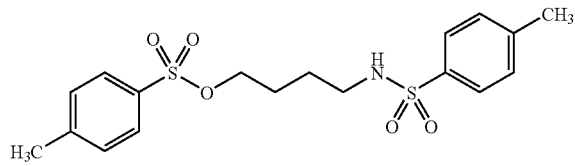

To an ice-cooled solution of amino alcohol 1 (1.0 g, 11.0 mmol) in anhydrous methylene chloride (25 mL) under $N_2$ was added $Et_3N$ (6.1 mL, 44.0 mmol), followed by tosyl chloride (5.3 g, 28.0 mmol). The mixture was stirred at 0° C. for 3 h and then quenched with cold aqueous saturated $NaHCO_3$ solution (15 mL), and the organic phase was washed with water (3×15 mL). The organic layer was dried over $MgSO_4$ and filtered, and the solvent was removed under reduced pressure to give a brownish-red residue. The crude material was used for next step without further purification.

EXAMPLE 1

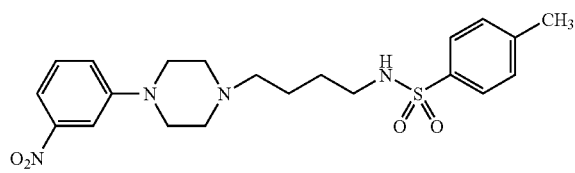

A mixture of 1-(3-nitro-phenyl)-piperazine (3.4 g, 16.4 mmol); the product of Preparation 1, 4-(tosylamino)butyl 4-methylbenzenesulfonate; (7.8 g, 19.6 mmol); triethyl amine (2.4 g, 23.7 mmol) in THF or $CH_3CN$ (500 ml) was stirred under nitrogen at ambient temperature for 48 hours. The reaction mixture was diluted with dichloromethane and washed with 10% aqueous sodium carbonate solution (2×200 ml) and water (2×200 ml), dried over sodium sulfate. After removal of sodium sulfate, solvent was evaporated under reduced pressure. The residue was purified by flash chromatography on silica gel using dichloromethane-methanol (100:2) as an eluent to give 5.4 g (76% yield) of the title compound, 4-Methyl-N-{4-[4-(3-nitro-phenyl)-piperazin-1-yl]-butyl}-benzenesulfonamide.

$^1$H NMR (400 MHz, $CDCl_3$): δ (ppm), 7.74 7.66 (m, 4H), 7.40 (t, 1H), 7.29 (d, 2H), 7.22-7.20 (m, 1H), 3.34-3.2 (m, 4H), 2.99 (t, 1H), 2.63-2.61 (m, 4H), 2.42 (s, 3H), 2.39 (t, 2H), 1.61-1.59 (m, 4H); MS (APCI): m/z 433 (MH$^+$; 100%).

EXAMPLE 2

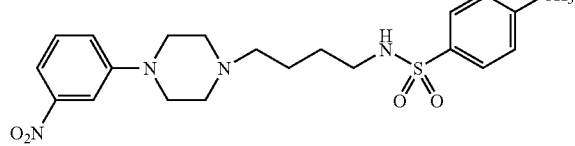

2HCl

To a solution of the product of Example 1 (150 mg, 0.35 mmol) in dichloromethane (0.5 ml) at ambient temperature was added 2 ml of 2M hydrochloride ether solution. The precipitate was collected by filtration, washed with ether and dried under vacuum overnight to give the salt of the product of Example 1, a white solid product (168 mg, 95% yield).

$^1$H NMR (400 MHz, $CD_3OD$): δ (ppm), 7.83(s, 1H), 7.76-7.72(m, 3H), 7.51(t, 1H), 7.44-7.38(m, 3H), 4.00(d, 2H), 3.69(m, 2H), 3.30-3.15(m, 6H), 2.90(t, 2H), 2.42(s, 3H), 1.88(m, 2H), 1.59(m, 2H); MS (APCI): m/z 433 (MH$^+$; 100%)

Preparation 2

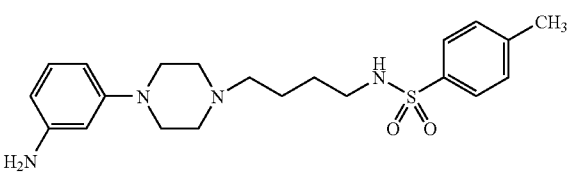

To a solution of tin chloride (3.5 g, 18.5 mmol) in methanol (50 ml) and concentrated hydrochloride (10 ml) was added a solution of the product of Example 1 (800 mg, 1.85 mmol) in methanol (50 ml) in one portion at −10° C. The reaction mixture was allowed to warm to ambient temperature and stirred until the reaction was complete as determined by TLC. The reaction was quenched by adding 10% sodium carbonate solution (200 ml) and extracted with dichloromethane (3×200 ml). The combined extracts were dried over sodium sulfate and evaporated under reduced pressure. The residue was separated by flash chromatography on silica gel using dichloromethane-methanol (100:2) as an eluent to give the titled compound, 3-(4-(4-(tosylamino)butyl)piperazin-1-yl)benzenamine, (670 mg, 90% yield). The reduction was also done by hydrogenation with Pd/C as catalyst. It gave the desired product.

$^1$H NMR (400 MHz, $CDCl_3$): δ (ppm), 7.75 (d, 2H), 7.29 (d, 2H), 7.09 (t, 1H), 6.41 (d, 1H), 6.30 (s, 1H), 6.28 (d, 1H), 3.65 (sb, 2H), 3.25-3.22 (m, 4H), 3.00 (t, 2H), 2.63-2.61 (m, 4H), 2.45 (s, 3H), 2.41 (t, 2H), 1.64-1.60 (m, 4H); MS (APCI): m/z 403 (MH$^+$; 100%).

EXAMPLE 3

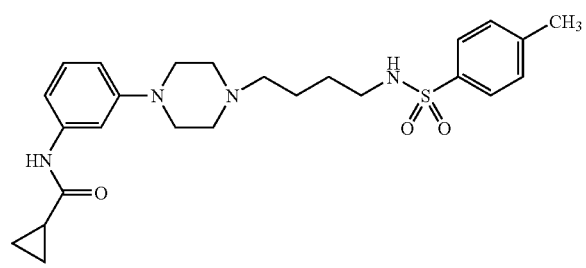

To a solution of the product of Preparation 2 (31 mg, 0.077 mmol) in dichloromethane (3 ml) and pyridine (2 ml) was added cyclopropanecarbonyl chloride (8.1 mg, 0.077 mmol) at 0° C. The mixture was stirred at ambient temperature overnight and the volatiles were removed under reduced pressure. The residue was diluted with dichloromethane, washed with 10% aqueous sodium carbonate solution (2×100 ml) and water (2×100 ml), dried over sodium sulfate, purified with flash chromatography on silica gel (elunt: MeOH/CH$_2$Cl$_2$=1:100) to give the titled compound, Cyclopropanecarboxylic acid (3-{4-[4-(toluene-4-sulfonylamino)-butyl]-piperazin-1-yl}-phenyl)-amide, (27 mg, 75% yield). The acylation was also done by using anhydride to give the desired product.

$^1$H NMR (400 MHz, CDCl$_3$): δ (ppm), 7.70 (d, 2H), 7.42-7.40 (m, 2H), 7.26-7.16 (m, 2H), 6.83 (d, 1H), 6.65 (d, 1H), 3.24-3.22 (m, 4H), 2.96 (t, 2H), 2.59-2.567 (m, 4H), 2.40 (s, 3H), 2.37 (t, 2H), 1.60-1.48 (m, 5H), 1.09-1.07 (m, 2H), 0.86-0.83 (m, 2H). MS (APCI): m/z 471 (MH$^+$; 100%).

EXAMPLE 4

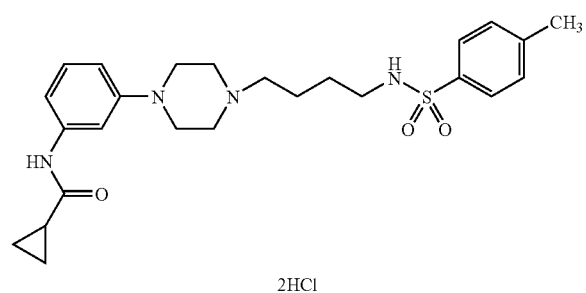

2HCl

Reaction of the product of Example 3 and hydrogen chloride in ether as described in Example 2 gave the desired white solid product, a salt of the compound of Example 3.

$^1$H NMR (400 MHz, CD$_3$OD): δ (ppm), 7.73(d, 2H), 7.48 (s, 1H), 7.38(d, 2H), 7.23(t, 1H), 7.00(d, 1H), 6.79(d, 1H), 3.83(d, 2H), 3.65(d, 2H), 3.28-3.10(m, 6H), 2.90(t, 2H), 2.43 (s, 3H), 1.90-1.82(m, 2H), 1.78-1.74(m, 1H), 1.61-1.56(m, 2H), 0.95-0.92(m, 2H), 0.87-0.84(m, 2H); MS (APCI): m/z 471 (MH$^+$; 100%).

EXAMPLE 5

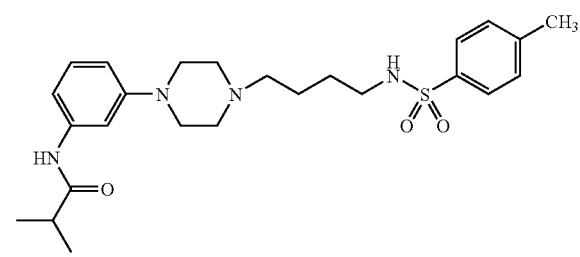

Reaction of the product of Preparation 2 with isobutyryl chloride in dichloromethane as described in Example 3 gave the desired product, N-(3-{4-[4-(Toluene-4-sulfonylamino)-butyl]-piperazin-1-yl}-phenyl)-isobutyramide, as a white solid.

$^1$H NMR (400 MHz, CDCl$_3$): δ (ppm), 7.71 (d, 2H, J=8.4 Hz), 7.44 (m, 1H), 7.25-7.12 (m, 3H), 6.84-6.82 (m, 1H), 6.68-6.65 (m, 1H), 3.27-3.26 (m, 4H), 2.98-2.95 (m, 1H), 2.61-2.58 (m, 4H), 2.553-2.49 (m, 1H), 2.41 (s, 3H), 2.40-2.38 (m, 2H), 1.60-1.58 (m, 4H), 1.27 (s, 3H), 1.26 (s, 3H). MS (APCI): m/z 473 (MH$^+$; 100%).

EXAMPLE 6

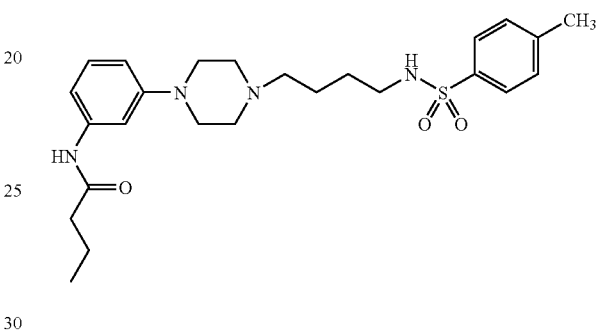

Reaction of the product of Preparation 2 with butyryl chloride in dichloromethane as described in Example 3 gave the desired product, N-(3-{4-[4-(Toluene-4-sulfonylamino)-butyl]-piperazin-1-yl}-phenyl)-butyramide, as a white solid.

$^1$H NMR (400 MHz, CDCl$_3$): δ (ppm), 7.70 (d, 2H), 7.36 (s, 1H), 7.27-7.16 (m, 4H), 6.87 (d, 1H), 6.66 (d, 1H), 3.24-3.22 (m, 4H), 2.97-2.95 (m, 1H), 2.58-2.56 (m, 4H), 2.40 (s, 3H), 2.37-2.32 (m, 4H), 1.79-1.73 (m, 2H), 1.58-1.57 (m, 4H), 1.01 (t, 3H). MS (APCI): m/z 473 (MH$^+$; 100%)

EXAMPLE 7

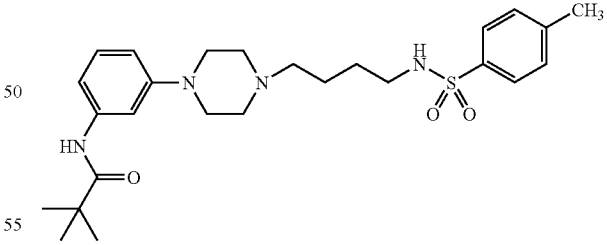

Reaction of the product of Preparation 2 with 2,2-dimethyl-propionyl chloride in dichloromethane as described in Example 3 gave the desired product, 2,2-Dimethyl-N-(3-{4-[4-(toluene-4-sulfonylamino)-butyl]-piperazin-1-yl}-phenyl)-propionamide, as a white solid.

$^1$H NMR (400 MHz, CDCl$_3$): δ (ppm), 7.71 (d, 2H), 7.44-7.35 (m, 1H), 7.29-7.26 (m, 3H), 7.19 (t, 1H), 6.82 (d, 1H), 6.67 (d, 1H), 3.25 (t, 4H), 2.96 (t, 2H), 2.58 (t, 4H), 2.40 (s,

EXAMPLE 8

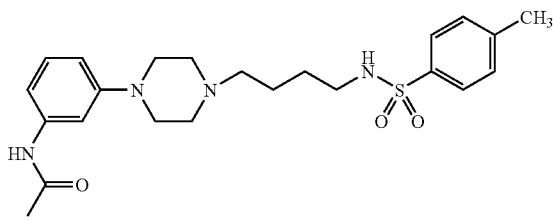

Reaction of the product of Preparation 2 with acetyl chloride in dichloromethane as described in Example 3 gave the desired product, N-(3-{4-[4-(Toluene-4-sulfonylamino)-butyl]-piperazin-1-yl}-phenyl)-acetamide, as a white solid.

$^1$H NMR (400 MHz, CDCl$_3$): δ (ppm), 7.96 (d, 2H), 7.60 (d, 1H), 7.44 (m, 3H), 7.04 (d, 1H), 6.88 (t, 1H), 3.32 (t, 4H), 3.04 (t, 2H), 2.68 (t, 4H), 2.46 (s, 3H), 2.42 (t, 2H), 2.28 (s, 3H), 1.64 (m, 4H); MS (APCI): m/z 445.8 (MH$^+$; 100%).

EXAMPLE 9

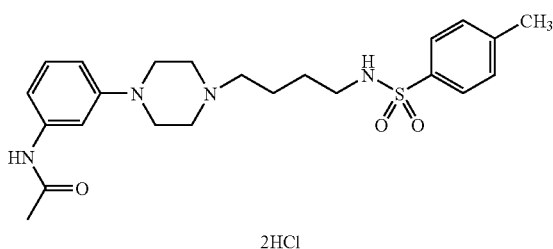

2HCl

Reaction of the product of Example 8 and hydrogen chloride in ether as described in Example 2 gave the desired white solid product, a salt of the compound of Example 8.

$^1$H NMR (400 MHz, CD$_3$OD): δ (ppm), 7.74 (d, 2H), 7.46 (d, 1H), 7.40 (d, 2H), 7.24 (t, 1H), 6.98 (d, 1H), 6.80 (t, 1H), 3.82 (t, 2H), 3.66 (t, 2H), 3.22 (m, 6H), 2.90 (t, 2H), 2.42 (s, 3H), 2.12 (s, 3H), 1.86 (t, 2H), 1.58 (t, 2H); MS (APCI): m/z 445.8 (MH$^+$; 100%).

EXAMPLE 10

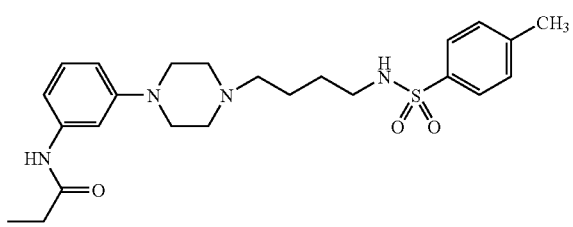

Reaction of the product of Preparation 2 with propionyl chloride in dichloromethane as described in Example 3 gave the desired product, N-(3-{4-[4-(Toluene-4-sulfonylamino)-butyl]-piperazin-1-yl}-phenyl)-propionamide, as a white solid.

$^1$H NMR (400 MHz, CDCl$_3$): δ (ppm), 8.30 (s, 1H), 7.72 (d, 2H), 7.40 (s, 1H), 7.32 (m, 3H), 1s 6.84 (d, 1H), 6.62 (d, 1H), 3.26 (t, 4H), 2.94 (t, 2H), 2.62 (t, 4H), 2.40 (s, 3H), 2.38 (m, 4H), 1.59(m, 4H), 1.24 (t, 3H); MS (APCI): m/z 459.4 (MH$^+$; 100%).

EXAMPLE 11

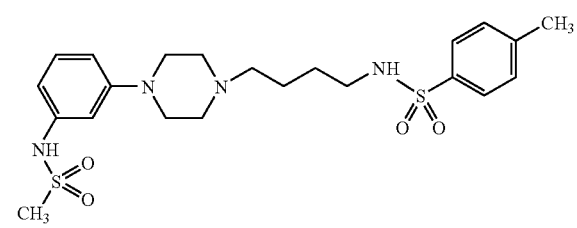

To a mixture of the product of Preparation 2 (31 mg, 0.077 mmol) and pyridine (2 ml) in dichloromethane (5 ml) was added methanesulfonyl chloride (0.008 ml, 0.10 mmol) at 0° C. The mixture was stirred at ambient temperature overnight and concentrated on vacuum to dryness. The resulting residue was diluted with dichloromethane and washed with aqueous sodium carbonate solution, water, dried over sodium sulfate, filtered, and concentrated. Purification by silica gel chromatography (methanol/dichloromethane) gave 36 mg (97%) of the desired product, N-{4-[4-(3-Methanesulfonylamino-phenyl)-piperazin-1-yl]-butyl}-4-methyl-benzenesulfonamide, as a white solid.

$^1$H NMR (400 MHz, CDCl$_3$): 7.71 (d, 2H), 7.27 (d, 2H), 7.22 (t, 1H), 6.81 (s, 1H), 6.74 (d, 1H), 6.67 (d, 1H), 3.25 (t, 4H), 3.01 (s, 3H), 2.96 (t, 2H), 2.59 (t, 4H), 2.41 (s, 3H), 2.37 (t, 2H), 1.61-1.57 (m, 4H); MS (APCI): m/z 481 (MH$^+$; 100%).

EXAMPLE 12

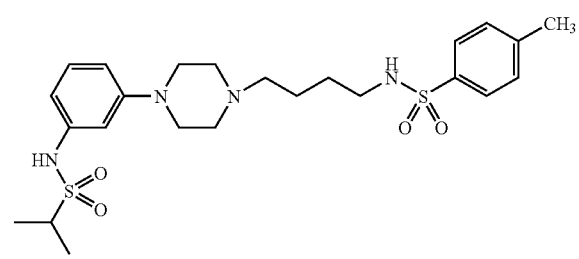

Reaction of the product of Preparation 2 with propane-2-sulfonyl chloride in dichloromethane as described in Example 11 gave the desired product, 4-Methyl-N-(4-{4-[3-(propane-2-sulfonylamino)-phenyl]-piperazin-1-yl}-butyl)-benzenesulfonamide, as a white solid.

$^1$H NMR (400 MHz, CDCl$_3$): δ (ppm), 7.72(d, 2H), 7.26 (d, 2H), 7.18 (t, 1H), 6.85-6.84 (m, 1H), 6.71-6.67 (m, 2H), 3.36-3.30 (m, 1H), 3.24-3.22 (m, 4H), 2.96 (t, 2H), 2.59-2.56

(m, 4H), 2.41 (s, 3H), 2.36 (t, 2H), 1.58-1.56 (m, 4H), 1.38 (d, 6H); MS (APCI): m/z 509 (MH+; 100%).

EXAMPLE 13

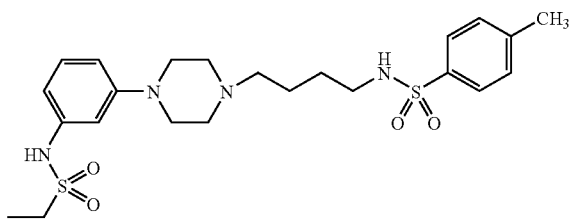

Reaction of the product of Preparation 2 with ethanesulfonyl chloride in dichloromethane as described in Example 11 gave the desired product, N-{4-[4-(3-Ethanesulfonylaminophenyl)-piperazin-1-yl]-butyl}-4-methyl-benzenesulfonamide, as a white solid.

¹H NMR (400 MHz, CDCl₃): 7.72 (d, 2H), 7.29 (d, 2H), 7.22 (t, 1H), 6.83 (t, 1H), 6.74 (d, 1H), 6.64 (d, 1H), 3.30 (t, 4H), 3.14 (q, 2H), 2.98 (t, 2H), 2.67 (t, 4H), 2.46 (t, 2H), 2.42 (s, 3H), 1.62(t, 4H), 1.37 (t, 3H); MS (APCI): m/z 495.5 (MH+; 100%).

EXAMPLE 14

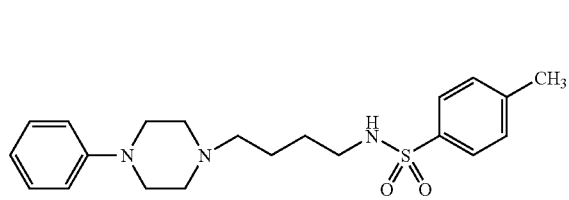

Reaction of 1-phenyl-piperazine and the product of Preparation 1 as described in Example 1 gave the desired product, 4-Methyl-N-[4-(4-phenyl-piperazin-1-yl)-butyl]-benzenesulfonainide.

¹H NMR (400 MHz, CDCl₃): δ (ppm), 7.72 (d, 2H), 7.29-7.24 (m, 4H), 6.93 (d, 2H), 6.87 (t, 1H), 3.21 (t, 4H), 2.96 (t, 2H), 2.58 (t, 4H), 2.39 (s, 3H), 2.53 (t, 2H), 1.62-1.54 (m, 4H); MS (APCI): m/z 388 (MH+; 100%).

EXAMPLE 15

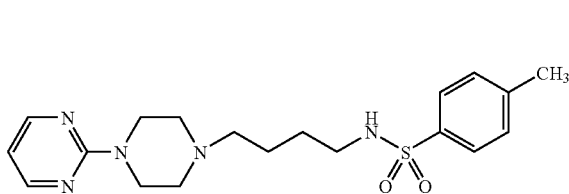

Reaction of 2-piperazin-1-yl-pyrimidine and the product of Preparation 1 as described in Example 1 gave the desired product, 4-Methyl-N-[4-(4-pyrimidin-2-yl-piperazin-1-yl)-butyl]-benzenesulfonamide.

¹H NMR (400 MHz, CDCl₃): δ (ppm), 8.36 (d, 2H), 7.78 (d, 2H), 7.34 (d, 2H), 6.52 (t, 1H), 3.90 (t, 4H), 3.00 (t, 2H), 2.54 (t, 4H), 2.42 (s, 3H), 2.36 (t, 2H), 1.60 (m, 4H); MS (APCI): m/z 390.2 (MH+; 100%).

EXAMPLE 16

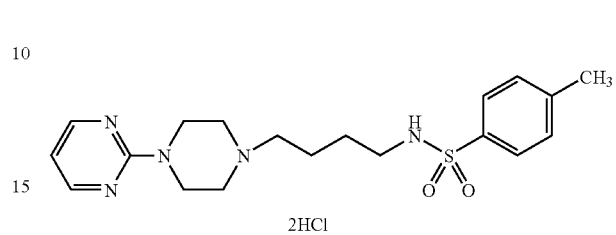

Reaction of the product of Example 15 and hydrogen chloride in ether as described in Example 2 gave the desired white solid product, a salt of the compound of Example 15.

¹H NMR (400 MHz, CD₃OD): δ (ppm), 9.28 (d, 2H), 8.22 (br s, 1H), 7.92 (d, 2H), 7.74 (t, 1H), 7.10 (br s, 1H), 4.26 (t, 4H), 3.96 (t, 4H), 3.34 (m, 4H), 2.38 (s, 3H), 1.96 (m, 4H); MS (APCI): m/z 390.2 (MH+; 100%).

EXAMPLE 17

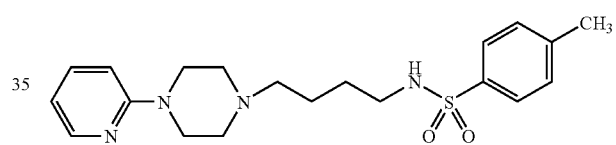

Reaction of 1-pyridin-2-yl-piperazine and the product of Preparation 1 as described in Example 1 gave the desired product, 4-Methyl-N-[4-(4-pyridin-2-yl-piperazin-1-yl)-butyl]-benzenesulfonamide.

¹H NMR (400 MHz, CDCl₃): δ (ppm), 8.20 (d, 1H), 7.72 (d, 2H), 7.51-7.47 (m, 1H), 7.26 (d, 2H), 6.66-6.23 (m, 2H), 3.59 (t, 4H), 2.97 (t, 2H), 2.56 (t, 4H), 2.41 (s, 3H), 2.37 (t, 2H), 1.60-1.58 (m, 4H); MS (APCI): m/z 389 (MH+; 100%).

EXAMPLE 18

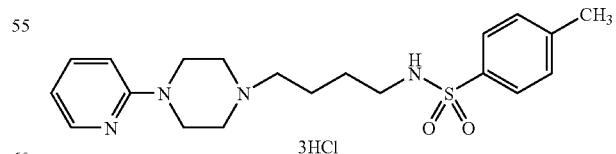

Reaction of the product of Example 17 and hydrogen chloride in ether as described in Example 2 gave the desired white solid product, a salt of the compound of Example 17.

¹H NMR (400 MHz, CD₃OD): δ (ppm), 8.17-8.08(m, 2H), 7.76(d, 2H), 7.48(d, 1H), 7.39(d, 2H), 7.15(t, 1H), 4.41(m, 2H), 3.76(m, 4H), 3.33-3.23(m, 4H), 2.89(t, 2H), 2.43(s, 3H), 1.94-1.86(m, 2H), 1.63-1.56(m, 2H); MS (APCI): m/z 389 (MH+; 100%).

Preparation 3

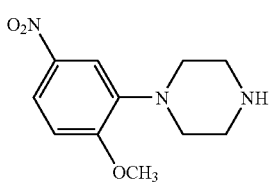

A mixture of 2-methoxy-5-nitro-phenylamine (16.8 g, 0.1 mol), bis-(2-chloro-ethyl)-amine hydrochloride (17.8 g, 0.1 mol) and potassium carbonate (69 g, 0.5 mol) in chlorobenzene (300 ml) was refluxed for 48 h, washed by water. The water phase was extracted with dichloromethane. The organic layers were combined, dried over sodium sulfate, purified with flash chromatography on silica gel (CH$_2$Cl$_2$/MeOH) to give the desired product, 1-(2-methoxy-5-nitrophenyl)piperazine (10.7 g, 45%).

$^1$H NMR (400 MHz, CDCl$_3$): δ (ppm), 7.95 (dd, 1H), 7.79 (d, 1H), 6.90 (d, 1H), 3.98 (s, 3H), 3.09 (s, 8H), 1.96 (s, 1H). MS (APCI): m/z 238 (MH+; 100%).

EXAMPLE 19

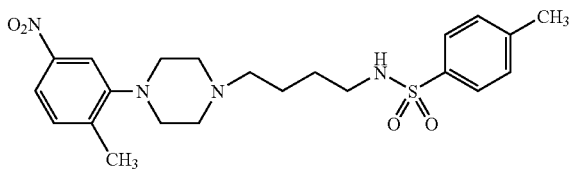

Reaction of the product of Preparation 3 and the product of Preparation 1 as described in Example 1 gave the desired product, N-{4-[4-(2-Methoxy-5-nitro-phenyl)-piperazin-1-yl]-butyl}-4-methyl-benzenesulfonamide.

$^1$H NMR (400 MHz, CDCl$_3$): δ (ppm), 7.97 (dd, 1H), 7.8 (d, 1H), 7.74 (d, 2H), 7.32 (d, 2H), 6.91 (d, 1H), 3.98 (s, 3H), 3.22-3.16 (m, 4H), 2.99 (t, 2H), 2.68-2.62 (m, 4H), 2.44 (s, 3H), 2.41 (t, 2H), 1.63-1.58 (m, 4H); MS (APCI): m/z 447 (MH+; 100%).

Preparation 4

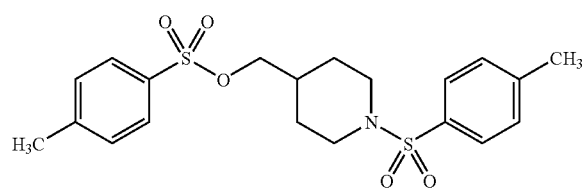

Reaction of tosyl chloride and piperidin-4-yl-methanol as described in Preparation 1 gave the desired compound, (1-tosylpiperidin-4-yl)methyl 4-methylbenzenesulfonate, which was used without further purification.

EXAMPLE 20

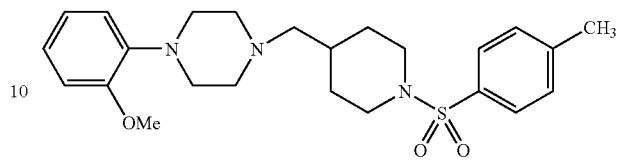

Reaction of 1-(2-methoxy-phenyl)-piperazine and the product of Preparation 4 as described in Example 1 gave the desired product, 1-(2-Methoxy-phenyl)4-[1-(toluene-4-sulfonyl)-piperidin-3-ylmethyl]-piperazine.

$^1$H NMR (400 MHz, CDCl$_3$): δ (ppm), 7.64 (d, 2H), 7.31 (d, 2H), 6.90 (m, 2H), 6.85 (d, 2H), 3.84 (s, 3H), 3.80 (t, 4H), 3.47 (d, 2H), 3.03 (t, 2H), 2.54 (t, 2H), 2.43 (s, 3H), 2.24 (m, 2H), 1.80 (t, 2H), 1.60 (m, 1H), 1.34 (m, 4H); MS (APCI): m/z 444.2 (MH+; 100%).

EXAMPLE 21

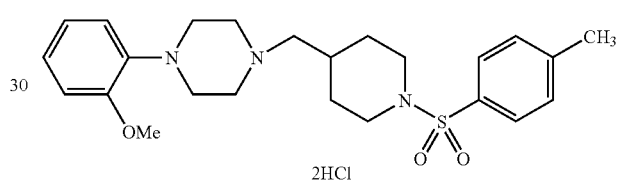

Reaction of the product of Example 20 and hydrogen chloride in ether as described in Example 2 gave the desired white solid product, a salt of the compound of Example 20.

$^1$H NMR (400 MHz, CD$_3$OD): δ (ppm), 7.82 (d, 2H), 7.44 (m, 1H), 7.38 (d, 2H), 7.16 (m, 3H), 4.01 (t, 4H), 3.80 (s, 3H), 3.78 (t, 2H), 3.49 (d, 2H), 3.03 (t, 2H), 2.41 (s, 3H), 2.19 (m, 2H), 1.96 (t, 2H), 1.63 (m, 1H), 1.30 (m, 4H); MS (APCI): m/z 444.2 (MH+; 100%).

Preparation 5

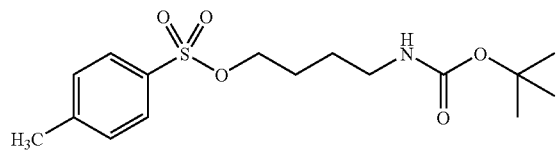

Reaction of (4-hydroxy-butyl)-carbamic acid tert-butyl ester and tosyl chloride as described in 1 gave the desired compound which was used without further purification.

Preparation 6

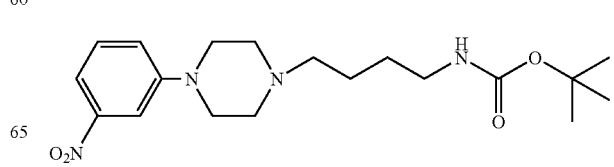

Reaction of 1-(3-nitro-phenyl)-piperazine and the product of Preparation 5 as described in Example 1 gave the desired compound, tert-butyl 4-(4-(3-nitrophenyl)piperazin-1-yl)butylcarbamate.

$^1$H NMR (400 MHz, CDCl$_3$): δ (ppm), 7.78 (s, 1H), 7.67 (d, 1H), 7.41 (t, 1H), 7.21 (d, 1H), 5.21 (bs, 1H), 3.39-3.21 (m, 4H), 2.68 (m, 4H), 2.23 (m, 2H), 2.17 (m, 2H), 1.78-1.42 (m, 4H), 1.44 (s, 9H); MS (APCI): m/z 379 MH$^+$; 100%).

Preparation 7

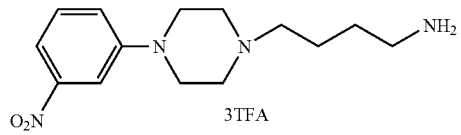

To a solution of the product of Preparation 6 (14.0 g, 0.037 mol) in dichloromethane (100 mL) at 0 C, trifluoroacetic acid (10 mL, 0.13 mol) was added. The resultant solution was stirred for additional 2 hours. Solvent was evaporated under reduced pressure. Residue was washed with diethyl ether (100 mL). Precipitate was dried to obtain product, 4-(4-(3-nitrophenyl)piperazin-1-yl)butan-1-amine (16.85 g) in 90% yield.

$^1$H NMR (400 MHz, CD$_3$OD): δ (ppm), 10.05 (bs, 1H), 7.79-7.42 (m, 4H), 4.07-3.48 (m, 4H), 3.25 (bs, 3H), 2.83 (m, 4H), 2.17 (m, 2H), 1.99-1.42 (m, 6H); MS (APCI): m/z 279 MH$^+$; 100%). The reaction was also done by using hydrogen chloride in dioxane to give the desired product.

Preparation 8

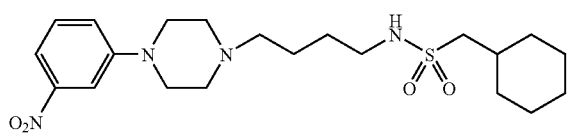

To a solution of the product of Preparation 7 (0.5 mmol) in dichloromethane (25 ml) and triethylamine (0.75 mmol) was added cyclohexyl-methanesulfonyl chloride (0.5 mmol) at 0° C. The mixture was allowed to stir at 0° C. for 2-3 h and the volatiles were removed under reduced pressure. The residue was diluted with dichloromethane, washed with 10% aqueous sodium carbonate solution (2×15 ml) and water (2×15 ml) and dried over sodium sulfate. After removal of solvent, the residue was purified with flash chromatography on silica gel (2% MeOH/CH$_2$Cl$_2$) to give the titled compound (75-88% yield).

$^1$H NMR (400 MHz, CDCl$_3$): δ (ppm), 7.45 (s, 1H), 7.21 (t, 1H), 6.97 (d, 1H), 6.75 (d, 1H), 3.85 (m, 2H), 3.63 (m 2H), 3.28-3.05 (m, 14H), 1.99-1.39 (m, 12H); MS (APCI): m/z 439 MH$^+$; 100%).

Preparation 9

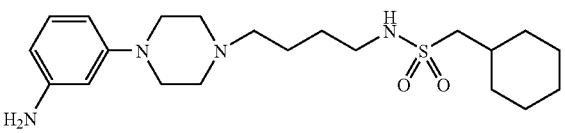

Reaction of the product of Preparation 9 and tin chloride or hydrogenation with Pd/C as catalyst as described in Preparation 2 gave the desired product.

$^1$H NMR (400 MHz, CDCl$_3$): δ (ppm), 7.50 (s, 1H), 7.11 (t, 1H), 6.89 (d, 1H), 6.69 (d, 1H), 3.85 (bs, 2H), 3.63 (m 2H), 3.35-3.02 (m, 16H), 2.01-1.44 (m, 12H); MS (APCI): m/z 409 MH$^+$; 100%).

Preparation 10

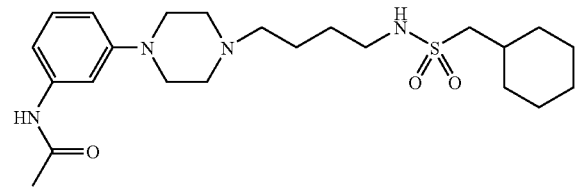

Reaction of the product of Preparation 9 with acetyl chloride in dichloromethane as described in Example 3 gave the desired product, N-{3-[4-(4-Cyclohexylmethanesulfonylamino-butyl)-piperazin-1-yl]-phenyl}-acetamide, as a white solid.

$^1$H NMR (400 MHz, CDCl$_3$): δ (ppm), 7.44 (s, 1H), 7.30 (s, 1H), 7.20 (t, 1H), 6.93 (d, 1H), 6.70 (brs, 1H), 6.68 (d, 1H), 3.27 (t, 4H), 3.15 (t, 2H), 2.89 (d, 2H), 2.46 (t, 4H), 2.45 (t, 2H), 2.19 (s, 3H), 1.99 (t, 2H), 1.68 (m, 7H), 1.33-1.02 (m, 6H); MS (APCI): m/z 451.3 (MH$^+$; 100%).

EXAMPLE 22

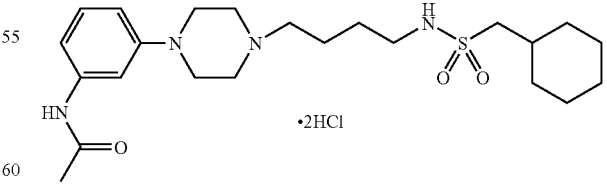

Reaction of the product of Preparation 10 and hydrogen chloride in ether as described in Example 2 gave the desired white solid product, a salt of the compound of Preparation 10.

$^1$H NMR (400 MHz, CD$_3$OD): δ (ppm), 7.50 (t, 1H), 7.27 (t, 1H), 7.02 (d, 1H), 6.85 (d, 1H), 3.88 (t, 2H), 3.74 (t, 2H), 2.46 (t, 2H), 2.45 (t, 2H), 2.98 (d, 2H), 2.15 (s, 3H), 1.99 (m, 6H), 1.68 (m, 6H), 1.33-1.02 (m, 7H); MS (APCI): n/z 451.3 (MH+; 100%).

Preparation 11

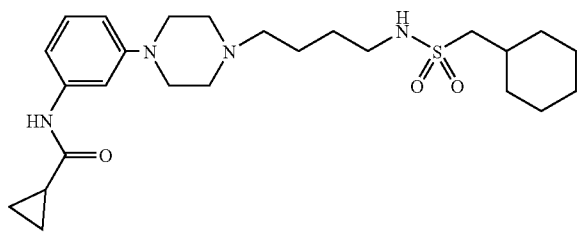

Reaction of the product of Preparation 9 with cyclopropanecarbonyl chloride in dichloromethane as described in Example 3 gave the desired product, Cyclopropanecarboxylic acid {3-[4-(4-cyclohexylmethanesulfonylamino-butyl)-piperazin-1-yl]-phenyl}-amide, as a white solid.

$^1$H NMR (400 MHz, CDCl$_3$): δ (ppm), 7.41-7.17 (m, 2H), 6.82 (d, 1H), 6.65 (d, 1H), 3.24(m, 4H), 3.05 (m, 4H), 2.87 (m, 4H), 2.62 (m, 4H), 2.41 (m, 2H), 1.95-1.49 (m, 13H), 1.38-0.91 (m, 5H); MS (APCI): m/z 477 (MH+; 100%).

EXAMPLE 23

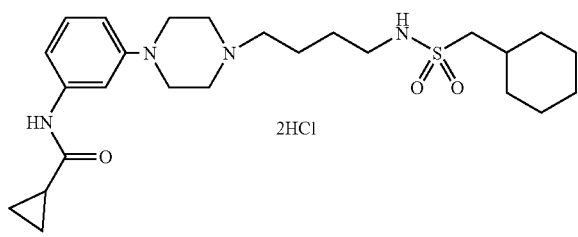

Reaction of the product of Preparation 11 and hydrogen chloride in ether as described in Example 2 gave the desired white solid product, a salt of the product of Preparation 11.

$^1$H NMR (400 MHz, CD$_3$OD): δ (ppm), 7.48 (s, 1H), 7.27 (t, 1H), 6.92 (d, 1H), 6.71 (d, 1H), 4.84 (bs, 4H), 3.90 (m, 2H), 3.68 (m 2H), 3.34-3.02 (m, 15H), 1.95-1.49 (m, 10H), 1.38-0.91 (m, 5H); MS (APCI): m/z 477 (MH+; 100%).

Preparation 12

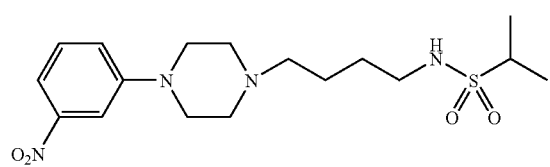

Reaction of propane-2-sulfonyl chloride and the product of Preparation 7 as described in Preparation 8 gave the desired product.

$^1$H NMR (400 MHz, CD$_3$OD): δ (ppm), 7.81-7.69(m, 2H), 7.44-7.22(m, 2H), 6.60(sb, 1H), 3.44-3.33(m, 4H), 3.24-3.13 (m, 3H), 2.75-2.64(m, 4H), 2.58-2.50(m, 2H), 1.77-1.70(m, 4H), 1.40(d, 6H); MS (APCI): n/z 385 (MH+; 100%).

Preparation 13

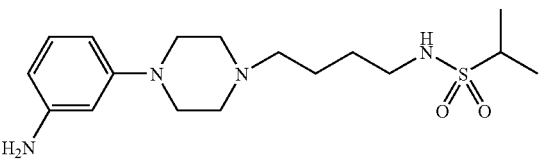

Reaction of the product of Preparation 9 and tin chloride as described in Preparation 2 gave the desired product.

$^1$H NMR (400 MHz, CD$_3$OD): δ (ppm), 7.04(t, 1H), 6.36 (d, 1H), 6.26-6.21(m, 2H), 3.60(sb, 2H), 3.22-3.01(m, 7H), 2.63-2.61(m, 4H), 2.44(t, 2H), 1.70-1.64(m, 4H), 1.34(d, 6H); MS (APCI): m/z 355 (MH+; 100%).

Preparation 14

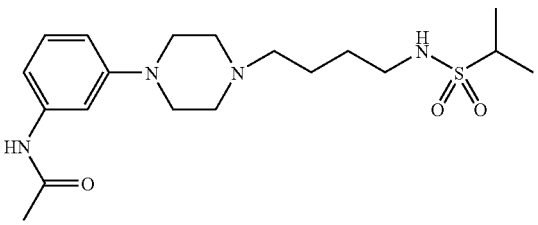

Reaction of the product of Preparation 13 with acetyl chloride in dichloromethane as described in Example 3 gave the desired product, N-(3-{4-[4-(Propane-2-sulfonylamino)-butyl]-piperazin-1-yl}-phenyl)-acetamide, as a white solid.

$^1$H NMR (400 MHz, CDCl$_3$): δ (ppm), 7.32-7.21(m, 2H), 6.92(d, 1H), 6.71(d, 2H), 3.29-3.11(m, 7H), 2.67-2.66(m, 4H), 2.50-2.48(m, 2H), 2.22(s, 3H), 1.77-1.66(m, 4H), 1.39 (d, 6H); MS (APCI): m/z 397 (MH+; 100%).

EXAMPLE 24

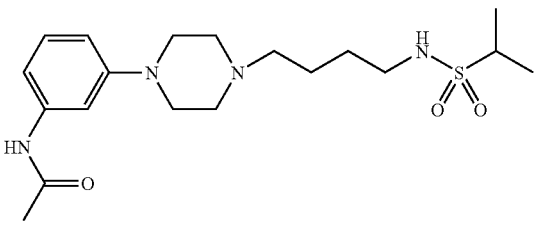

2HCl

Reaction of the product of Preparation 14 and hydrogen chloride in ether as described in Example 2 gave the desired white solid product, a salt of the product of Preparation 14.

$^1$H NMR (400 MHz, CD$_3$OD): δ (ppm), 7.50(s, 1H), 7.27 (m, 1H), 7.02(d, 1H), 6.84(d, 1H), 3.90-3.72(m, 4H), 3.41-3.31(m, 9H), 2.17(t, 3H), 1.97-1.91(m, 2H), 1.72-1.65(m, 2H), 1.38(d, 6H), MS (APCI): m/z 397 (MH$^+$; 100%).

Preparation 15

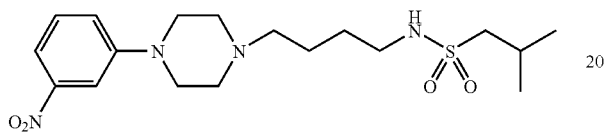

Reaction of 2-methyl-propane-1-sulfonyl chloride and the product of Preparation 7 as described in Preparation 8 gave the desired product. The crude mixture was used for reduction without further purification.

MS (APCI): m/z 399 (MH$^+$; 100%).

Preparation 16

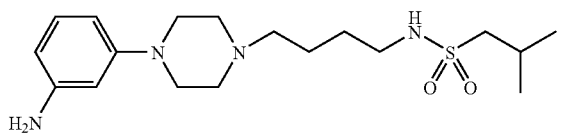

Reaction of the product of Preparation 15 and tin chloride or hydrogenation or the product of Preparation 15 by using Pd/C as catalyst as described in Preparation 2 gave the desired product.

$^1$H NMR (400 MHz, CDCl$_3$): δ (ppm), 7.03(t, 1H), 6.37-6.34(m, 1H), 6.25-6.20(m, 2H), 3.21-3.18(m, 4H), 3.08(t, 2H), 2.85(d, 2H), 2.61-2.85(m, 4H), 2.42(t, 2H), 2.27-2.16 (m, 1H), 1.68-1.61(m, 4H), 1.08(d, 6H); MS (APCI): m/z 369 (MH$^+$; 100%).

Preparation 17

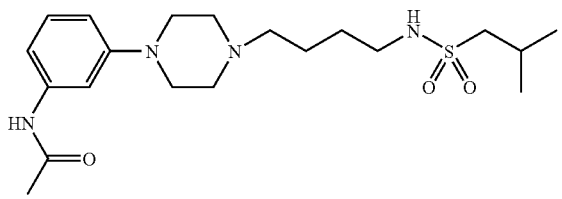

Reaction of the product of Preparation 16 and acetyl chloride in dichloromethane as described in Example 3 gave the desired product, N-(3-{4-[4-(2-Methyl-propane-1-sulfonylamino)-butyl]-piperazin-1-yl}-phenyl)-acetamide, as a white solid.

$^1$H NMR (400 MHz, CDCl$_3$): δ (ppm), 7.02(t, 1H), 6.36(d, 1H), 6.24(t, 1H), 6.21(d, 1H), 3.21-3.18(m, 4H), 3.08(t, 2H), 2.85(d, 2H), 2.61-2.59(m, 4H), 2.42(t, 2H), 2.27-2.20(m, 1H), 1.68-1.61(m, 4H), 1.08(d, 6H); MS (APCI): m/z 411 (MH$^+$; 100%).

EXAMPLE 25

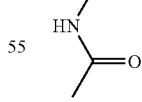

2HCl

Reaction of the product of Preparation 17 and hydrogen chloride in ether as described in Example 2 gave the desired white solid product, a salt of the product of Preparation 17.

$^1$H NMR (400 MHz, CD$_3$OD): δ (ppm), 7.5(s, 1H), 7.22(t, 1H), 6.95(d, 1H), 6.78(d, 1H), 3.83(d, 2H), 3.67(d, 2H), 3.28-3.22(m, 4H), 3.14-3.05(m, 4H), 2.95(d, 2H), 2.23-2.15(m, 1H), 2.12(s, 3H), 1.94-1.86(m, 2H), 1.67-1.61(m, 2H), 1.10 (d, 6H); MS (APCI): m/z 411 (MH$^+$; 100%).

Preparation 18

Reaction of cyclohexanesulfonic acid {4-[4-(3-aminophenyl)-piperazin-1-yl]-butyl}-amide and acetyl chloride in dichloromethane as described in Example 3 gave the desired product, N-{3-[4-(4-Cyclohexanesulfonylamino-butyl)-piperazin-1-yl]-phenyl}-acetamide, as a white solid.

$^1$H NMR (400 MHz, CDCl$_3$): δ (ppm), 7.36 (t, 1H), 7.28 (t, 1H), 6.91 (d, 1H), 6.73 (d, 1H), 3.28 (t, 4H), 3.16 (t, 2H), 2.86

(m, 1H), 2.66 (t, 4H), 2.49 (t, 2H), 2.21 (s, 3H), 1.99-1.12 (m, 14H); MS (APCI): m/z 437.3 (MH+; 100%).

EXAMPLE 26

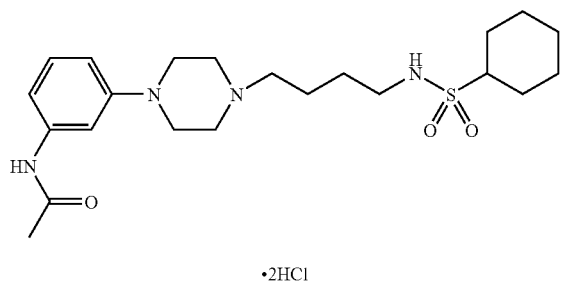

•2HCl

Reaction of the product of Preparation 18 and hydrogen chloride in ether as described in Example 2 gave the desired white solid product, a salt of the product of Preparation 18.

$^1$H NMR (400 MHz, CD$_3$OD): δ (ppm), 7.69 (t, 1H), 7.42 (t, 1H), 7.22 (d, 1H), 7.13 (d, 1H), 3.78 (t, 2H), 3.62 (t, 2H), 3.46 (t, 2H), 3.01 (m, 1H), 2.98 (t, 4H), 2.49 (t, 2H), 2.19 (s, 3H), 2.14 (t, 2H), 1.99-1.12 (m, 14H); MS (APCI): m/z 437.3 (MH+; 100%).

Preparation 19

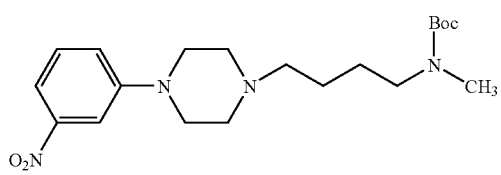

Reaction of 1-(3-nitro-phenyl)-piperazine and toluene-4-sulfonic acid 4-(tert-butoxycarbonyl-methyl-amino)-butyl ester as described in Example 1 gave the desired compound.

$^1$H NMR (400 MHz, CDCl$_3$): δ (ppm), 7.75 (s, 1H), 7.63 (dd, 1H), 7.34 (t, 1H), 7.19 (dd, 1H), 3.47 (m, 4H), 2.68 (m, 4H), 2.37 (s, 3H), 2.23 (m, 2H), 2.17 (m, 2H), 1.88-1.45 (m, 4H), 1.44 (s, 9H); MS (APCI): m/z 393 MH+; 100%).

Preparation 20

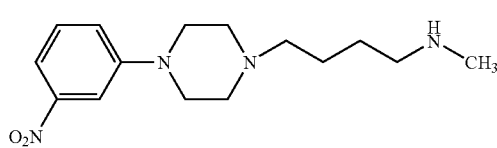

3TFA

Reaction of the product of Preparation 19 and TFA as described in Preparation 7 gave the desired product.

$^1$H NMR (400 MHz, CD$_3$OD): δ (ppm), 7.75 (s, 1H), 7.53 (t, 1H), 7.25 (d, 1H), 7.-09 (d, 1H), 4.56 (bs, 3H), 3.48 (m, 4H), 2.78 (m, 4H), 2.27 (s, 3H), 2.13 (m, 2H), 1.99-1.45 (m, 6H); MS (APCI): m/z 293 MH+; 100%).

Preparation 21

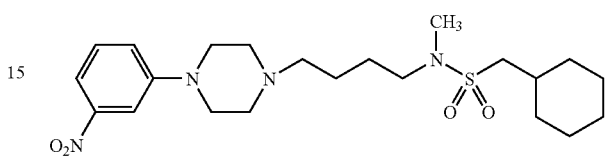

Reaction of cyclohexyl-methanesulfonyl chloride and the product of Preparation 20 as described in Preparation 8 gave the desired product.

$^1$H NMR (400 MHz, CDCl$_3$): δ (ppm), 7.35 (s, 1H), 7.23 (t, 1H), 6.94 (d, 1H), 6.81 (d, 1H), 3.87 (m, 2H), 3.68 (m 2H), 3.25-3.03 (m, 14H), 2.17 (s, 3H), 1.96-1.34 (m, 11H); MS (APCI): m/z 453 MH+; 100%).

Preparation 22

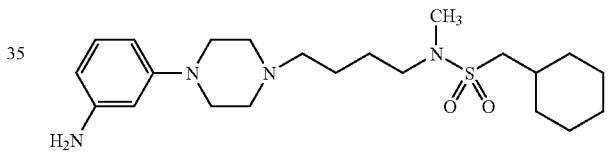

Reaction of the product of Preparation 21 and tin chloride as described in Preparation 2 gave the desired product.

$^1$H NMR (400 MHz, CDCl$_3$): δ (ppm), 7.25 (m, 2H), 6.937 (d, 1H), 6.30 (d, 1H), 3.85 (bs, 2H), 3.63 (m 2H), 3.28-3.05 (m, 16H), 2.17 (s, 3H), 1.99-1.39 (m, 1H); MS (APCI): m/z 423 MH+; 100%).

Preparation 23

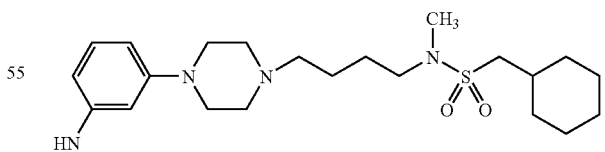

Reaction of the product of Preparation 22 and acetyl chloride in dichloromethane as described in Example 3 gave the desired product, N-(3-{4-[4-(Cyclohexylmethanesulfonyl-methyl-amino)-butyl]-piperazin-1-yl}-phenyl)-acetamide, as a white solid.

¹H NMR (400 MHz, CDCl₃): δ (ppm), 7.37 (s, 1H), 7.15 (t, 1H), 6.98 (d, 1H), 6.71 (d, 1H), 3.43-3.25 (m, 6H), 2.97-1.47 (m 30 H); MS (APCI): m/z 465 (MH⁺; 100%).

EXAMPLE 27

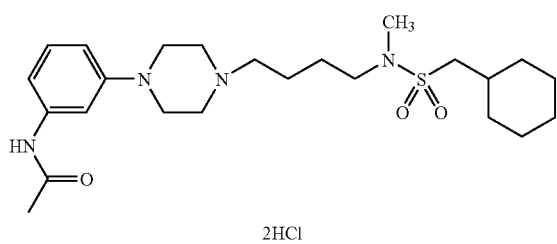

2HCl

Reaction of the product of Preparation 23 and hydrogen chloride in ether as described in Example 2 gave the desired white solid product, a salt of the product of Preparation 23.

¹H NMR (400 MHz, CDCl₃): δ (ppm), 7.42 (s, 1H), 7.21 (t, 1H), 6.97 (d, 1H), 6.75 (d, 1H), 4.84 (bs, 4H), 3.85 (m, 2H), 3.63 (m 2H), 3.28-3.05 (m, 13H), 2.07 (s, 3H), 1.99-1.15 (m, 14H); MS (APCI): m/z 465 (MH⁺; 100%).

Preparation 24

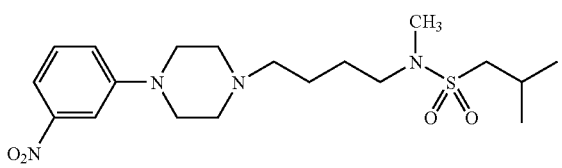

Reaction of 2-methyl-propane-1-sulfonyl chloride and the product of Preparation 20 as described in Preparation 8 gave the desired product.

¹H NMR (400 MHz, CDCl₃): δ (ppm), 7.26 (s, 1H), 7.12 (t, 1H), 6.96 (d, 1H), 6.77 (d, 1H), 3.89 (m, 2H), 3.65 (m 2H), 3.29-3.02 (m, 14H), 2.17 (s, 3H), 1.97-1.34 (m, 7H); MS (APCI): m/z 413 MH⁺; 100%).

Preparation 25

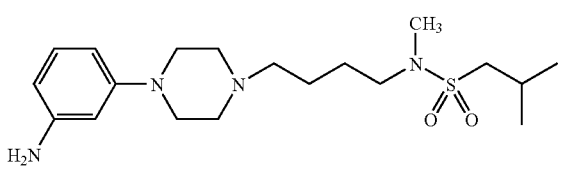

Reaction of the product of Preparation 24 and tin chloride or hydrogenation of the product of Preparation 24 by using Pd/C as catalyst as described in Preparation 2 gave the desired product.

¹H NMR (400 MHz, CDCl₃): δ (ppm), 7.27 (s, 1H), 7.13 (t, 1H), 6.95 (d, 1H), 6.74 (d, 1H), 3.95 (bs, 2H), 3.65 (m 2H), 3.29-3.03 (m, 16H), 2.17 (s, 3H), 1.99-1.39 (m, 5H); MS (APCI): m/z 383 MH⁺; 100%).

Preparation 26

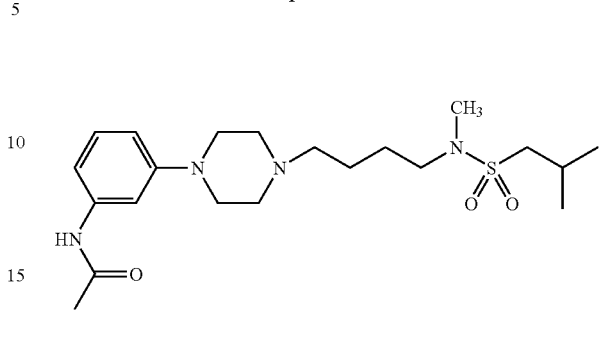

Reaction of the product of Preparation 25 and acetyl chloride in dichloromethane as described in Example 3 gave the desired product, N-(3-{4-[1-(Propane-2-sulfonyl)-piperidin-4-ylmethyl]-piperazin-1-yl}-phenyl)-acetamide, as a white solid.

¹H NMR (400 MHz, CDCl₃): δ (ppm), 7.47 (s, 1H), 7.23 (t, 1H), 6.98 (d, 1H), 6.73 (d, 1H), 3.43-3.25 (m, 6H), 2.97-1.17 (m 26 H); MS (APCI): m/z 425 (MH⁺; 100%).

EXAMPLE 28

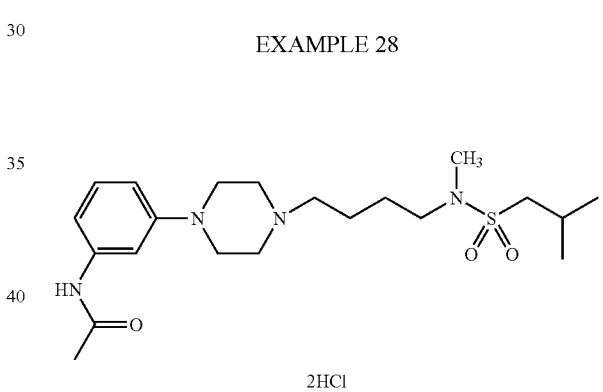

2HCl

Reaction of the product of Preparation 26 and hydrogen chloride in ether as described in Example 2 gave the desired white solid product, a salt of the product of Preparation 26.

¹H NMR (400 MHz, CD₃OD): δ (ppm), 7.45 (s, 1H), 7.26 (t, 1H), 6.97 (d, 1H), 6.85 (d, 1H), 4.87 (bs, 4H), 3.87 (m, 2H), 3.73 (m 2H), 3.38-3.05 (m, 12H), 2.07 (s, 3H), 1.99-1.15 (m, 11H); MS (APCI): m/z 425 (MH⁺; 100%).

Preparation 27

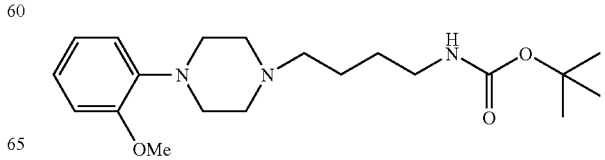

Reaction of 1-(2-methoxy-phenyl)-piperazine and the product of Preparation 5 as described in Example 1 gave the desired compound.

¹H NMR (400 MHz, CDCl₃): δ (ppm), 7.02 (m, 4H), 3.92 (s, 3H), 3.21 (t, 6H), 2.76 (t, 4H), 2.44 (t, 2H), 1.60 (m, 4H), 1.41 (s, 9H); MS (APCI): m/z 364.5 (MH⁺; 100%).

Preparation 28

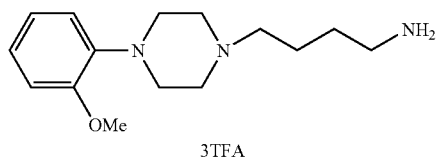

3TFA

Reaction of the product of Preparation 27 and TFA as described in Preparation 7 gave the desired product.

¹H NMR (400 MHz, CD₃OD): δ (ppm), 7.29 (m, 2H), 6.64 (m, 2H), 3.90 (s, 3H), 3.28 (t, 2H), 3.19 (t, 2H), 3.01 (t, 2H), 2.62 (t, 4H), 2.39 (t, 2H), 1.55 (m, 4H); MS (APCI): m/z 264.3 (MH⁺; 100%).

EXAMPLE 29

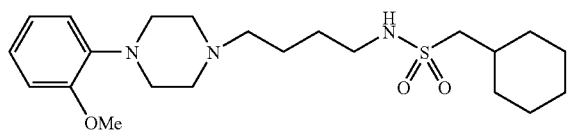

Reaction of cyclohexyl-methanesulfonyl chloride and the product of Preparation 28 as described in Preparation 8 gave the desired product, C-Cyclohexyl-N-{4-[4-(2-methoxy-phenyl)-piperazin-1-yl]-butyl}-methanesulfonamide.

¹H NMR (400 MHz, CDCl₃): δ (ppm), 6.98 (m, 4H), 3.86 (s, 3H), 3.10 (t, 6H), 2.85 (d, 2H), 2.64 (t, 2H), 2.49 (t, 2H), 1.98(m, 3H), 1.67 (m, 8H), 1.26-0.91 (m, 6H); MS (APCI): m/z 424.2 (MH⁺; 100%).

EXAMPLE 30

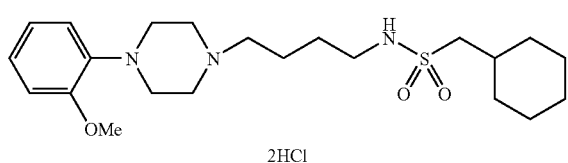

2HCl

Reaction of the product of Example 29 and hydrogen chloride in ether as described in Example 2 gave the desired white solid product, a salt of the product of Example 29.

¹H NMR (400 MHz, CD₃OD): δ (ppm), 7.91 (d, 1H), 7.48 (m, 1H), 7.22 (d, 2H), 3.80 (s, 3H), 3.52 (t, 4H), 3.41 (t, 2H), 2.91 (d, 2H), 2.89 (t, 2H), 2.77 (t, 2H), 2.51 (t, 2H), 1.62 (m, 9H), 1.29-0.86 (m, 6H); MS (APCI): m/z 424.2 (MH⁺; 100%).

Preparation 29

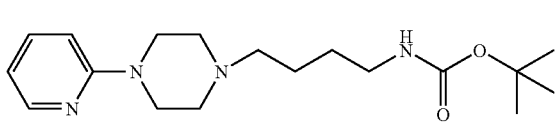

Reaction of {3-[4-(4-amino-butyl)-piperazin-1-yl]-phenyl}-dimethyl-amine and cyclohexyl-methanesulfonyl chloride as described in Preparation 8 gave desired compound, C-Cyclohexyl-N-{4-[4-(3-dimethylamino-phenyl)-piperazin-1-yl]-butyl}-methanesulfonamide.

¹H NMR (400 MHz, CDCl₃): δ (ppm), 7.12 (t, 1H), 6.33 (t, 2H), 6.30 (s, 1H), 3.24 (t, 2H), 3.03 (t, 2H), 2.92 (s, 6H), 2.88 (d, 2H), 2.64 (t, 4H), 2.44 (t, 2H), 1.95 (m, 3H), 1.67 (m, 8H), 1.32-1.01 (m, 6H); MS (APCI): m/z 437.5 (MH⁺; 100%).

EXAMPLE 31

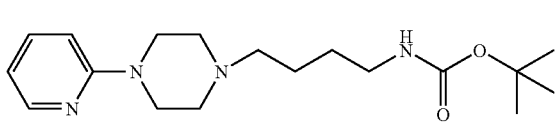

3HCl

Reaction of the product of Preparation 29 and hydrogen chloride in ether as described in Example 2 gave the desired white solid product, a salt of the product of Preparation 29.

¹H NMR (400 MHz, CD₃OD): δ (ppm), 7.49 (t, 1H), 7.34 (m, 1H), 7.19 (m, 2H), 4.02 (t, 2H), 3.72 (t, 2H), 3.70 (t, 6H), 3.12 (s, 6H), 3.13 (t, 2H), 2.95 (d, 2H), 1.93 (m, 5H), 1.74 (m, 4H), 1.44-1.01 (m, 6H); MS (APCI): m/z 437.5 (MH⁺; 100%).

Preparation 30

Reaction of 1-pyridin-2-yl-piperazine and the product of Preparation 5 as described in Example 1 gave the desired compound.

¹H NMR (400 MHz, CDCl₃): δ (ppm), 8.20-8.18(m, 1H), 7.50-7.45(m, 1H), 6.66-6.61(m, 2H), 5.40(sb, 1H), 3.58-3.56

(m, 4H), 3.16(m, 2H), 2.57-2.54(m, 4H), 2.40(t, 2H), 1.60-1.56(m, 4H), 1.43(s, 9H); MS (APCI): m/z 335 (MH+; 100%).

Preparation 31

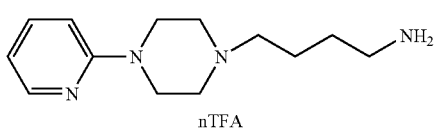

nTFA

Reaction of the product of Preparation 30 and TFA as described in Preparation 7 gave the desired product.

¹H NMR (400 MHz, CD₃OD): δ (ppm), 8.15-8.13(m, 1H), 7.84-7.80(m, 1H), 7.13(d, 1H), 6.95(t, 1H), 3.92-3.84(m, 4H), 3.48-3.40(m, 4H), 3.24-322(m, 2H), 3.00(t, 2H), 1.90-1.84(m, 2H), 1.76-1.72(m, 2H); MS (APCI): m/z 235 (MH+; 100%).

Preparation 32

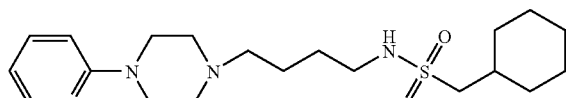

Reaction of cyclohexyl-methanesulfonyl chloride and the product of Preparation 31 as described in Preparation 8 gave the desired product, C-Cyclohexyl-N-[4-(4-pyridin-2-yl-piperazin-1-yl)-butyl]-methanesulfonamide.

¹H NMR (400 MHz, CDCl₃): δ (ppm), 8.19-8.18 (m, 1H), 7.50-7.46 (m, 1H), 6.66-6.61 (m, 2H), 3.61-3.59(m, 4H), 3.10(t, 2H), 2.86(d, 2H), 2.60-2.58(m, 4H), 2.44(t, 2H), 11.96-1.92(m, 3H), 1.71-1.62(m, 7H), 1.30-1.03(m, 5H); MS (APCI): m/z 395 (MH+; 100%).

EXAMPLE 32

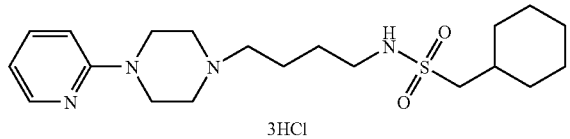

3HCl

Reaction of the product of Preparation 32 and hydrogen chloride in ether as described in Example 2 gave the desired white solid product, a salt of the product of Preparation 32.

¹H NMR (400 MHz, CD₃OD): δ (ppm), 8.21-8.17(m, 1H), 8.09(d, 1H), 7.52(d, 1H), 7.18(t, 1H), 4.41(d, 2H), 3.80-3.70 (m, 4H), 3.35-3.29(m, 4H), 3.12(t, 2H), 2.95(d, 2H), 1.96-1.90(m, 5H), 1.77-1.64(m, 5H), 1.42-1.11(m, 5H); MS (APCI): m/z 395 (MH+; 100%).

Preparation 33

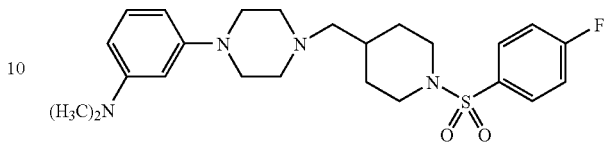

Reaction of dimethyl-(3-piperazin-1-yl-phenyl)-amine and 4-fluoro-benzenesulfonic acid 1-(4-fluoro-benzenesulfonyl)-piperidin-4-ylmethyl ester as described in Example 1 gave the desired product, (3-{4-[1-(4-Fluoro-benzenesulfonyl)-piperidin-4-ylmethyl]-piperazin-1-yl}-phenyl)-dimethyl-amine.

¹H NMR (400 MHz, CDCl₃): δ (ppm), 7.80-7.77 (m, 2H), 7.23-7.10 (m, 3H), 6.33-6.27 (m, 3H), 3.80 (d, 2H), 3.14 (t, 4H), 2.92 (s, 6H), 2.50 (t, 4H), 2.27 (t, 2H), 2.20 (d, 2H), 1.85 (d, 2H), 1.50-1.42 (m, 1H), 1.34-1.27 (m, 2H); MS (APCI): m/z 461 (MH+; 100%).

EXAMPLE 33

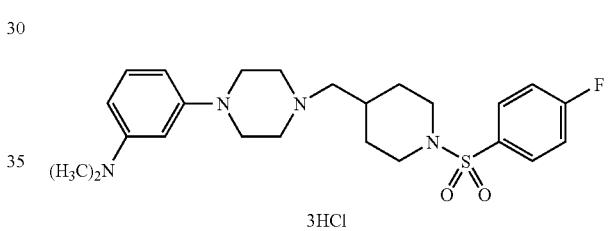

3HCl

Reaction of the product of Preparation 33 and hydrogen chloride in ether as described in Example 2 gave the desired white solid product, a salt of the product of Preparation 33.

¹H NMR (400 MHz, CDCl₃): δ (ppm), 10.78(sb, 1H), 7.92-7.88(m, 2H), 7.58(t, 2H), 7.39-7.36(m, 1H), 7.20-6.90 (m, 3H), 3.86(d, 2H), 3.71-3.34(m, 6H), 3.10(m, 9H), 2.31(t, 2H), 2.03-1.95(m, 3H), 1.37-1.30(m, 3H); MS (APCI): m/z 461 (MH+; 100%).

Preparation 34

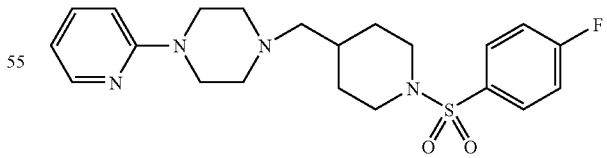

Reaction of 1-pyridin-2-yl-piperazine and 4-fluoro-benzenesulfonic acid 1-(4-fluoro-benzenesulfonyl)-piperidin-4-ylmethyl ester as described in Example 1 gave the desired product, 1-[1-(4-Fluoro-benzenesulfonyl)-piperidin-4-ylmethyl]-4-pyridin-2-yl-piperazine.

¹H NMR (400 MHz, CDCl₃): δ (ppm), 8.01 (d, 1H), 7.91 (d, 1H), 7.77 (t, 2H), 7.62 (d, 1H), 7.02 (t, 2H), 6.95 (t, 1H), 3.75 (t, 4H), 3.41 (t, 2H), 3.22 (t, 2H), 3.13 (t, 2H), 2.21 (t, 2H), 1.77 (m, 3H), 1.39 (m, 4H); MS (APCI): m/z 419.6 (MH+; 100%).

EXAMPLE 34

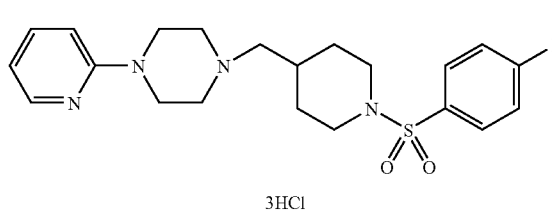

3HCl

Reaction of the product of Preparation 34 and hydrogen chloride in ether as described in Example 2 gave the desired white solid product, a salt of the product of Preparation 34.

$^1$HNMR (400 MHz, CD$_3$OD): (ppm), 8.16 (t, 1H), 8.08 (d, 1H), 7.85 (t, 2H), 7.50 (d, 1H), 7.36 (t, 2H), 7.15 (t, 1H), 3.83 (t, 4H), 3.35 (t, 2H), 3.25 (t, 2H), 3.17 (t, 2H), 2.36 (t, 2H), 1.98 (m, 3H), 1.43 (m, 4H); MS (APCI): m/z 419.6 (MH+; 100%).

Preparation 35

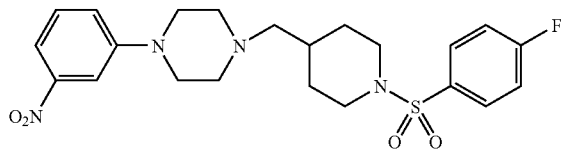

Reaction of 1-(3-nitro-phenyl)-piperazine and 4-fluoro-benzenesulfonic acid 1-(4-fluoro-benzenesulfonyl)-piperidin-4-ylmethyl ester as described in Example 1 gave the desired compound.

$^1$H NMR (400 MHz, CD$_3$OD): δ (ppm), 7.81-7.77(m, 2H), 7.69-7.63(m, 2H), 7.36(t, 1H), 7.24-7.15(m, 3H), 3.81(d, 2H), 3.25-3.22(m, 4H), 2.53-2.51(m, 4H), 2.30-2.21(m, 4H), 1.86-1.83(m, 2H), 1.49-1.44(m, 1H), 1.35-1.25(m, 2H); MS (APCI): m/z 363 (MH+; 100%).

Preparation 36

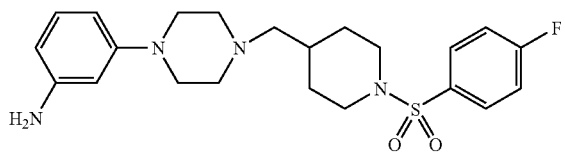

Reaction of the product of Preparation 35 and tin chloride as described in Preparation 2 gave the desired product.

$^1$H NMR (400 MHz, CD$_3$OD): δ (ppm), 7.81-7.77(m, 2H), 7.28-7.20(m, 2H), 7.06-7.02(m, 1H), 6.35(d, 1H), 6.24-6.21 (m, 2H), 3.80(d, 2H), 3.60(sb, 2H), 3.19(m, 4H), 2.39(m, 4H), 2.29-2.19(m, 4H), 1.85(d, 2H), 1.47(m, 1H), 1.35-1.28 (m, 2H); MS (APCI): m/z 433 (MH+; 100%).

Preparation 37

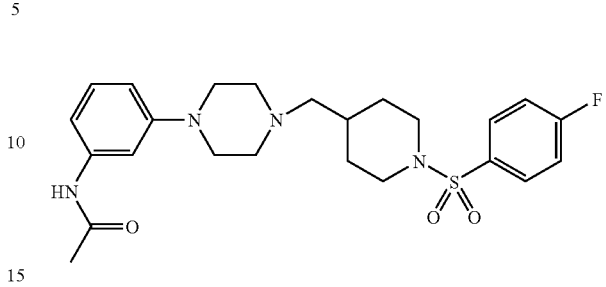

Reaction of the product of Preparation 36 and acetyl chloride in dichloromethane as described in Example 3 gave the desired product, N-(3-{4-[1-(4-Fluoro-benzenesulfonyl)-piperidin-4-ylmethyl]-piperazin-1-yl}-phenyl)-acetamide, as a white solid.

$^1$H NMR (400 MHz, CDCl$_3$): δ (ppm), 7.80-7.76(m, 2H), 7.32-7.13(m, 5H), 6.78(d, 1H), 6.63(d, 1H), 3.79(d, 2H), 3.14(t, 4H), 2.47(t, 4H), 2.28-2.10(m, 7H), 1.83(d, 2H), 1.47-1.43(m, 1H), 1.33-1.23(m, 2H); MS (APCI): m/z 457 (MH+; 100%).

EXAMPLE 35

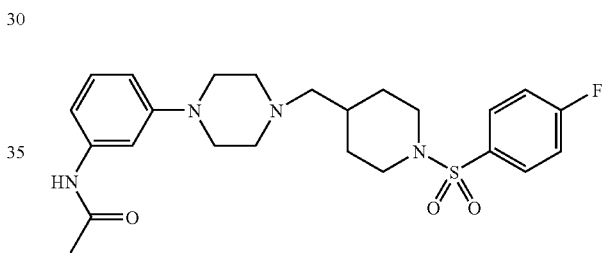

3HCl

Reaction of the product of Preparation 37 and hydrogen chloride in ether as described in Example 2 gave the desired white solid product, a salt of the product of Preparation 37.

$^1$H NMR (400 MHz, CD$_3$OD): δ (ppm), 7.88-7.84(m, 2H), 7.48-7.5(sb 1H), 7.37(t, 2H), 7.22(t, 1H), 6.95(d, 1H), 6.77(d, 1H), 3.81(t, 4H), 3.64(d, 2H), 3.26-3.13(m, 6H), 2.37(t, 2H), 2.11(s, 3H), 1.91(d, 2H), 1.43-1.37(m, 3H); MS (APCI): m/z 457 (MH+; 100%).

Preparation 38

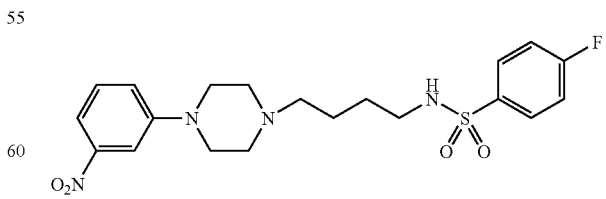

Reaction of 1-(3-nitro-phenyl)-piperazine and 4-fluoro-benzenesulfonic acid 4-(4-fluoro-benzenesulfonylamino)-butyl ester as described in Example 1 gave the desired compound.

$^1$H NMR (400 MHz, CDCl$_3$): δ (ppm), 7.85 (m, 2H), 7.75-7.63 (m, 2H), 7.22-7.06 (m, 4H), 3.38 (m, 4H), 2.95 (m, 2H), 2.45 (m, 4H), 2.05 (m, 1H), 1.61 (m, 4H); MS (APCI): m/z 437 (MH$^+$; 100%).

Preparation 39

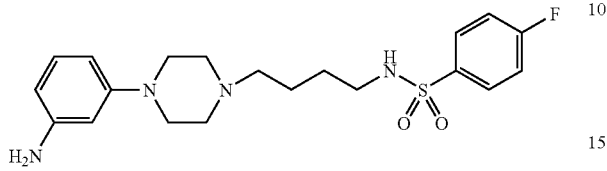

Reaction of the product of Preparation 38 and tin chloride as described in Preparation 2 gave the desired product.

$^1$H NMR (400 MHz, CDCl$_3$): δ (ppm), 7.95 (m, 2H), 7.45-6.95 (m, 4H), 6.51-6.19 (m, 2H), 3.95-2.83 (m, 8H), 2.65-2.31 (m, 7H), 1.61 (m, 4H); MS (APCI): m/z 407 (MH$^+$; 100%).

Preparation 40

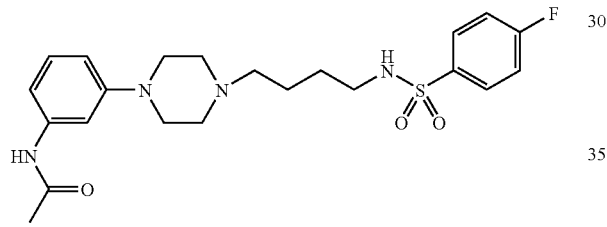

Reaction of the product of Preparation 39 and acetyl chloride in dichloromethane as described in Example 3 gave the desired product, N-(3-{4-[4-(4-Fluoro-benzenesulfonylamino)-butyl]-piperazin-1-yl}-phenyl)-acetamide, as a white solid.

$^1$H NMR (400 MHz, CDCl$_3$): δ (ppm), 7.45-7.16 (m, 4H), 6.81 (d, 2H), 6.65 (d, 2H), 3.48 (s, 1H), 3.28 (m, 4H), 2.95 (m, 2H), 2.62 (m, 5H), 2.35 (m, 2H), 2.08 (s, 3H), 1.65 (m, 4H); MS (APCI): m/z 449 (MH$^+$; 100%).

EXAMPLE 36

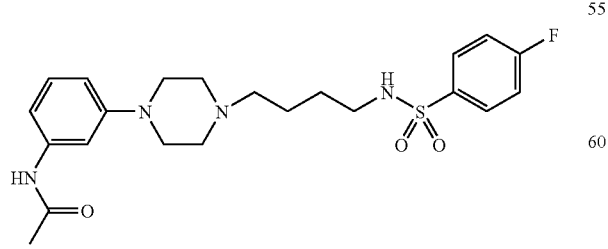

Reaction of the product of Preparation 40 and hydrogen chloride in ether as described in Example 2 gave the desired white solid product, a salt of the product of Preparation 40.

$^1$H NMR (400 MHz, CD$_3$OD): δ (ppm), 7.99 (m, 2H), 7.61-7.45 (m, 2H) 7.01 (d, 2H), 6.81 (d, 2H), 5.01 (bs, 4H), 3.99 (m, 1H), 3.75 (m, 1H), 3.45-3.21 (m, 8H), 2.18 (s, 3H), 2.01 (m, 2H), 1.89-1.65 (m, 4H); MS (APCI): m/z 449 (MH$^+$; 100%).

Preparation 41

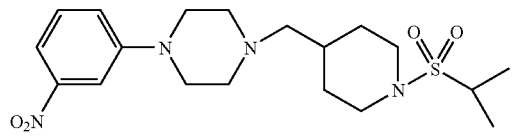

Reaction of 1-(3-nitro-phenyl)4-piperidin-4-ylmethyl-piperazine TFA salt and propane-2-sulfonyl chloride as described in Preparation 8 gave the desired product.

$^1$H NMR (400 MHz, CDCl$_3$): δ (ppm), 7.89-7.02(m, 4H), 3.90-1.09(m, 26H); MS (APCI): m/z 411 (MH$^+$; 100%).

Preparation 42

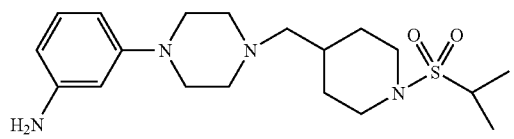

Reaction of the product of Preparation 41 and tin chloride as described in Preparation 2 gave the desired product.

$^1$H NMR (400 MHz, CDCl$_3$): δ (ppm), 7.92-7.10(m, 4H), 3.98-1.11 (m, 26 H); MS (APCI): m/z 411 (MH$^+$; 100%).

Preparation 43

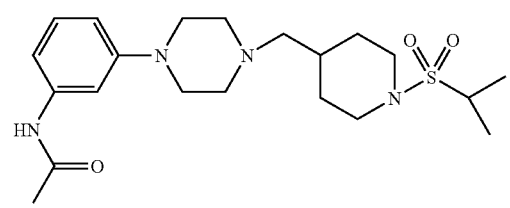

Reaction of the product of Preparation 42 and acetyl chloride in dichloromethane as described in Example 3 gave the desired product as a white solid.

$^1$H NMR (400 MHz, CDCl$_3$): δ (ppm), 7.40-6.60(m, 4H), 3.99-1.20 (m, 29 H); MS (APCI): m/z 423 (MH$^+$; 100%).

EXAMPLE 37

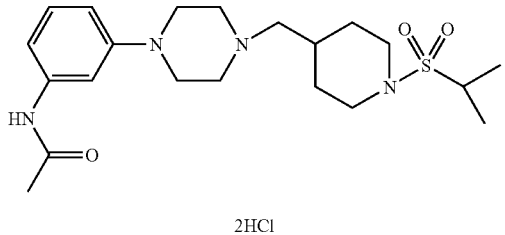

2HCl

Reaction of the product of Preparation 43 and hydrogen chloride in ether as described in Example 2 gave the desired white solid product, N-(3-{4-[1-(Propane-2-sulfonyl)-piperidin-4-ylmethyl]-piperazin-1-yl}-phenyl)-acetamide.

$^1$H NMR (400 MHz, CDCl$_3$): δ (ppm), 7.50-6.80(m, 4H), 4.00-1.25 (m, 29 H); MS (APCI): m/z 423 (MH$^+$; 100%).

Preparation 44

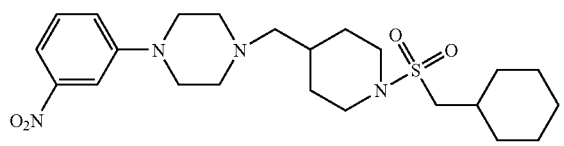

Reaction of 1-(3-nitro-phenyl)-4-piperidin-4-ylmethyl-piperazine TFA salt and cyclohexyl-methanesulfonyl chloride as described in Preparation 8 gave the desired product.

$^1$H NMR (400 MHz, CDCl$_3$): δ (ppm), 7.90-7.20(m, 4H), 3.90-0.90 (m, 32 H); MS (APCI): m/z 465 (MH$^+$; 100%).

Preparation 45

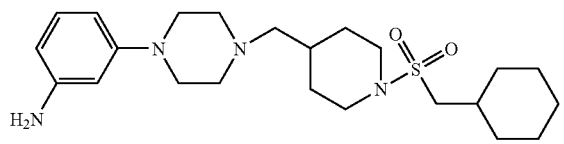

Reaction of the product of Preparation 44 and tin chloride as described in Preparation 2 gave the desired product.

$^1$H NMR (400 MHz, CDCl$_3$): δ (ppm), 7.79-6.20(m, 4H), 4.00-1.00 (m, 32 H); MS (APCI): m/z 435 (MH$^+$; 100%).

Preparation 46

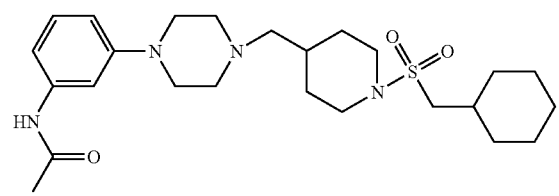

Reaction of the product of Preparation 45 and acetyl chloride in dichloromethane as described in Example 3 gave the desired product, N-{3-[4-(1-Cyclohexylmethanesulfonyl-piperidin-4-ylmethyl)-piperazin-1-yl]-phenyl}-acetamide, as a white solid.

$^1$H NMR (400 MHz, CDCl$_3$): δ (ppm), 7.26-6.70(m, 4H), 3.79-1.05 (m, 35 H); MS (APCI): m/z 477 (MH$^+$; 100%).

EXAMPLE 38

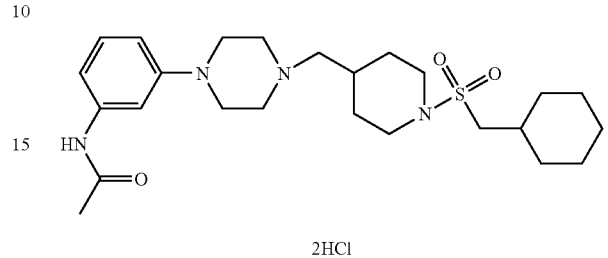

2HCl

Reaction of the product of Preparation 46 and hydrogen chloride in ether as described in Example 2 gave the desired white solid product, a salt of the product of Preparation 46.

$^1$H NMR (400 MHz, CDCl$_3$): δ (ppm), 7.50-6.79(m, 4H), 3.90-1.10 (m, 35 H); MS (APCI): m/z 477 (MH$^+$; 100%).

EXAMPLE 39

Activity of Arylpiperazinyl Sulfonamide Compounds

Arylpiperazinyl sulfonamide compounds of the invention were made according to the synthesis noted above, and their activity and selectivity was determined. These compounds are 4-Methyl-N-{4-[4-(3-nitro-phenyl)-piperazin-1-yl]-butyl}-benzenesulfonamide; 4-Methyl-N-{4-[4-(3-nitro-phenyl)-piperazin-1-yl]-butyl}-benzenesulfonamide HCl salt; Cyclopropanecarboxylic acid (3-{4-[4-(toluene-4-sulfonylamino)-butyl]-piperazin-1-yl}-phenyl)-amide; N-(3-{4-[4-(Toluene-4-sulfonylamino)-butyl]-piperazin-1-yl}-phenyl)-butyramide; 2,2-Dimethyl-N-(3-{4-[4-(toluene-4-sulfonylamino)-butyl]-piperazin-1-yl}-phenyl)-propionamide; N-(3-{4-[4-(Toluene-4-sulfonylamino)-butyl]-piperazin-1-yl}-phenyl)-isobutyramide; N-{4-[4-(3-Ethanesulfonylamino-phenyl)-piperazin-1-yl]-butyl}-4-methyl-benzenesulfonamide; 4-Methyl-N-(4-{4-[3-(propane-2-sulfonylamino)-phenyl]-piperazin-1-yl}-butyl)-benzenesulfonamide; 4-Methyl-N-{4-[4-(3-nitro-phenyl)-piperazin-1-yl]-butyl}-benzenesulfonamide; 4-Methyl-N-[4-(4-pyridin-2-yl-piperazin-1-yl)-butyl]-benzenesulfonamide; N-{4-[4-(2-Methoxy-5-nitro-phenyl)-piperazin-1-yl]-butyl}-4-methyl-benzenesulfonamide; 4-Methyl-N-[4-(4-pyrimidin-2-yl-piperazin-1-yl)-butyl]-benzenesulfonamide; N-{4-[4-(3-Methoxy-phenyl)-piperazin-1-yl]-butyl}-4-methyl-benzenesulfonamide; N-{4-[4-(3-Ethanesulfonylamino-phenyl)-piperazin-1-yl]-butyl}-4-methyl-benzenesulfonamide; N-{4-[4-(3-Methanesulfonylamino-phenyl)-piperazin-1-yl]-butyl}-4-methyl-benzenesulfonamide; 4-Methyl-N-{4-[4-(3-pyrazin-2-yl-phenyl)-piperazin-1-yl]-butyl}-benzenesulfonamide; and N-[4-(4-Biphenyl-3-yl-piperazin-1-yl)-butyl]-4-methyl-benzenesulfonamide, N-[4-(4-Biphenyl-3-yl-piperazin-1- yl)-butyl]-4-methyl-benzenesulfonamide, 4-Methyl-N-[4-(4-phenyl-piperazin-1-yl)-butyl]-benzenesulfonamide, C-Cyclohexyl-N-{4-[4-(2-methoxy-phenyl)-piperazin-1-yl]-butyl}-methanesulfonamide, N-(3-{4-[4-(Toluene-4-sulfonylamino)-butyl]-piperazin-1-yl}-phenyl)-acetamide, N-(3-{4-[4-(Toluene-4-sulfonylamino)-butyl]-piperazin-1-yl}-phenyl)-propionamide, (3-{4-[1-(4-Fluoro-benzenesulfonyl)-piperidin-4-ylmethyl]-piperazin-1-yl}-phenyl)-dimethyl-amine, 1-[1-(4-Fluoro-benzenesulfonyl)-piperidin-4-ylmethyl]-4-pyridin-2-yl-piperazine, C-Cyclohexyl-N-{4-[4-(3-dimethylamino-phenyl)-piperazin-1-yl]-butyl}-methanesulfonamide, C-Cyclohexyl-N-[4-(4-pyridin-2-yl-piperazin-1-yl)-butyl]-methanesulfonamide, N-(3-{4-[1-(4-Fluoro-benzenesulfonyl)-piperidin-4-ylmethyl]-piperazin-1-yl}-phenyl)-acetamide, N-(3-{4-[4-(4-Fluoro-benzenesulfonylamino)-butyl]-piperazin-1-yl}-phenyl)-acetamide, N-{3-[4-(4-Cyclohexylmethanesulfonylamino-butyl)-piperazin-1-yl]-phenyl}-acetamide, N-{3-[4-(1-Cyclohexylmethanesulfonyl-piperidin-4-ylmethyl)-piperazin-1-yl]-phenyl}-acetamide, Cyclopropanecarboxylic acid {3-[4-(4-cyclohexylmethanesulfonylamino-butyl)-piperazin-1-yl]-phenyl}-amide, N-(3-{4-[1-(Propane-2-sulfonyl)-piperidin-4-ylmethyl]-piperazin-1-yl}-phenyl)-acetamide, N-(3-{4-[4-(Propane-2-sulfonylamino)-butyl]-piperazin-1-yl}-phenyl)-acetamide, N-{3-[4-(4-Cyclohexanesulfonylamino-butyl)-piperazin-1-yl]-phenyl}-acetamide, N-(3-{4-[4-(Cyclohexylmethanesulfonyl-methyl-amino)-butyl]-piperazin-1-yl}-phenyl)-acetamide, N-(3-{4-[4-(2-Methyl-propane-1-sulfonylamino)-butyl]-piperazin-1-yl}-phenyl)-acetamide, N-[3-(4-{4-[Methyl-(2-methyl-propane-1-sulfonyl)-amino]-butyl}-piperazin-1-yl)-phenyl]-acetamide, N-(3-Piperazin-1-yl-phenyl)-acetamide, Cyclopropanecarboxylic acid (3-piperazin-1-yl-phenyl)-amide, and 1-(2-Methoxy-phenyl)-4-[1-(toluene-4-sulfonyl)-piperidin-3-ylmethyl]-piperazine.

These compounds were found to be active (e.g., at concentrations from about 0.1 to about 10 μM) and selective 5-HT$_{1A}$ modulators. Test data is shown in Table 1. The compounds accordingly are expected to be useful as 5-HT$_{1A}$ receptor modulators, e.g., in the treatment of a wide variety of clinical conditions which are characterized by serotonin excess or absence, e.g., serotonergic hypofunction or hyperfunction. Such conditions include eating disorders, schizophrenia, neuralgia, and addiction disorders; obsessive compulsive disorders, panic disorders, sexual dysfunctions caused by the central nervous system and disturbances in sleep and the absorption of food, alcoholism, pain, memory deficits, unipolar depression, dysthymia, bipolar depression, treatment-resistant depression, depression in the medically ill, panic disorder, obsessive-compulsive disorder, eating disorders, social phobia, premenstrual dysphoric disorder, mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, e.g., specific animal phobias, social phobias, stress disorders including post-traumatic stress disorder and acute stress disorder, and generalized anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delirium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple etiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delirium, withdrawal delirium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and post-therapeutic neuralgia, trigeminal neuralgia, segmental or intercostal neuralgia and other neuralgias; and cerebral vascular disorders due to acute or chronic cerebrovascular damage such as cerebral infarction, subarachnoid hemorrhage or cerebral edema.

TABLE 1

| Compound | 5-HT$_{1A}$ (K$_i$) nM | α$_1$ % inhibition | α$_2$ % inhibition |
|---|---|---|---|
| 4-Methyl-N-{4-[4-(3-nitro-phenyl)-piperazin-1-yl]-butyl}-benzenesulfonamide | 125 | 56 | 14 |
| 4-Methyl-N-{4-[4-(3-nitro-phenyl)-piperazin-1-yl]-butyl}-benzenesulfonamide HCl | 105 | 61 | 23 |
| 4-Methyl-N-(4-{4-[3-(propane-2-sulfonylamino)-phenyl]-piperazin-1-yl}-butyl)-benzenesulfonamide | 78 | 15 | <10 |
| N-{4-[4-(3-Ethanesulfonylamino-phenyl)-piperazin-1-yl]-butyl}-4-methyl-benzenesulfonamide | 141 | 47 | 14 |
| 4-Methyl-N-[4-(4-phenyl-piperazin-1-yl)-butyl]-benzenesulfonamide | 40 | 98 | 90 |
| N-(3-{4-[4-(Toluene-4-sulfonylamino)-butyl]-piperazin-1-yl}-phenyl)-isobutyramide | 47 | 47 | 12 |
| N-{4-[4-(3-Methanesulfonylamino-phenyl)- | 46 | 51 | 21 |

TABLE 1-continued

| Compound | 5-HT$_{1A}$ (K$_i$) nM | α$_1$ % inhibition | α$_2$ % inhibition |
|---|---|---|---|
| piperazin-1-yl]-butyl}-4-methyl-benzenesulfonamide | | | |
| 4-Methyl-N-[4-(4-pyrimidin-2-yl-piperazin-1-yl)-butyl]-benzenesulfonamide | 26 | <10 | 16 |
| 4-Methyl-N-[4-(4-pyrimidin-2-yl-piperazin-1-yl)-butyl]-benzenesulfonamide HCl | 30 | 35 | 17 |
| Cyclopropanecarboxylic acid (3-{4-[4-(toluene-4-sulfonylamino)-butyl]-piperazin-1-yl}-phenyl)-amide HCl | 21 | 40 | 15 |
| N-{4-[4-(2-Methoxy-5-nitro-phenyl)-piperazin-1-yl]-butyl}-4-methyl-benzenesulfonamide | 415 | 28 | 0 |
| N-(3-{4-[4-(Toluene-4-sulfonylamino)-butyl]-piperazin-1-yl}-phenyl)-butyramide | 56 | 12 | 12 |
| 2,2-Dimethyl-N-(3-{4-[4-(toluene-4-sulfonylamino)-butyl]-piperazin-1-yl}-phenyl)-propionamide | 1360 | 0 | 11 |
| 4-Methyl-N-[4-(4-pyridin-2-yl-piperazin-1-yl)-butyl]-benzenesulfonamide | 10 | 81 | 63 |
| 4-Methyl-N-[4-(4-pyridin-2-yl-piperazin-1-yl)-butyl]-benzenesulfonamide HCl | 7.7 | 80 | 72 |
| 1-(2-Methoxy-phenyl)-4-[1-(toluene-4-sulfonyl)-piperidin-3-ylmethyl]-piperazine | 9.2 | 74 | 57 |
| C-Cyclohexyl-N-{4-[4-(2-methoxy-phenyl)-piperazin-1-yl]-butyl}-methanesulfonamide | 3.9 | 98 | 86 |
| C-Cyclohexyl-N-{4-[4-(2-methoxy-phenyl)-piperazin-1-yl]-butyl}-methanesulfonamide HCl | 3.2 | 98 | 87 |
| N-(3-{4-[4-(Toluene-4-sulfonylamino)-butyl]-piperazin-1-yl}-phenyl)-acetamide | 16 | 22 | 43 |
| N-(3-{4-[4-(Toluene-4-sulfonylamino)-butyl]-piperazin-1-yl}-phenyl)-acetamide HCl | 6.8 | 10 | 15 |
| N-(3-{4-[4-(Toluene-4-sulfonylamino)-butyl]-piperazin-1-yl}-phenyl)-propionamide | 213 | 0 | 31 |
| (3-{4-[1-(4-Fluoro-benzenesulfonyl)-piperidin-4-ylmethyl]-piperazin-1-yl}-phenyl)-dimethylamine HCl | 507 | 74 | 0 |
| 1-[1-(4-Fluoro-benzenesulfonyl)-piperidin-4-ylmethyl]-4-pyridin-2-yl-piperazine HCl | 21 | 42 | 68 |
| C-Cyclohexyl-N-{4-[4-(3-dimethylamino-phenyl)-piperazin-1-yl]-butyl}-methanesulfonamide HCl | 110 | 85 | 25 |
| C-Cyclohexyl-N-[4-(4-pyridin-2-yl-piperazin-1-yl)-butyl]-methanesulfonamide HCl | 6.5 | 81 | 51 |
| N-(3-{4-[1-(4-Fluoro-benzenesulfonyl)-piperidin-4-ylmethyl]-piperazin-1-yl}-phenyl)-acetamide HCl | 13 | 49 | <10 |
| N-(3-{4-[4-(4-Fluoro-benzenesulfonylamino)-butyl]-piperazin-1-yl}-phenyl)-acetamide | 18 | 39 | <10 |
| N-{3-[4-(4-Cyclohexylmethanesulfonylamino-butyl)-piperazin-1-yl]-phenyl}-acetamide | 5.1-11 | <25 (K$_i$ = 1600 nM) | <10 |
| N-{3-[4-(1-Cyclohexylmethanesulfonyl-piperidin-4-ylmethyl)-piperazin-1-yl]-phenyl}-acetamide | 10 | 13 | <10 |
| Cyclopropanecarboxylic acid {3-[4-(4-cyclohexylmethanesulfonylamino-butyl)-piperazin-1-yl]-phenyl}-amide | 8.9 | 22 | <10 |
| N-(3-{4-[1-(Propane-2-sulfonyl)-piperidin-4-ylmethyl]-piperazin-1-yl}-phenyl)-acetamide | 112 | <10% | <10 |
| N-(3-{4-[4-(Propane-2-sulfonylamino)-butyl]-piperazin-1-yl}-phenyl)-acetamide | 24 | <10 | 12 |
| N-{3-[4-(4-Cyclohexanesulfonylamino-butyl)-piperazin-1-yl]-phenyl}-acetamide | 40 | <10 | 12 |
| N-(3-{4-[4-(Cyclohexylmethanesulfonyl-methyl-amino)-butyl]-piperazin-1-yl}-phenyl)-acetamide | 1.3 | 37 | 47 (K$_i$ = 616 nM) |
| N-(3-{4-[4-(2-Methyl-propane-1-sulfonylamino)-butyl]-piperazin-1-yl}-phenyl)-acetamide | 11 | 5 | 0 |
| N-(3-Piperazin-1-yl-phenyl)-acetamide HCl | 2.9 | 0 | 35 |
| Cyclopropanecarboxylic acid (3-piperazin-1-yl-phenyl)-amide HCl | 4.6 | 0 | 14 |

To further demonstrate the suitability of compounds of the invention as 5-HT agonists, e.g., 5-HT$_{1A}$ agonists, an arylpiperazinyl sulfonamide compound of the invention, N-{3-[4-(4-Cyclohexylmethanesulfonylamino-butyl)-piperazin-1-yl]-phenyl}-acetamide ("Compound A"), was evaluated in laboratory animals using several standard tests, which are set forth below.

EXAMPLE 40

Activity of a Representative Arylpiperazinyl Sulfonamide Compound In Vivo—Anxiety and Motor Activity Assessments In this experiment, a compound of the invention, N-{3-[4-(4-Cyclohexylmethanesulfonylamino-butyl)-piperazin-1-yl]-phenyl}-acetamide HCl ("Compound A") was evaluated in animal models of anxiety and motor activity in mice. The effect of the compound was investigated after acute oral administration. Compound A administered orally in mice exhibited an anxiolytic like-effect measured behaviorally and physiologically by the elevated plus-maze and the stress-induced hyperthermia test, respectively. The highest dose of Compound A (i.e., 20 mg/kg) was effective in the stress-induced hyperthermia test whereas a lower dose (i.e., 3 mg/kg) was effective in the elevated plus-maze test. This may suggest that different doses of the compound may target different aspects of the stress-induced anxiety.

As opposed to the reference compound chlordiazepoxide and buspirone, Compound A did not alter general motor activity as demonstrated by a lack of effect in the open field and the elevated plus-maze, suggesting that Compound A may exhibit a preferable profile in these models.

Material and Methods

Animals

Young adult male C57B16/J mice from Jackson Laboratory, Bar Harbor, Me. were used in the Elevated Plus Maze; 129 svev mice from Taconic, Germantown, N.Y. were used in the Stress-induced Hyperthermia, Open Field, and the Tail Suspension tests, and DBA/2J mice from Jackson Laboratory, Bar Harbor, Me. were used in the Forced Swim test. All mice were received at the age of 6 weeks and were assigned unique identification numbers. Animals were housed 4 per cage in polycarbonate cages with filter tops, cagemate identification maintained by tail marks. Animals were acclimated for 7 days and given food and water ad libitum. Mice were examined prior to initiation of the study at 8 weeks of age to assure adequate health and suitability. During the course of the study, 12-hour light/12-hour dark cycles were maintained with the light on at 7:00 a.m. The room temperature was maintained between 20 and 23° C. with a relative humidity maintained between 30% and 70%. Chow and water were provided ad libitum.

In each test, animals were randomly assigned across treatment groups and balanced by cage number. Ten animals were used in each treatment group. Mice for the Open Field and Stress-induced hyperthermia studies were handled once daily for 2 consecutive days prior to the testing. Mice assigned to the Elevated plus maze experiment were not handled to increase the stress level at the time of the testing.

Drugs

The following compounds were used for this study:

Test Compound:
N-{3-[4-(4-Cyclohexylmethanesulfonylamino-butyl)-piperazin-1-yl]-phenyl}-acetamide HCl ("Compound A") (1, 3, and 20 mg/kg) (Lot # DC-006-022-L2, $C_{23}H_{38}N_4O_3S_2HCl$, doses expressed in mg of salt).

Reference Compounds:
Buspirone (3, 10 and 20 mg/kg, Sigma, Lot # 101H0402)
Sertraline Hydrocloride salt (5, 20 mg/kg, received as a gift from Pfizer CP-51,974-01, Lot #047451-029-19)
Chlordiazepoxide (CDP, 10 mg/kg, Sigma, Lot # 94H1023).

All compounds were dissolved in sterile injectable water, which served as the vehicle control. All solutions were prepared on the day of the experiments. Compound A were given to animals orally (PO) in all tests in a volume of 10 ml/kg body weight; all reference compounds were given to animals intraperitoneally (IP) to the exception of Buspirone which was given orally in the elevated plus maze (EPM) test and the open field (OF) tests. In all tests except for the tail suspension (TS) test, drugs were administered acutely; in the TS test, Compound A was administered once daily for 3 days (test day inclusive) prior to testing. Thirty minutes pretreatment time was used in all tests except for SIH in which case compounds were given to the animals one hr before the test.

Methods

All experiments were carried out in ambient temperature under light cycle between 9:00 a.m. and 5:00 p.m. during a forty-day period. Results were recorded automatically and processed by microcomputer; or manually on individual data sheets, transcribed and verified item by item.

Elevated Plus Maze (EPM)

The elevated plus maze is a test commonly used to assess anxiety in rodents. The maze consists of two closed arms (l×w×h: 15 cm×6 cm×30 cm) and two open arms (6 cm w×30 cm l) forming a cross, with a square center platform (6×6 cm). Rodents naturally fear open spaces and tend to spend more time in the closed arms. Anxiolytics will attenuate this fear of open spaces and will increase the number of time spent in open arms. All visible surfaces are made of a black acrylic. Each arm of the maze is placed on a support column 50 cm above the floor. The light intensity was ~100 lux above the open arms and ~70 lux above the closed arms. Animals were brought to the experimental room at least 1 hr before the test in the home cage (food and water available). Mice were placed in the center of the elevated plus maze facing an open arm, tested once, one at a time for a 5 min test. The time in the open/closed arms and the number of entries in the open/closed arms were recorded via video camera and used as a measure of anxiety. Mice were returned to the home cage after testing and then to the colony room.

Stressed Induced Hyperthermia (SIH)

Mice have a natural hyperthermic response to stress, which has been proposed as a measure of stress-induced anxiety (Olivier, Zethof, Ronken & van der Heyden, *European Journal of Pharmacology* 342(2-3):177-82, 1998). Anxiolytics are known to decrease this hyperthermic response to stress. This test involves two measures of rectal temperature repeated in the same animal within a 10 min period. On the day prior to testing, animals were brought to the experimental room 1 hr prior to scheduled lights out and singly housed overnight with food and water ad libitum. On the morning of the experiment, animals were first injected with treatment compound or vehicle. One hr post treatment, the animal was removed from the holding cage and held in a supine position and had rectal temperature measured by using a rectal probe attached to a PhysiTemp thermometer (Fisher Scientific). For each animal tested, the rectal probe was cleaned with an alcohol pad and lubricated with sterile K-Y jelly and slowly inserted into the animal's rectum at a length of approximately 3-5 mm. The probe remained within the animal's rectum for approximately 5 sec or until body temperature reached stability, and the baseline rectal temperature (T1) was recorded. The animal was immediately placed back to the holding cage and after a 10-min interval a second rectal temperature (T2) was taken using the same procedure as T1. The animal was then returned to the home cage and at the completion of the experiment returned to the colony room.

Open Field (OF)

The open field activity monitor system (Med Associates, Inc.) measured general motor activity. The test was performed under normal lighting conditions (400 lux). Mice were brought into the experimental room and allowed at least 1 hr of acclimation. Thirty min after treatment, each mouse was placed into the testing enclosure (l×w×h: 27 cm×27 cm×20 cm) with an infrared beam array that automatically monitors the animal's activity. Eight animals of balanced treatment were tested at one time. The test session lasted 40 min and animals were returned to the home cages at the end of the session. The critical measures of this test includes locomotion (total distance traveled), rearing (vertical activity), number of center entries and percent time spent in the center area of the OF arena.

Statistical Analysis

All data were analyzed by comparing the groups treated with the test substance to the vehicle control or reference treated groups. Statistical analysis was performed by ANOVA followed by Fisher's post-hoc test where appropriate. P less than 0.05 were considered to be significantly different. Data are represented as the means and standard error to the mean (s.e.m).

Results

Elevated Plus Maze

The reference compound CDP and the test substance Compound A exhibited an anxiolytic-like effects as measured by an increase in the time spent in open arms and an increase in the number of entries into the open arms (FIGS. 1 and 2). Note that, in FIG. 1, an increase in Proportion of Open Arm Entries compared to Vehicle treatment represents an anxiolytic-like effect. *P<0.05 vs vehicle-treated group (water). ANOVA revealed significant main effect for Treatment (p=0.0029). Fisher's PLSD for paired comparison indicated that the anxiolytic reference compound CDP, but not buspirone, significantly increased percentage of entries into the open arms (p=0.011), an effect consistent with CDP's clinical anxiolytic effects. Compound A in 3 mg/kg dose induced a significant anxiolytic-like effect (p=0.039). Higher doses of Compound A (10 and 20 mg/kg) showed similar tendency but it did not reach statistical significance (p=0.279 and p=0.074, respectively). In FIG. 2, an increase in Open Arm Time compared to Vehicle treatment represents an anxiolytic-like effect. *P<0.05 vs vehicle-treated group (water). ANOVA revealed a significant effect for Treatment (p=0.04). Fisher's PLSD for paired comparison indicated that the anxiolytic reference compound CDP produced a nearly significant increase in Open Arm Time (p=0.0554); buspirone had no effect. Compound A in 3 mg/kg dose induced a significant anxiolytic-like effect (p=0.048). Higher doses of Compound A (10 and 20 mg/kg) showed similar tendency but it did not reach statistical significance (p=0.467 and p=0.543, respectively).

Buspirone, however, failed to produce a significant anxiolytic-like effect in the EPM. This lack of buspirone effect has been previously reported in the literature. The anxiolytic effect of Compound A was specific as the compound did not alter locomotor activity as measured by a lack of effect on the number of entries in the closed arms or total number of entries in the closed and open arms (FIGS. 3 and 4). In FIG. 3, *P<0.05 vs vehicle-treated group (water). ANOVA revealed significant effect for Treatment (p=0.0028). Fisher's PLSD for paired comparison indicated that the reference compound buspirone, but not CDP or Compound A, significantly decreased number of entries into the closed arms (p=0.00 12) at 20 mg/kg dose. In FIG. 4, note that an increase or a decrease in Total Entries compared to Vehicle treatment represents an increased or decreased locomotor activity. *p<0.05, **p<0.01 vs vehicle-treated group (water). ANOVA revealed a significant main effect for Treatment (p=0.0001). Follow-up Fisher's PLSD for paired comparison revealed a significant effect of CDP compared to Vehicle (p=0.021) indicating slight increase in motor activity. Highest dose of buspirone (20 mg/kg) resulted in a significant decrease in total number of entries (p=0.0014). Compound A did not alter total number of entries.

Therefore, Compound A did not affect locomotor activity in this test. Interestingly, CDP produced a slight increase whereas high dose of buspirone (20 mg/kg) resulted in a decrease in total number of entries.

Stress-Induced Hyperthermia

Both reference compound buspirone and Compound A exerted a dose-dependent anxiolytic-like effect as measured by a decrease in the hyperthermic response to stress at the high dose tested (i.e., 20 mg/kg). This effect was also accompanied by a change in basal rectal temperature (FIG. 5-6). This phenomenon may also be associated with an anxiolytic-like profile as it is commonly reported with clinically used anxiolytics. In FIG. 5, *p<0.05, **p<0.01 vs. vehicle-treated group (water). ANOVA revealed a significant effect of Treatment (p=0.0109). Follow-up Fisher's PLSD for paired comparison showed that buspirone (20 mg/kg) significantly decreased (p=0.044) basal rectal temperature. Similarly, Compound A in 20 mg/kg dose resulted in significant decrease (p=0.0023). Lower dose of the drug did not show significant effects (p=0.808 and p=0.326, for 1 and 3 mg/kg of Compound A, respectively). In FIG. 6, note the increase in rectal temperature in vehicle-treated animals (stress-induced hyperthermia) and the blocking effect of buspirone (20 mg/kg; P<0.05 vs vehicle-treated group) and Compound A (20 mg/kg; P<0.01 vs vehicle-treated group). ANOVA revealed significant effect of Treatment (p=0.0009). Follow-up Fisher's PLSD for paired comparison showed that buspirone (20 mg/kg) significantly decreased (p=0.024) stress-induced hyperthermia. Similarly, Compound A in 20 mg/kg dose resulted in significant decrease (p=0.0067). Lower dose of the drug did not show significant effects (p=0.618 and p=0.2911, for 1 and 3 mg/kg of Compound A, respectively).

Open Field

Compound A did not alter locomotor activity as measured by the total distance traveled (FIG. 7), the number of rearing (FIG. 8) and the distance traveled in the center (FIG. 9-11). In FIG. 7, time bins represent 5 min intervals with total testing time of 40 min. Bar graph represents cumulative total distance traveled during the period of 40 min. Repeated measures ANOVA revealed no significant main effect for Treatment (p=0.2736). However, a significant Distance X Treatment interaction was identified (p<0.0001). Follow-up Fisher's PLSD for paired comparison revealed no significant difference as compared to the Water-treated controls. In FIG. 8, ANOVA did not exhibit a significant effect for Treatment (p=0.087). Compound A did not alter vertical activity significantly in any of the doses used as opposed to Buspirone which decreased the number of rears. In FIG. 9, ANOVA revealed no significant main effect for Treatment (p=0.923) effects. These results indicated that neither buspirone nor Compound A alter percent distance traveled in the center. In FIG. 10, ANOVA revealed no significant main effect for Treatment (p=0.834) effects. These results indicated that neither buspirone nor Compound A alter percent time traveled in the center. In FIG. 11, time bins represent 5 min intervals with total testing time of 40 min. Bar graph represents cumulative total distance traveled during the period of 40 min. Repeated measures ANOVA revealed no significant main effect for Treatment (p=0.492) or Time X Treatment interaction (p=0.659). These results indicated that neither buspirone nor Compound A alter zone crossing activity (between periphery and center).

Discussion

The results of these studies are summarized in Table 2, below.

Overall these results suggest that Compound A exhibits a clear anxiolytic like-effect in the experimental conditions employed.

EXAMPLE 41

Activity of a Representative Arylpiperazinyl Sulfonamide Compound In Vivo—Hyperlocomotor Activity Assessments In this experiment, a compound of the invention, N-{3-[4-(4-Cyclohexylmethanesulfonylamino-butyl)-piperazin-1-yl]-phenyl}-acetamide HCl ("Compound A") administered orally decreased the hyperlocomotor activity observed in the Coloboma mice at the doses of 1 and 20 mg/kg. The effect was similar to the effect observed with d-Amphetamine. Overall, these results suggest that Compound A may normalize hyperactivity in the experimental conditions employed.

The Coloboma mutant mice are considered as an animal model of attention deficit hyperactivity disorder (ADHD) due to their spontaneous high level of hyperactivity. Indeed, hyperactivity syndromes are thought to account for a large proportion of children diagnosed with learning disabilities, therefore a great deal of attention has been focused on the causes and the treatment of hyperactivity in children.

TABLE 2

| Test | Ref. Cmp. | Compound A | | |
|---|---|---|---|---|
| Elevated Plus Maze | CDP/Buspirone | 3 mg/kg | 10 mg/kg | 20 mg/kg |
| Proportion Open Arm Entries | increase (CDP) | increase | no change | no change |
| Open Arm Time | increase (CDP) | increase | no change | no change |
| Closed Arm Entries | decrease (BUS, 20) | no change | no change | no change |
| Total Entries | increase (CDP) decrease (BUS, 20) | no change | no change | no change |
| Stress-Induced Hyperthermia | Buspirone | 1 mg/kg | 3 mg/kg | 20 mg/kg |
| Basal Rectal Temperature | decrease | no change | no change | decrease |
| Temperature Change | decrease | no change | no change | decrease |
| Open Field | Buspirone | 1 mg/kg | 3 mg/kg | 20 mg/kg |
| Total Distance (Horizontal) | no change | No change | no change | no change |
| Vertical Activity (Rearing) | decrease | No change | no change | no change |
| Percent Distance in Center | no change | No change | no change | no change |
| Percent Time in Center | no change | No change | no change | no change |
| Frequency of Zone Crosses | no change | No change | no change | no change |

In our experimental conditions, Compound A administered orally in mice exhibited an anxiolytic like-effect measured behaviorally and physiologically by the elevated plus-maze and the stress-induced hyperthermia test, respectively. The highest dose of Compound A (i.e., 20 mg/kg) was effective in the stress-induced hyperthermia test whereas a lower dose (i.e., 3 mg/kg) was effective in the elevated plus-maze test. This may suggest that different doses of the compound may target different aspects of the stress-induced anxiety. In other studies carried out under specific conditions, e.g., tail suspension and forced swim test, Compound A did not appear to have antidepressive properties.

As opposed to the reference compound chlordiazepoxide and buspirone, Compound A did not alter general motor activity as demonstrated by a lack of effect in the open field and the elevated plus-maze, suggesting that Compound A may exhibit a preferable profile in these models.

The mouse mutant Coloboma exhibits profound spontaneous locomotor hyperactivity resulting from a deletion mutation. This deletion encompasses several genes including Snap, which encodes SNAP-25, a nerve terminal protein involved in neurotransmitter release. In 1996, Hess et al. demonstrated that amphetamine, a clinically-used agent that normalize hyperactivity expressed in ADHD-affected children, markedly reduced the locomotor activity in Coloboma mice but increased the activity of control mice. When a transgene encoding SNAP-25 was bred into the Coloboma strain to complement the Snap deletion, the hyperactivity expressed by these mice was rescued, returning these corrected mice to normal levels of locomotor activity. Mill et al. (2002) also demonstrated in a linkage study that SNAP-25 may play a role in the genetic of etiology of ADHD although further work is required to confirm or reject this hypothesis. Altogether, these results supported the use of the Coloboma mice as a model to mimic hyperactivity in rodents.

In this experiment, the effect of the compound Compound A was investigated after acute oral administration. Three doses of the test compound was administered in the Coloboma mice and their spontaneous activity was measured using an Open Field test. d-Amphetamine was used as a positive reference compound.

Material and Methods

Animals

The mice used in the current study are the offspring of breeding pairs (C3H/HeSnj-Cm) originally purchased from Jackson Laboratory, Bar Harbor, Me. Of the 48 mice tested, 22 were male and 26 were female, at age between 12-20 weeks old. These animals were weaned at 21 days age and were housed in 2 to 4 littermates per cage in our animal facility where standard animal husbandry was maintained. The colony room was kept under 12-hour light/12-hour dark cycles with the lights on at 7:00 a.m. Temperature was maintained between 20 and 23° C. with a relative humidity maintained between 30% and 70%. Animals received food chow and water provided ad libitum.

Drugs

The following compounds were used for this study.

Test Compound:

N-{3-[4-(4-Cyclohexylmethanesulfonylamino-butyl)-piperazin-1-yl]-phenyl}-acetamide HCl ("Compound A") (1, 3, and 20 mg/kg) (Lot # DC-006-022-L2, $C_{23}H_{38}N_4O_3S_2$HCl, doses expressed in mg of salt).

Reference Compound:

d-Amphetamine (4 mg/kg, Sigma, Lot #60K1909)

All compounds were dissolved in sterile injectable water, which served as the vehicle control. All solutions were prepared on the day of the experiments. Compound A as well as its vehicle (water) was given to animals orally (PO) in a volume of 10 ml/kg body weight; the reference compound was given to animals intraperitoneally (IP). Thirty minutes pretreatment time was used for Compound A and vehicle whereas d-Amphetamine (AMPH) was given to animals 15 min before the test.

Methods

The study was conducted over two consecutive days with animals tested between 10:00 a.m. and 5:00 p.m. on each day. Gender and age were balanced across five treatment groups and the testing day. Eight to 10 animals were allocated per group. The results were recorded automatically and processed by microcomputer.

The open field activity monitor system (Med Associates, Inc.) measured general motor activity. The test was performed under normal lighting conditions (400 lux). Mice were brought into the experimental room and allowed at least 1 hr of acclimation followed by drug administration. After drug administration (i.e., 30 min after administration of Compound A or vehicle, and 15 min after administration of d-Amphetamine), each mouse was placed into the testing enclosure (l×w×h: 27 cm×27 cm×20 cm) with an infrared beam array that automatically monitors the animal's activity. Eight animals of balanced treatment were tested at one time. The test session lasted 40 min and animals were returned to the home cages at the end of the session. The critical measure of this test was the Distance Traveled.

Statistical Analysis

All data were analyzed by comparing the groups treated with the test substance to the vehicle control or reference treated groups. Statistical analysis was performed by ANOVA followed by Fisher's post-hoc test where appropriate. P less than 0.05 were considered to be significantly different. Data are represented as the means and standard error to the mean (s.e.m).

Results

Amphetamine significantly decreased locomotor activity as compared to the vehicle-treated group. Overall, the compound also significantly decreased the level of activity. Post-hoc analysis revealed that only the dose of 1 and 20 mg/kg of Compound A was significantly different from vehicle.

Time bins represent 5 min intervals with total testing time of 40 min. Bar graph represents cumulative total distance traveled during the period of 40 min. *$p<0.05$ vs. Water-treated controls.

Discussion

From the data above, it can be seen that Compound A administered orally decreased the hyperlocomotor activity observed in the Coloboma mice at the doses of I and 20 mg/kg. The effect was similar to the effect observed with d-Amphetamine.

As demonstrated in Example 3, Compound A does not appear to alter general motor activity as demonstrated by a lack of effect in the elevated plus-maze and the open field in normal C57B16/J mice and 129 svev mice, respectively. Therefore, it is unlikely that the present effect is related to a non-specific sedative effect.

Overall these results suggest that Compound A normalizes hyperactivity in the experimental conditions employed, and therefore is expected to be a useful drug for treating attention-deficit related conditions like ADD and ADHD.

The above examples demonstrate the suitability of compounds of the invention as 5-HT agonists and their predicted effectiveness in treating indications described herein, e.g., anxiety, ADD and ADHD.

Equivalents

Those skilled in the art will recognize, or be able to ascertain using no more than routine experimentation, numerous equivalents to the specific procedures described herein. Such equivalents are considered to be within the scope of the invention and are covered by the following claims. Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:

1. A method of treating generalized anxiety disorder, comprising administering to a patient in need thereof, in an amount effective to treat generalized anxiety disorder, a pharmaceutical composition comprising a compound of formula (I):

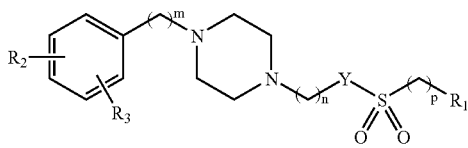

wherein
R₁ is unsubstituted alkyl or cycloalkyl;
R₂ and R₃ independently are hydrogen, nitro, lower alkoxy, or —NR₄R₅, provided that R₂ and R₃ are not both hydrogen;
R₄ and R₅ are independently H, lower alkyl; COR₆ or SO₂R₆, where R₆ is lower alkyl or cycloalkyl;
Y is NH, N(lower alkyl) or

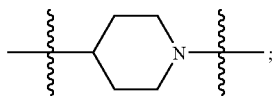

m is 0, 1, 2, 3, 4, 5, or 6;
n is 1, 2, 3, 4, 5, or 6;
p is 0, 1, 2, 3, or 4; or pharmaceutically acceptable salts thereof.

2. A method of treating attention deficit disorder, with or without hyperactivity, comprising administering to a patient in need thereof, a compound represented by formula (I):

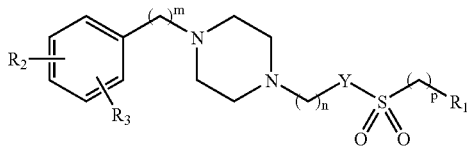

wherein
R₁ is unsubstituted alkyl or cycloalkyl;
R₂ and R₃ independently are hydrogen, nitro, lower alkoxy, or —NR₄R₅, provided that R₂ and R₃ are not both hydrogen;
R₄ and R₅ are independently H, lower alkyl; COR₆ or SO₂R₆, where R₆ is lower alkyl or cycloalkyl;
Y is NH, N(lower alkly) or

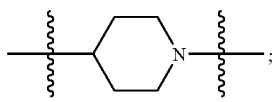

m is 0, 1, 2, 3, 4, 5, or 6;
n is 1, 2, 3, 4, 5, or 6;
p is 0, 1, 2, 3, or 4; or pharmaceutically acceptable salts thereof in an amount effective to treat attention deficit disorder.

3. A method of treating depression, comprising administering to a patient in need thereof, in an amount effective to treat depression, a pharmaceutical composition comprising a pharmaceutically acceptable carrier and compound of formula (I):

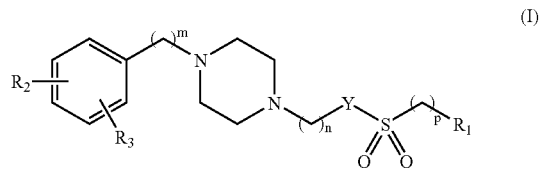

wherein
R₁ is unsubstituted alkyl or cycloalkyl;
R₂ and R₃ independently are hydrogen, nitro, lower alkoxy, or —NR₄R₅, provided that R₂ and R₃ are not both hydrogen;
R₄ and R₅ are independently H, lower alkyl; COR₆ or SO₂R₆, where R₆ is lower alkyl or cycloalkyl;
Y is NH, N(lower alkyl) or

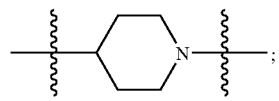

m is 0, 1, 2, 3, 4, 5, or 6;
n is 1, 2, 3, 4, 5, or 6;
p is 0, 1, 2, 3, or 4; or pharmaceutically acceptable salts thereof.

4. The method of claim 3, wherein the depression is selected from the group consisting of unipolar depression, dysthymia, bipolar depression, treatment-resistant depression, single episodic or recurrent major depressive disorders, and depression in the medically ill.

5. The method of claim 4, wherein the bipolar depression is selected from the group consisting of bipolar I disorder, bipolar II disorder and cyclothymic disorder.

6. The method of claim 3, wherein the amount of the compound administered is from about 0.01 to 30 mg/kg per day.

7. The method of claim 3, wherein the amount of the compound administered is from about 0.01 to 20 mg/kg per day.

8. The method of claim 3, wherein the amount of the compound administered is from about 0.01 to 10 mg/kg per day.

* * * * *